US008212111B2

(12) United States Patent
Mittendorf et al.

(10) Patent No.: US 8,212,111 B2
(45) Date of Patent: Jul. 3, 2012

(54) SUGAR AND LIPID METABOLISM REGULATORS IN PLANTS III

(75) Inventors: Volker Mittendorf, Hillsborough, NC (US); Heiko A. Haertel, Berlin (DE); Petra Cirpus, Mannheim (DE)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 12/943,056

(22) Filed: Nov. 10, 2010

(65) Prior Publication Data

US 2011/0055971 A1    Mar. 3, 2011

Related U.S. Application Data

(62) Division of application No. 12/631,262, filed on Dec. 4, 2009, now abandoned, which is a division of application No. 11/520,850, filed on Sep. 13, 2006, now abandoned, which is a division of application No. 10/217,939, filed on Aug. 12, 2002, now Pat. No. 7,135,618.

(60) Provisional application No. 60/311,414, filed on Aug. 10, 2001.

(51) Int. Cl.
*C12N 15/29* (2006.01)
*C12N 15/52* (2006.01)
*C12N 15/82* (2006.01)
*A01H 5/00* (2006.01)
*A01H 5/10* (2006.01)

(52) U.S. Cl. ........ 800/281; 800/284; 800/306; 800/312; 800/314; 800/320; 800/322

(58) Field of Classification Search .................. 800/281, 800/284
See application file for complete search history.

(56) References Cited

U.S. PATENT DOCUMENTS

| 5,955,650 | A | 9/1999 | Hitz |
| 6,084,164 | A | 7/2000 | Bidney et al. |
| 7,476,779 | B2 | 1/2009 | Lightner et al. |
| 2010/0088783 | A1 | 4/2010 | Härtel et al. |

FOREIGN PATENT DOCUMENTS

| WO | WO-99/40211 A2 | 8/1999 |
| WO | WO-01/26459 A2 | 4/2001 |
| WO | WO-02/22675 | 3/2002 |
| WO | WO-/0245485 A1 | 6/2002 |

OTHER PUBLICATIONS

Chopra, S. et al. SUcrose Synthase 2: At5G49190 1992.*
Bieniawska, Z. et al. Plant J. 2007 Marcy; 49(5): pp. 810-828.*
Leonard, J. et al. The Plant Journal (1998) vol. 13; No. 5, pp. 621-628.*
Bieniawska et al. Plant J. 2007; 49(5): pp. 810-828.*
Arenas-Huertero et al., "Analysis of *Arabidopsis* glucose insensitive mutants, gin5 and gin6, reveals a central role of the plant hormone ABA in the regulation of plant vegetative development by sugar", Genes Div., 2000,14:2085-2096.
Beaudoin et al., 2000, "Interactions between Abscisic Acid and Ethylene Signaling Cascades", Plant Cell, 2000:1103-1115.
Brenner, "Regulatory Function of Δ6 Desaturase—Key Enzyme of Polyunsaturated Fatty Acid Synthesis", Adv. Exp. Med. Biol., 1976, 83:85-101.
Browse et al,, "Fluxes through the prokaryotic and eukaryotic pathways of lipid syntesis in the '16.3' plant *Arabidopsis thaliana*", Biochemical J., 1986, 235:25-31.
Buhr, T., et al., "Ribozyme termination of RNA transcripts down-regulate seed fatty acid genes in transgenic soybean", The Plant Journal, 2002, 30(2):155-163.
Cahoon et al., "Expression of a coriander desaturase results in petroselinic acid production in transgenic tobacco", Proc. Natl. Acad. Sci. USA, 1992, 89:11184-11188.
Cohen, "Signal integration at the level of protein kinases, protein phosphatases and their substrates", Trends Biochem. Sci., 1992, 17:408-413.
Colon-Carmona et al., "Aux/IAA Proteins Are Phosphorylated by Phytochrome in Vitro", Plant Physiol., 2000, 124:1728-1738.
Frentzen, "Acyltransferases from basic science to modified seed oils", Lipids, 1998, 100:161-166.
Hartel et al., "DGD1-independent biosynthesis of extraplastidic galactolipids after phosphate deprivation in *Arabidopsis*", Proc. Natl. Acad. Sci. USA, 2000, 97:10649-10654.
Haslekas et al., "The expression of a peroxiredoxin antioxidant gene, AtPer1, in *Arabidopsis thaliana* is seed-specific and realted to dormancy", Plant Molecular Biology, 1998, 36:833-845.
Holvoet, P. et al., "The Arg123-Tyr166 Central Domain of Human ApoAI is Critical for Lecithin:Cholesterol Acyltransferase-Induced Hyperalphalipoproteinemia and HDL Remodeling in Transgenic Mice", Arteriosclerosis Thrombosis Vascular Biology, 2000, 459-466.
Hurry et al., "The role of inorganic phosphate in the development of freezing tolerance and the acclimatization of photosynthesis to low temperature is revealed by the *pho* mutants of *Arabidopsis thaliana*", Plant J., 2000, 24:383-396.
Kang & Rawsthorne, "Starch and fatty acid synthesis in plastids from developing embryos of oilseed rap (*Brassica napus* L.)", Plant J., 1994, 6:795-805.
Lee, et al., "Rice 1Cys-peroxiredoxin over-expressed in transgenic tobacco does not maintain dormancy but enhances antioxidant activity," FEBS Letters, 2000, 486:103-106.
Mahmoud, S.S. et al., "Metabolic Engineering of Essential Oil Yield and Composition in Mint by Altering Expression of Deoxyxylulose Phospate Reductoisomerase and Menthofuran Synthase", Proc. Natl. Acad. Sci. USA, 2001, 98(15):8915-8920.

(Continued)

*Primary Examiner* — Russell Kallis
(74) *Attorney, Agent, or Firm* — Connolly Bove Lodge & Hutz LLP

(57) ABSTRACT

Isolated nucleic acids and proteins associated with lipid and sugar metabolism regulation are provided. In particular, lipid metabolism proteins (LMP) and encoding nucleic acids originating from *Arabidopsis thaliana* are provided. The nucleic acids and proteins are used in methods of producing transgenic plants and modulating levels of seed storage compounds. Preferably, the seed storage compounds are lipids, fatty acids, starches or seed storage proteins.

23 Claims, 22 Drawing Sheets

OTHER PUBLICATIONS

Merlot et al., "The ABI1 and ABI2 protein phosphatases 2C act in a negative feedback regulatory loop of the abscisic acid signaling pathway", Plant J., 2001, 25:295-303.

Metz, J.G. et al., "Purification of a jojoba embryo fatty acyl-coenzyme a reductase and expression of its cDNA in high erucic acid rapeseed", Plant Physiology, 2000, 122:635-644.

Millar, et al., "All fatty acids are not equal: discrimination in plant membrane lipids", Trends Plant Sci., 2000, 5:95-101.

Mitsukawa et al., "Overexpression of an *Arabidopsis thaliana* high-affinity phosphate transporter gene in tobacco cultured cells enhances cell growth under phosphate-limited conditions", Proc. Natl. Acad. Sci. USA, 1997, 94:7098-7102.

Müller et al., "Lipid phosphorylation in chloroplast envelopes", J. Biol. Chem., 2000, 275:19475-19481.

Ogas et al., "Cellular differentiation regulated by Gibberellin in the *Arabidopsis thaliana pickle* mutant", Science, 1997, 277:91-94.

Ogas et al., "PICKLE is a CHD3 chromatin-remodeling factor that regulates the transition from embryonic to vegetative development in *Arabidopsis*", Proc. Natl. Acad. Sci USA, 1999, 96:13839-13844.

Ohlrogge & Browse, "Lipid Biosynthesis", Plant Cell, 1995, 7:957-970.

Ohlrogge, J. et al., "Fatty acid synthesis: from CO2 to functional genomics", Biochem. Society Transactions, 2000, 28(6):567-573.

Parveez, G.K.A., "Transgenic oil palm: production and projection," Biochemical Society, 2000, 28(6):969.

Plaxton, "The organization and regulation of plant glycolysis", Annu. Rev. Plant Physiol. Plant Mol. Biol., 1996, 47:185-214.

Ritchie & Gilroy, "Calcium-dependent protein phosphorylation may mediate the gibberellic acid response in barley aleurone", Plant Physiol., 1998, 116:765-776.

Savage & Ohlrogge, "Phosphorylation of pea chloroplast acetyl-CoA carboxylase", Plant J. 1999, 18:521-527.

Shanklin & Cahoon, Desaturation and related modifications of fatty acids, Annu. Rev. Plant Physiol. Plant Mol. Biol., 1998, 49:611-641.

Stacy et al., "The dormancy-related peroxiredoxin anti-oxidant, PER1, is localized to the nucleus of barley embryo and aleurone cells", The Plant Journal, 1999, 19(1):1-8.

Töpfer et al., "Modification of plant lipid synthesis", Science, 1995, 268:681-686.

Van De Loo et al., "Unusual Fatty Acids" in Lipid Metabolish in Plants, TS Moore, Jr., CRC Press, 1993, 91-126.

Van De Loo et al., "An oleate 12-hydroxylase from *Ricinus communis* L. is a fatty acyl desaturase homolog", Proc. Natl. Acad. Sci. USA, 1995, 92:6743-6747.

Voelker, "Plant ACYL-ACP thioesterases: Chain-length determining Enzymes in plant fatty acid biosynthesis", Genetic Engineering Ed. Setlow, 1996, 18:111-133.

Zhou et al., "Glucose and ethylene signal transduction crosstalk revealed by an *Arabidopsis* glucose-insensitive mutant", Proc. Natl. Acad. Sci. USA, 1998, 95:10294-10299.

Zou et al., "Modification of seed oil content and acyl composition in the *Brassicaceae* by expression of a yeast sn-2 acyltransferase gene", The Plant Cell, 1997, 9:909-923.

Broun, P. et al., 1998, Science 282:1315-1317.

"*Pisum sativum* mRNA for second sucrose synthase", Database EMBL Accession No. AJ001071, Aug. 12, 1997.

Edwards, J., et al., "Sucrose Partitioning in Developing Embryos of Round and Wrinkled Varieties of *Pisum sativum*", Phytochemistry, vol. 25, No. 9, (1986), pp. 2027-2032.

Weber, H., et al., "Expression of a Yeast-Derived Invertase in Developing Cotyledons of *Vicia narbonensis* Alters the Carbohydrate State and Affects Storage Functions" The Plant Journal, vol. 16, No. 2, (1998), ppl. 163-172.

Weber, H., et al., "Sugar Import and Metabolism During Seed Development", Trends in Plant Science, vol. 2, No. 5, (1997), pp. 169-174.

European Search Report for EP 09 00 4065 dated May 29, 2009.

* cited by examiner

Figure 1A

SEQ ID NO:1, Nucleotide sequence of the open reading frame of AT004002024

ATGCCAGGGATCACACTAGGAGACACGGTGCCGAACCTAGAAGTGGAGACG
ACACATGACAAGTTCAAACTTCATGACTACTTCGCCAATTCTTGGACCGTCCT
CTTCTCTCATCCCGGGGATTTCACACCCGTGTGCACCACGGAGCTTGGTGCGA
TGGCCAAATACGCTCATGAGTTCGATAAGAGAGGCGTGAAGCTCCTTGGTCT
GTCTTGTGACGATGTACAGTCACACAAAGACTGGATCAAAGATATTGAAGCC
TTTAATCACGGAAGCAAGGTGAATTACCCGATAATCGCTGACCCGAACAAAG
AGATCATTCCTCAGCTTAACATGATTGATCCAATTGAGAACGGACCGTCTCGT
GCCCTTCATATTGTTGGTCCTGACAGTAAGATAAAATTGAGCTTCTTGTATCC
GTCGACCACGGGACGTAACATGGACGAAGTATTGAGGGCTTTAGACTCGTTG
TTGATGGCGTCCAAGCACAATAACAAGATCGCCACTCCGGTTAACTGGAAGC
CAGATCAACCGGTTGTGATTTCGCCTGCTGTGTCGGACGAGGAAGCCAAAAA
GATGTTCCCACAGGGTTTCAAGACCGCCGATCTTCCGTCAAAGAAAGGCTATC
TGCGTCACACAGAGGTCTCTTGA

Figure 1B

SEQ ID NO:2, Amino acid sequence of the open reading frame of AT004002024

MPGITLGDTVPNLEVETTHDKFKLHDYFANSWTVLFSHPGDFTPVCTTELGA
MAKYAHEFDKRGVKLLGLSCDDVQSHKDWIKDIEAFNHGSKVNYPIIADPNK
EIIPQLNMIDPIENGPSRALHIVGPDSKIKLSFLYPSTTGRNMDEVLRALDSLLM
ASKHNNKIATPVNWKPDQPVVISPAVSDEEAKKMFPQGFKTADLPSKKGYLR
HTEVS

Figure 2A

SEQ ID NO:3, Nucleotide sequence of the open reading frame of AT004004054

AGAGGACGAGACAAGGGGGACATTTTTGTGTTTGAATATATCAACAAAAT
TAGATTTGATATGTGCTAAGATATGATGTATTAGTTGACATGACGATTTCT
TTTACTACTAGCCAAATCATTTAATAATCAGTCACAAAGAGGAAGAGAAA
TGTGTTCATTAGAGAAACGTGATCGTCTTTTCATACTAAAACTCACCGGCG
ACGGCGAACACCGTCTAAACCCAACCTTATTCGACTCTCTCCGCTCCACCA
TCAACCAAATCCGATCAGATCCATCATTTTCACAATCAGTACTCATCACAA
CATCAGATGGTAAATTCTTCTCCAACGGCTACGATCTCGCTTTAGCCGAGT
CAAATCCTTCTCTCTCTGTTGTAATGGACGCAAAACTTAGATCCTTAGTCG
CCGATCTAATCTCTCTTCCTATGCCAACAATCGCCGCCGTCACAGGTCACG
CTTCCGCCGCGGGATGTATTTTAGCGATGAGTCATGATTATGTATTGATGC
GTCGTGATAGAGGTTTTTTGTATATGAGTGAATTGGATATTGAGTTGATAG
TTCCGGCGTGGTTCATGGCTGTTATTAGGGGTAAGATTGGTTCTCCGGCGG
CCAGAAGGGATGTGATGTTGACGGCGGCGAAAGTGACGGCGGATGTGGG
TGTTAAGATGGGGATTGTTGATTCGGCGTATGGTAGTGCGGCGGAGACGG
TTGAAGCCGCCATTAAGTTAGGTGAGGAGATTGTTCAGAGAGGTGGTGAT
GGACACGTGTATGGTAAGATGAGAGAGAGTCTTTTAAGAGAGGTTCTTAT
CCATACGATTGGTGAATATGAGAGTGGTTCAAGTGTGGTGCGTAGCACTG
GATCTAAACTTTAGAACATGTTTGTACTTCTTGGGCTACTTGTCAGTTCTTT
TCAGCAATTGTTCTTTATA

Figure 2B

SEQ ID NO:4, Amino acid sequence of the open reading frame of of AT004004054

MCSLEKRDRLFILKLTGDGEHRLNPTLLDSLRSTINQIRSDPSFSQSVLITTSDG
KFFSNGYDLALAESNPSLSVVMDAKLRSLVADLISLPMPTIAAVTGHASAAGC
ILAMSHDYVLMRRDRGFLYMSELDIELIVPAWFMAVIRGKIGSPAARRDVML
TAAKVTADVGVKMGIVDSAYGSAAETVEAAIKLGEEIVQRGGDGHVYGKM
RESLLREVLIHTIGEYESGSSVVRSTGSKL

Figure 3A

SEQ ID NO:5, Nucleotide sequence of the open reading frame of AT004005069

ATGTCTCCACTTCTCCGGTTTAGAAAACTATCGTCCTTCTCTGAAGATACC
ATTAACCCTAAACCCAAACAATCGGCAACCGTCGAGAAACCAAAACGGC
GCCGTTCCGGGAGATGTAGCTGCGTTGACTCATGTTGCTGGTTGATTGGTT
ATCTCTGTACGGCGTGGTGGCTTCTCCTCTTTCTTTACCACTCTGTTCCGGT
CCCGGCGATGCTTCAAGCTCCGGAGTCTCCGGGAACTCGGTTGAGTCGAG
ACGGTGTCAAGGCGTTTCATCCGGTGATTCTTGTTCCGGGATTGTAACCG
GCGGGCTCGAGCTTTGGGAAGGTCGGCCTTGCGCTGAAGGACTCTTTCGT
AAACGTCTTTGGGGTGCTAGCTTCTCCGAGATTCTTAGAAGGCCATTGTGC
TGGTTGGAGCACTTATCTCTAGACAGTGAGACCGGTCTCGATCCATCGGG
AATCCGTGTCCGAGCAGTCCCAGGACTAGTGGCTGCAGACTATTTCGCAC
CATGCTACTTTGCTTGGGCAGTTCATAGAGAATTTGGCAAAAATTGGAT
ATGAAGGCAAGAACCTTCACATGGCCTCTTATGATTGGAGACTCTCTTTCC
ATAACACCGAGGTACGTGACCAATCGTTAAGTAGACTGAAGAGCAAAATC
GAGCTAATGTATGCCACCAATGGGTTTAAGAAAGTTGTGGTGGTTCCGCA
TTCAATGGGGGCTATCTATTTCCTTCACTTCCTTAAATGGGTAGAAACACC
TCTTCCTGATGGAGGCGGTGGGGGTGGTCCAGGTTGGTGTGCCAAACACA
TCAAATCCGTCGTCAACATTGGACCCGCCTTTTAGGTGTTCCTAAAGCCG
TCAGTAATTTACTTTCTGCTGAAGGCAAAGACATCGCTTACGCCAGATCTT
TGGCTCCAGGTCTCTTGGACTCGGAACTTCTCAAGCTGCAAACACTCGAAC
ACCTTATGCGGATGTCACATAGCTGGGATTCAATAGTATCTTTATTACCAA
AGGGCGGTGAGGCAATTTGGGGCGATCTAGACTCGCACGCTGAAGAAGG
ACTCAATTGTATTTACTCCAAGAGAAAATCATCGCAGCTATCGCTAAGTA
ATCTCCATAAACAAAACTACAGCCTTAAACCGGTGTCACGGGTGAAAGAA
CCCGCAAAGTACGGAAGAATCGTATCTTTCGGGAAACGAGCATCAGAACT
GCCTTCCTCACAACTCTCTACGCTAAACGTCAAGGAACTGTCAAGAGTAG
ATGGCAATTCAAATGACAGTACATCATGTGGAGAGTTTTGGTCAGAGTAC
AATGAAATGAGCCGAGAAAGCATAGTAAAAGTAGCAGAAAACACAGCTT
ATACAGCCACCACTGTTCTTGATCTTCTTCGATTTATAGCCCCTAAGATGA
TGAGACGAGCCGAAGCTCATTTCTCTCACGGCATTGCTGATGATCTTGATG
ACCCTAAGTATGGACATTATAAGTACTGGTCTAATCCACTCGAGACCAAA
TTACCGGAGGCACCAGAGATGGAAATGTACTGTCTTTACGGAGTAGGGAT
TCCGACCGAGAGATCTTACATATACAAGCTCGCAACCTCTTCCGGTAAAT
GCAAGAGCAGCATTCCCTTCCGGATAGATGGATCTCTGGATGGAGATGAC
GTTTGTCTTAAGGGAGGAACACGGTTTGCGGACGGAGACGAGAGTGTACC
GGTGATAAGTGCGGGGTTTATGTGCGCAAAGGGATGGAGAGGAAAAACA
CGGTTTAACCCGTCAGGGATGGATACATTCTTGCGGGAATACAAACATAA
GCCGCCGGGAAGTCTACTAGAAAGTCGAGGAACGGAAAGCGGAGCTCAT
GTAGACATAATGGGTAATGTTGGACTCATTGAAGATGTTTTGAGGATAGC
TGCCGGAGCTTCAGGCCAGGAGATTGGTGGCGATAGAATTTACTCGGATG
TGATGAGGATGTCGGAGAGAATTAGCATCAAGTTGTGA

Figure 3B

SEQ ID NO:6, Amino acid sequence of the open reading frame of AT004005069

```
MSPLLRFRKLSSFSEDTINPKPKQSATVEKPKRRRSGRCSCVDSCCWLIGYLCT
AWWLLLFLYHSVPVPAMLQAPESPGTRLSRDGVKAFHPVILVPGIVTGGLEL
WEGRPCAEGLFRKRLWGASFSEILRRPLCWLEHLSLDSETGLDPSGIRVRAVP
GLVAADYFAPCYFAWAVLIENLAKIGYEGKNLHMASYDWRLSFHNTEVRDQ
SLSRLKSKIELMYATNGFKKVVVVPHSMGAIYFLHFLKWVETPLPDGGGGGG
PGWCAKHIKSVVNIGPAFLGVPKAVSNLLSAEGKDIAYARSLAPGLLDSELLK
LQTLEHLMRMSHSWDSIVSLLPKGGEAIWGDLDSHAEEGLNCIYSKRKSSQLS
LSNLHKQNYSLKPVSRVKEPAKYGRIVSFGKRASELPSSQLSTLNVKELSRVD
GNSNDSTSCGEFWSEYNEMSRESIVKVAENTAYTATTVLDLLRFIAPKMMRR
AEAHFSHGIADDLDDPKYGHYKYWSNPLETKLPEAPEMEMYCLYGVGIPTER
SYIYKLATSSGKCKSSIPFRIDGSLDGDDVCLKGGTRFADGDESVPVISAGFMC
AKGWRGKTRFNPSGMDTFLREYKHKPPGSLLESRGTESGAHVDIMGNVGLIE
DVLRIAAGASGQEIGGDRIYSDVMRMSERISIKL
```

Figure 4A

SEQ ID NO:7, Nucleotide sequence of the open reading frame of AT004009021

ATGCGCTTCCGATCATTCTTCTTCTCCTCCTCTATCTTCTCCCTTTCACATTC
TCGCTCTCCTTCTCTTTCTTCCTCTCGTTTCTCCTCTCTCTCCGCCGCTATGT
CTCCTGCTCTCGAGAAATCCCGACAAGGCAATGGTGGATGTAATGATGAT
TCGAAATCTAAGGTCACGGTCGTTGGTAGTGGCAATTGGGGAAGTGTTGC
TGCTAAGCTCATTGCTTCTAATGCCCTCAAGCTTCCTTCTTTCCATGATGAA
GTGAGGATGTGGGTGTTTGAGGAGGTTCTACCAAATGGTGAGAAGCTCAA
TGATGTTATCAACAAGACCAATGAAAATGTCAAGTACCTCCCTGGGATTA
AGCTAGGAAGAAATGTTGTTGCGGATCCTGACCTTGAAAATGCAGTGAAG
GACGCGAACATGTTGGTTTTTGTTACACCGCATCAGTTTATGGATGGTATA
TGCAAGAAGTTAGATGGAAAGATCACAGGAGATGTTGAGGCTATATCTCT
TGTTAAAGGAATGGAAGTGAAGAAGGAAGGTCCTTGTATGATCTCAAGTC
TCATTTCCAAGCAACTTGGTATCAATTGTTGTGTTCTTATGGGCGCAAACA
TTGCAAACGAGATAGCTGTGGAGAAGTTTAGTGAAGCAACGGTTGGATAT
AGAGGGAGTAGAGAAATAGCGGACACATGGGTTCAGTTGTTTAGTACTCC
GTATTTTATGGTCACACCGGTCCATGATGTGGAAGGAGTAGAGTTATGTG
GGACTTTGAAGAATGTAGTTGCTATTGCAGCGGGTTTCGTGGACGGTTTGG
AAATGGGTAATAACACAAAGGCTGCAATCATGAGGATTGGTCTAAGAGA
GATGAAAGCACTCTCAAAGCTTTTGTTTCCATCTGTTAAAGATAGTACTTT
CTTCGAGAGCTGCGGTGTAGCAGATGTCATTACAACTTGCTTAGGAGGAA
GAAACCGGAGAGTTGCGGAAGCATTTGCAAAAAGCAGAGGAAAAAGGTC
TTTTGATGAGCTTGAAGCAGAGATGCTACAAGGGCAAAAGCTACAGGGGG
TATCGACGGCAAGAGAGGTCTACGAGGTGTTGAAACATTGTGGATGGTTG
GAGATGTTCCGCTCTTTTCAACGGTTCACCAAATCTGCACTGGTCGTCTT
CAACCTGAAGCCATCGTCCAATACCGCGAGAACAAACTATAA

Figure 4B

SEQ ID NO:8, Amino acid sequence of the open reading frame of AT004009021

MRFRSFFFSSSIFSLSHSRSPSLSSSRFSSLSAAMSPALEKSRQGNGGCNDDSKS
KVTVVGSGNWGSVAAKLIASNALKLPSFHDEVRMWVFEEVLPNGEKLNDVI
NKTNENVKYLPGIKLGRNVVADPDLENAVKDANMLVFVTPHQFMDGICKKL
DGKITGDVEAISLVKGMEVKKEGPCMISSLISKQLGINCCVLMGANIANEIAV
EKFSEATVGYRGSREIADTWVQLFSTPYFMVTPVHDVEGVELCGTLKNVVAI
AAGFVDGLEMGNNTKAAIMRIGLREMKALSKLLFPSVKDSTFFESCGVADVI
TTCLGGRNRRVAEAFAKSRGKRSFDELEAEMLQGQKLQGVSTAREVYEVLK
HCGWLEMFPLFSTVHQICTGRLQPEAIVQYRENKL

Figure 5A

SEQ ID NO:9, Nucleotide sequence of the open reading frame of Pk109

ATGTTGCCCAGATTAGCTCGAGTCGTCACTCAAACCTCAAAGCTTCGATCT
TTGACCACTAATGGATCGATGAAAAATCTCTCCTTTTTCTCCCGATATGGG
TACGCGACTGTTGCGCCGGCGGCAGCTGATCCTCCGTCGCAGAAGGATTT
CCCCAGTAAATCTCCGCTGTTAATGCGTAGTTGTTGTGAATGTTAGGTCT
CACTATAGTATTCGAACCTAAGCTCAATTTGATTCTCTCTGTTTCTAGTTTC
ATCGAATGCGGGACTAAAATAAACTTGGATAAGATGTTTTGGTCAAAGCC
ATGTTCATTGGCTCTGCCTAAAGACTCTCCTCTCAGAATTGATGAACCAGA
CTATGTAGGGATTCGTCGTTTCATACTAAAGATGATGATGTTCTATAGCAA
ACAGAGCATGTCTATCCGTGGGGCTAACGTGATCTACAAGCGGATCATTG
CACAAGTTGATAAACCTGCAATATATGATGTATTCAACTTGGAGAAAACA
TTCAAAATAACGTATTCGCTGCTTGTCCTTCATATGTGGCTTGTTTTACGCC
GCTTGAAGGAAGATGGACAGGAAGGTGTTGACCTTGGTCAATACGTCTAT
GAGATCTACAATCATGATGTTGAACTCAGGGTATCTAAAGCCGGGGTTAA
CTTGCTGCTAGCCAAGTGGATGAAGGAGTTGGAGAGAATATTTATGGAA
ATGTTGTTGCCTATGATGCTGCGCTACTTCCGGAAGCTAAACCAAATGACC
TACAAATCAAATTATGGAGGAACGTATTTTCTGATGATGGAACAACAACA
CCTGATAACACAGATTTAAAAACAGCACAGGCAATGGCAAGATATGTCCG
GAGAGAACTTGGTTCTCTTTCTTTAACAGGTACCTATGACGCTATAGTTGG
AATGCCTCATTATGTTACTCGCATTTGCATTTCGAATAGACATGCCTTTCT
TATATGGTTCTTTTTTGTCATACACAGATAAAGAGTCCATATTCTCCGGCA
ATTTCTCCTTCACCCCTTTGGAGAACAAGCCCCTGTGATTTGAATGAAATT
AGAAGAAGCTGTGGTGCTTTGCGAATCAATCTTTCATTTGTTTCTCTGTTTC
ATTTGATTTACTTATATCAAACCAAAGAAACCTACACAAGGGAATGTGCT
AGCTGTTAG

Figure 5B

SEQ ID NO:10, Amino acid sequence of the open reading frame of Pk109

MLPRLARVVTQTSKLRSLTTNGSMKNLSFFSRYGYATVAPAAADPPSQKDFP
SKSPLLMRSCCECLGLTIVFEPKLNLILSVSSFIECGTKINLDKMFWSKPCSLAL
PKDSPLRIDEPDYVGIRRFILKMMMFYSKQSMSIRGANVIYKRIIAQVDKPAIY
DVFNLEKTFKITYSLLVLHMWLVLRRLKEDGQEGVDLGQYVYEIYNHDVEL
RVSKAGVNLLLAKWMKELERIFYGNVVAYDAALLPEAKPNDLQIKLWRNVF
SDDGTTTPDNTDLKTAQAMARYVRRELGSLSLTGTYDAIVGMPHYVTRICIS
NRHAFSYMVLFCHTQIKSPYSPAISPSPLWRTSPCDLNEIRRSCGALRINLSFVS
LFHLIYLYQTKETYTRECASC

Figure 5C

SEQ ID NO:11, Nucleotide sequence of the open reading frame of Pk109-1

ATGTTGCCCAGATTAGCTCGAGTCGTCACTCAAACCTCAAAGCTTCGATCT
TTGACCACTAATGGATCGATGAAAAATCTCTCCTTTTTCTCCCGATATGGG
TACGCGACTGTTGCGCCGGCGGCAGCTGATCCTCCGTCGCAGAAGGATTT
CCCCAGTAAATCTCCGATAAACTTGGATAAGATGTTTTGGTCAAAGCCAT
GTTCATTGGCTCTGCCTAAAGACTCTCCTCTCAGAATTGATGAACCAGACT
ATGTAGGGATTCGTCGTTTCATACTAAAGATGATGATGTTCTATAGCAAAC
AGAGCATGTCTATCCGTGGGGCTAACGTGATCTACAAGCGGATCATTGCA
CAAGTTGATAAACCTGCAATATATGATGTATTCAACTTGGAGAAAACATT
CAAAATAACGTATTCGTTGCTTGTCCTTCATATGTGGCTTGTTTTACGCCG
CTTGAAGGAAGATGGACAGGAAGGTGTTGACCTTGGTCAATACGTCTATG
AGATCTACAATCATGATGTTGAACTCAGGGTATCTAAAGCCGGGGTTAAC
TTGCTGCTAGCCAAGTGGATGAAGGAGTTGGAGAGAATATTTTATGGAAA
TGTTGTTGCCTATGATGCTGCGCTACTTCCGGAAGCTAAACCAAATGACCT
ACAAATCAAATTATGGAGGAACGTATTTTCTGATGATGGAACAACAACAC
CTGATAACACAGATTTAAAAACAGCACAGGCAATGGCAAGATATGTCCGG
AGAGAACTTGGTTCTCTTTCTTTAACAGATAAAGAGTCCATATTCTCCGGC
AATTTCTCCTTCACCCCTTTGGAGAACAAGCCCCTG

Figure 5D

SEQ ID NO:12, Amino acid sequence of the open reading frame of Pk109-1

MLPRLARVVTQTSKLRSLTTNGSMKNLSFFSRYGYATVAPAAADPPSQKDFP
SKSPINLDKMFWSKPCSLALPKDSPLRIDEPDYVGIRRFILKMMMFYSKQSMSI
RGANVIYKRIIAQVDKPAIYDVFNLEKTFKITYSLLVLHMWLVLRRLKEDGQE
GVDLGQYVYEIYNHDVELRVSKAGVNLLLAKWMKELERIFYGNVVAYDAA
LLPEAKPNDLQIKLWRNVFSDDGTTTPDNTDLKTAQAMARYVRRELGSLSLT
DKESIFSGNFSFTPLENKPL

Figure 6A

SEQ ID NO:13, Nucleotide sequence of the open reading frame of Pk110

ATGTCGGCCGGTAACGGAAATGCTACTAACGGTGACGGAGGGTTTAGTTT
CCCTAAAGGACCGGTGATGCCGAAGATAACGACCGGAGCAGCAAAGAGA
GGTAGCGGAGTCTGCCACGACGATAGTGGTCCGACGGTGAATGCCACAAC
CATCGATGAGCTTCATTCGTTACAGAAGAAACGTTCTGCTCCTACCACACC
GATCAACCAAAACGCCGCCGCTGCTTTTGCCGCCGTCTCCGAGGAGGAGC
GTCAGAAGATTCAGCTTCAATCTATCAGTGCATCGTTAGCATCGTTAACGA
GAGAGTCAGGACCAAAGGTGGTGAGAGGAGATCCGGCGGAGAAGAAGAC
CGATGGTTCAACTACTCCGGCGTACGCTCACGCCAACATCATTCTATCTT
TTCTCCGGCTACTGGTGCTGTCAGTGATAGCTCCTTGAAGTTTACTCACGT
CCTCTACAATCTTTCGCCTGCAGAGCTTTATGAGCAAGCTATTAAGTATGA
GAAAGGTTCGTTTATCACTTCTAATGGAGCTTTGGCGACGCTTTCTGGTGC
TAAGACTGGTCGTGCTCCCAGAGATAAGCGTGTTGTTAGAGATGCTACTA
CTGAGGATGAGCTTTGGTGGGGAAAGGGTTCGCCGAATATCGAAATGGAT
GAACATACTTTCATGGTGAACAGAGAAAGAGCTGTTGATTACTTGAATTC
CTTGGAAAAGGTCTTTGTCAATGACCAATACTTAAACTGGGATCCAGAGA
ACAGAATCAAAGTCAGGATTGTCTCAGCTAGAGCTTACCATTCATTGTTTA
TGCACAACATGTGTATCCGACCAACTCAGGAGGAGCTTGAGAGCTTTGGT
ACTCCGGATTTTACTATATACAATGCTGGGCAGTTTCCATGTAATCGTTAC
ACTCATTACATGACTTCGTCCACTAGCGTAGACCTTAATCTGGCTAGGAGG
GAAATGGTTATACTTGGTACTCAGTATGCTGGGGAAATGAAGAAGGGTCT
TTTCAGTGTGATGCATTACCTTATGCCTAAGCGTCGTATTCTCTCCCTTCAT
TCTGGATGCAATATGGGAAAGATGGAGATGTTGCTCTCTTCTTTGGACTT
TCAGGTACCGGGAAGACAACGCTGTCTACTGATCACAACAGGTATCTTAT
TGGAGATGATGAGCATTGTTGGACTGAGACTGGTGTTTCGAACATTGAGG
GTGGGTGCTATGCTAAGTGTGTTGATCTTTCGAGGGAGAAGGAGCCTGAT
ATCTGGAACGCTATCAAGTTTGGAACAGTTTTGGAAAATGTTGTGTTTGAT
GAGCACACCAGAGAAGTGGATTACTCTGATAAATCTGTTACAGAGAACAC
ACGTGCTGCCTACCCAATTGAGTTCATTCCAAATGCGAAAATACCTTGTGT
TGGTCCACACCCGACAAATGTGATACTTCTGGCTTGTGATGCCTTTGGTGT
TCTCCCACCTGTGAGCAAGCTGAATCTGGCACAAACCATGTACCACTTCAT
CAGTGGTTACACTGCTCTGGTTGCTGGCACAGAGGATGGTATCAAGGAGC
CAACAGCAACATTCTCAGCTTGCTTTGGTGCAGCTTTCATAATGTTGCATC
CCACAAAGTATGCAGCTATGTTAGCTGAGAAGATGAAGTCACAAGGTGCT
ACTGGTTGGCTCGTCAACACTGGTTGGTCTGGTGGCAGTTATGGTGTTGGA
AACAGAATCAAGCTGGCATACACTAGAAAGATCATCGATGCAATCCATTC
GGGCAGTCTCTTGAAGGCAAACTACAAGAAACCGAAATCTTTGGATTTG
AAATCCCAACTGAGATCGAAGGGATACCTTCAGAGATCTTGGACCCCGTC
AACTCCTGGTCTGATAAGAAGGCACACAAGATACTCTGGTGAAACTGGG
AGGTCTGTTCAAGAAGAACTTCGAGGTTTTGCTAACCATAAGATTGGTGT
GGATGGTAAGCTTACGGAGGAGATTCTCGCTGCTGGTCCTATCTTTTAG

Figure 6B

SEQ ID NO:14, Amino acid sequence of the open reading frame of Pk110

MSAGNGNATNGDGGFSFPKGPVMPKJTTGAAKRGSGVCHDDSGPTVNATTI
DELHSLQKKRSAPTTPINQNAAAAFAAVSEEERQKIQLQSISASLASLTRESGP
KVVRGDPAEKKTDGSTTPAYAHGQHHSIFSPATGAVSDSSLKFTHVLYNLSP
AELYEQAIKYEKGSFITSNGALATLSGAKTGRAPRDKRVVRDATTEDELWWG
KGSPNIEMDEHTFMVNRERAVDYLNSLEKVFVNDQYLNWDPENRIKVRIVSA
RAYHSLFMHNMCIRPTQEELESFGTPDFTIYNAGQFPCNRYTHYMTSSTSVDL
NLARREMVILGTQYAGEMKKGLFSVMHYLMPKRRILSLHSGCNMGKDGDV
ALFFGLSGTGKTTLSTDHNRYLIGDDEHCWTETGVSNIEGGCYAKCVDLSRE
KEPDIWNAIKFGTVLENVVFDEIITREVDYSDKSVTENTRAAYPIEFIPNAKIPC
VGPHPTNVILLACDAFGVLPPVSKLNLAQTMYHFISGYTALVAGTEDGIKEPT
ATFSACFGAAFIMLHPTKYAAMLAEKMKSQGATGWLVNTGWSGGSYGVGN
RIKLAYTRKIIDAIHSGSLLKANYKKTEIFGFEIPTEIEGIPSEILDPVNSWSDKK
AHKDTLVKLGGLFKKNFEVFANHKIGVDGKLTEEILAAGPIF

Figure 7A

SEQ ID NO:15, Nucleotide sequence of the open reading frame of Pk111

ATGGTTTCGTTTACGGGTTTCGCTTTCGTATTTGGAATTCTACTTGGGATTC
TTGCGATCGTTACGGCGGAAGTTGTAGGGTTTTTGTATCTTCTGAAGCGAT
TGAATCGGAAAAGAGATCGTCAGGAATCGAATTCGAGTTCTGATCCAAAC
TTCAAGAGTTTTGATCCTCGCCAATCCATTGATTTTAGTCTCAACAAACAG
GGAGTGATCTGGATATTGGAATTAGATGAAAATGTAAAAGATTGGATGAA
GGAGAAATTACCAAAAGAGCAAAAGAAGAAGAGTAGATCTCTTGGAG
GTACATCCAGTTAGGAGATTTGCTCGCATCAAAGATCATAAGCTCATCTTG
TCTGATTCATTAGATGGCCCTCAGACTCCTATTACTTTGAAAGGTTGCTTT
GTTGACGCTGTTTCAGGCTCTGGACCAACAAGGAAATGGGCTAAAAGATT
TCCTATACAAGTAGAAAGCAAAACTTCTGTCTTGTATAAAGGAAACAGAG
TGTTTTACATTTTCTTAGAGACTTCTTGGGAGAAGGAGTCATGGTGTAAAG
CTCTTCGTCTTGCTGCTTGCGAGAATCAGGAAAGGTTTATTTGGTCCACCA
AATTGAAAGAAGATTTCCGGAACTATCTGGCTTCCCTTAATGCTGCCTATC
CTTCTTTTATGAAACCATCAGCTGGGTTTAGTTTTGAGTCATTGGACAAGG
GGCTTAAAGCAGATGGTCCTTCATCAAAGGTTCGTTTGATCTGGAAGAAA
TTTTCGAAAAAGTGCTCAACTAAAGTGAATTTTCCCCCGTCGATTCGTGAC
GACAAGAAGACTTCATCCCGTTCTTACCAAGATTCACAATCTACTGGTAGC
TCTGGAAAGAGTACCTCAGCAAGGAGGATGCAAGATAACATCCCGGAGG
AAACTGATGTCCAAGTTATCTCACGTTCTTGGAGCCATAGCAGTCATGCAT
CAGATGTAGATTCAGAAGACAAGTCTTTTGATGAAGGAACATTGGCATTG
AACGTAGTATTATCTCGGCTGTTTTTTGATGTTAAACAGAACACAGTACTG
AAGAATTTAGTGCGCGAACGAATCCAGCGGATAATGTCCAACATGAGAAT
TCCCAGCTACATAGGCGAATTAATCTGCTGTGACGTAGACATTGGAAATC
TCCCGCCTTACATACACGGTACGAGAATTCTTCCAATGGAGATGAATGGT
GTGTGGGCGTTCGAAATAGATATTGAATACACTGGTGGTGCGGGACTTGA
AGTTGAAACTCGGGTTGATGCTCGAGAGGAAGATTTGCAGAAAGGCATAG
CTGAGGGAAAGTTGCAGCCAAATTCTGCTGGGGATGTTCCACCAGATCTC
CTTGAAGGTCTTGCAGATTTTGAAAAGCAATTAAATGTTCCCGGAGGAAC
TGTTGATGCACAAGATGTGAAAAGTGGTGGAACTGATAAAGCTGATGAAT
CGAAGGGTCCAAAAGGTACAAAAACAGGTTCGAGCAATGGATCCAAGTG
GAAGTCTATGCTGAAGAACATCGTTGAACAAGTTTCCCAGGTCCCAATTA
CTTTGTCTATAGGGGTGTCTTCGCTTCGAGGGACACTGTGTGTACACATGA
AGCCGCCTCCATCTGATCAACTGTGGTTTGGCTTCACAAGCATGCCTGATA
TTGAATTCAACCTTGTCTCTTCTGTTGGTGAACACAAAATCACAAACAGCC
ATGTTGCTATGTTCTTGGTCAACCGGTTCAAGACGGCGATACGAGACGTC
ATGGTGCTCCCCAATTGTGAAAGCGTTACCATTCCTTGGATGACAGCTGAA
AAGGATGATTGGGTCGAACGCAATGTCGCTCCATTCATGTGGCTGAATCA
AGACTCCACCAGTGATCGCGAAAATTTGGAAGCTGCAGAAGCGAAATCTA
AAGCTGACAAGCCACCGACTTCTGAACAAATGCAGAAAACTGTCAACATC
CCGCAGAAGCCTAGAATTGAGGAAGAATCTGTGTCGGCTGACACTGCACC
ATCAGCTAATTCCATAGCTCTCCTAGTAGAGAGTGACAAATCCTTAGAAG
AACTCAAGACTCCACTGCTGGAAAGCAGCGAAAAGCATGATACAATAGC
GAGAGGAGGCAGTGCGGGAGATATAATTCCGGGTATTGGTCAATCACCGT
CTATGTCGACTGTTTCGGGTGAAGAGGATGATT

FIGURE 7A CONTINUED

CAAATTCAAAAGGAAAGAAAATGGGGGCAGCAAAGGCGAGGATGTTCGA
TTTTAGGAAGAAAGTGGGAGAGAAGTTTGAAGAGAAGAAACGTCACGTT
GAGGAAAAAAGTAGACAGATTGTTGAAAAGATGAGAGGACCTTGA

Figure 7B

SEQ ID NO:16, Amino acid sequence of the open reading frame of Pk111

MVSFTGFAFVFGILLGILAIVTAEVVGFLYLLKRLNRKRDRQESNSSSDPNFKS
FDPRQSIDFSLNKQGVIWILELDENVKDWMKEKLPKEQKKKRVDLLEVHPVR
RFARIKDHKLILSDSLDGPQTPITLKGCFVDAVSGSGPTRKWAKRFPIQVESKT
SVLYKGNRVFYIFLETSWEKESWCKALRLAACENQERFIWSTKLKEDFRNYL
ASLNAAYPSFMKPSAGFSFESLDKGLKADGPSSKVRLIWKKFSKKCSTKVNFP
PSIRDDKKTSSRSYQDSQSTGSSGKSTSARRMQDNIPEETDVQVISRSWSHSSII
ASDVDSEDKSFDEGTLALNVVLSRLFFDVKQNTVLKNLVRERIQRIMSNMRIP
SYIGELICCDVDIGNLPPYIHGTRILPMEMNGVWAFEIDIEYTGGAGLEVETRV
DAREEDLQKGIAEGKLQPNSAGDVPPDLLEGLADFEKQLNVPGGTVDAQDV
KSGGTDKADESKGPKGTKTGSSNGSKWKSMLKNIVEQVSQVPITLSIGVSSLR
GTLCVHMKPPPSDQLWFGFTSMPDIEFNLVSSVGEHKITNSHVAMFLVNRFK
TAIRDVMVLPNCESVTIPWMTAEKDDWVERNVAPFMWLNQDSTSDRENLEA
AEAKSKADKPPTSEQMQKTVNIPQKPRIEEESVSADTAPSANSIALLVESDKSL
EELKTPLLESSEKHDTIARGGSAGDIIPGIGQSPSMSTVSGEEDDSNSKGKKMG
AAKARMFDFRKKVGEKFEEKKRHVEEKSRQIVEKMRGP

Figure 7C

SEQ ID NO:17, Nucleotide sequence of the open reading frame of Pk111-1

ATGAAACCATCAGCTGGGTTTAGTTTTGAGTCATTGGACAAGGGGCTTAA
AGCAGATGGTCCTTCATCAAAGGTTCGTTTGATCTGGAAGAAATTTTCGAA
AAAGTGCTCAACTAAAGTGAATTTTCCCCCGTCGATTCGTGACGACAAGA
AGACTTCATCCCGTTCTTACCAAGATTCACAATCTACTGGTAGCTCTGGAA
AGAGTACCTCAGCAAGGAGGATGCAAGATAACATCCCGGAGGAAACTGA
TGTCCAAGTTATCTCACGTTCTTGGAGCCATAGCAGTCATGCATCAGATGT
AGATTCAGAAGACAAGTCTTTTGATGAAGGAACATTGGCATTGAACGTAG
TATTATCTCGGCTGTTTTTGATGTTAAACAGAACACAGTACTGAAGAATT
TAGTGCGCGAACGAATCCAGCGGATAATGTCCAACATGAGAATTCCCAGC
TACATAGGCGAATTAATCTGCTGTGACGTAGACATTGGAAATCTCCCGCCT
TACATACACGGTACGAGAATTCTTCCAATGGAGATGAATGGTGTGTGGGC
GTTCGAAATAGATATTGAATACACTGGTGGTGCGGGACTTGAAGTTGAAA
CTCGGGTTGATGCTCGAGAGGAAGATTTGCAGAAAGGCATAGCTGAGGGA
AAGTTGCAGCCAAATTCTGCTGGGGATGTTCCACCAGATCTCCTTGAAGGT
CTTGCAGATTTTGAAAAGCAATTAAATGTTCCCGGAGGAACTGTTGATGC
ACAAGATGTGAAAAGTGGTGGAACTGATAAAGCTGATGAATCGAAGGGT
CCAAAAGGTACAAAAACAGGTTCGAGCAATGGATCCAAGTGGAAGTCTAT
GCTGAAGAACATCGTTGAACAAGTTTCCCAGGTCCCAATTACTTTGTCTAT
AGGGGTGTCTTCGCTTCGAGGGACACTGTGTGTACACATGAAGCCGCCTC
CATCTGATCAACTGTGGTTTGGCTTCACAAGCATGCCTGATATTGAATTCA
ACCTTGTCTCTTCTGTTGGTGAACACAAAATCACAAACAGCCATGTTGCTA
TGTTCTTGGTCAACCGGTTCAAGACGGCGATACGAGACGTCATGGTGCTC
CCCAATTGTGAAAGCGTTACCATTCCTTGGATGACAGCTGAAAAGGATGA
TTGGGTCGAACGCAATGTCGCTCCATTCATGTGGCTGAATCAAGACTCCAC
CAGTGATCGCGAAAATTTGGAAGCTGCAGAAGCGAAGTCTAAAGCTGACA
AGCCACCGACTTCTGAACAAATGCAGAAAACTGTCAACATCCCGCAGAAG
CCTAGAATTGAGGAAGAATCTGTGTCGGCTGACACTGCACCATCAGCTAA
TTCCATAGCTCTCCTAGTAGAGAGTGACAAATCCTTAGAAGAACTCAAGA
CTCCACTGCTGGAAAGCAGCGAAAGCATGATACAATAGCGAGAGGAGG
CAGTGCGGGAGATATAATTCCGGGTATTGGTCAATCACCGTCTATGTCGA
CTGTTTCGGGTGAAGAGGATGATTCAAATTCAAAAGGAAAGAAAATGGG
GGCAGCAAAGGCGAGGATGTTCGATTTTAGGAAGAAAGTGGGAGAGAAG
TTTGAAGAGAAGAAACGTCACGTTGAGGAAAAAGTAGACAGATTGTTG
AAAAGATGAGAGGACCTTGA

Figure 7D

SEQ ID NO:18, Amino acid sequence of the open reading frame of Pk111-1

MKPSAGFSFESLDKGLKADGPSSKVRLIWKKFSKKCSTKVNFPPSIRDDKKTS
SRSYQDSQSTGSSGKSTSARRMQDNIPEETDVQVISRSWSHSSHASDVDSEDK
SFDEGTLALNVVLSRLFFDVKQNTVLKNLVRERIQRIMSNMRIPSYIGELICCD
VDIGNLPPYIHGTRILPMEMNGVWAFEIDIEYTGGAGLEVETRVDAREEDLQK
GIAEGKLQPNSAGDVPPDLLEGLADFEKQLNVPGGTVDAQDVKSGGTDKAD
ESKGPKGTKTGSSNGSKWKSMLKNIVEQVSQVPITLSIGVSSLRGTLCVHMKP
PPSDQLWFGFTSMPDIEFNLVSSVGEHKITNSHVAMFLVNRFKTAIRDVMVLP
NCESVTIPWMTAEKDDWVERNVAPFMWLNQDSTSDRENLEAAEAKSKADK
PPTSEQMQKTVNIPQKPRIEEESVSADTAPSANSIALLVESDKSLEELKTPLLES
SEKHDTIARGGSAGDIIPGIGQSPSMSTVSGEEDDSNSKGKKMGAAKARMFDF
RKKVGEKFEEKKRHVEEKSRQIVEKMRGP

Figure 8A

SEQ ID NO:19, Nucleotide sequence of the open reading frame of Pk113

ATGGTCGATAAACCAAATCAGATAATGGAAGAAGAAGGGAGATTCGAAG
CGGAGGTTGCGGAAGTGCAGACTTGGTGGAGCTCAGAGAGGTTCAAGCTA
ACAAGGCGCCCTTACACTGCCCGTGACGTGGTGGCTCTACGTGGCCATCTC
AAGCAAGGCTATGCTTCGAACGAGATGGCTAAGAAGCTGTGGAGAACGCT
CAAAAGCCATCAAGCCAACGGTACGGCCTCTCGCACCTTCGGAGCGTTGG
ACCCTGTTCAGGTGACCATGATGGCTAAACATTTGGACACCATCTATGTCT
CTGGTTGGCAGTGCTCGTCCACTCACACATCCACTAATGAGCCTGGTCCTG
ATCTTGCTGATTATCCGTACGACACCGTTCCTAACAAGGTTGAACACCTCT
TCTTCGCTCAGCAGTACCATGACAGAAAGCAGAGGGAGGCAAGAATGAG
CATGAGCAGAGAAGAGAGGACAAAAACTCCGTTCGTGGACTACCTAAAG
CCCATCATCGCCGACGGAGACACCGGCTTTGGCGGCACCACCGCCACCGT
CAAACTCTGCAAGCTTTTCGTTGAAAGAGGCGCCGCTGGGGTCCACATCG
AGGACCAGTCCTCCGTCACCAAGAAGTGTGGCCACATGGCCGGAAAGGTC
CTCGTGGCAGTCAGCGAACACATCAACCGCCTTGTCGCGGCTCGGCTCCA
GTTCGACGTGATGGGTACAGAGACCGTCCTTGTTGCTAGAACAGATGCGG
TCGCAGCTACTCTGATCCAGTCGAACATTGACGCGAGGGACCACCAGTTC
ATCCTCGGTGCCACTAACCCGAGCCTTAGAGGCAAGAGTTTGTCCTCGCTT
CTGGCTGAGGGAATGACTGTAGGCAAGAATGGTCCGGCGTTGCAATCCAT
TGAAGATCAGTGGCTTGGCTCGGCCGGTCTTATGACTTTCTCGGAAGCTGT
CGTGCAGGCCATCAAGCGCATGAACCTCAACGAGAACGAGAAGAATCAG
AGACTGAGCGAGTGGTTAACCCATGCAAGGTATGAGAACTGCCTGTCAAA
TGAGCAAGGCCGAGTGTTAGCAGCAAAACTTGGTGTGACAGATCTTTTCT
GGGACTGGGACTTGCCGAGAACCAGAGAAGGATTCTACCGGTTCCAAGGC
TCGGTCGCAGCGGCCGTGGTCCGTGGCTGGGCCTTTGCACAGATCGCAGA
CATCATCTGGATGGAAACGGCAAGCCCTGATCTCAATGAATGCACCCAAT
TCGCCGAAGGTATCAAGTCCAAGACACCGGAGGTCATGCTCGCCTACAAT
CTCTCGCCGTCCTTCAACTGGGACGCTTCCGGTATGACGGATCAGCAGATG
GTTGAGTTCATTCCGCGGATTGCTAGGCTCGGATATTGTTGGCAGTTCATA
ACGCTTGCGGGTTTTCCATGCGGATGCTCTTGTGGTTGATACATTTGCAAAG
GATTACGCTAGGCGCGGGATGTTGGCTTATGTGGAGAGGATACAAAGAGA
AGAGAGGACCCATGGGGTTGACACTTTGGCTCACCAGAAATGGTCCGGTG
CTAATTACTATGATCGTTATCTTAAGACCGTCCAAGGTGGAATCTCCTCCA
CTGCAGCCATGGGAAAAGGTGTCACTGAAGAACAGTTCAAGGAGAGTTG
GACAAGGCCGGGAGCTGATGGAATGGGTGAAGGGACTAGCCTTGTGGTC
GCCAAGTCAAGAATGTAA

Figure 8B

SEQ ID NO:20, Amino acid sequence of the open reading frame of Pk113

MVDKPNQIMEEEGRFEAEVAEVQTWWSSERFKLTRRPYTARDVVALRGHLK
QGYASNEMAKKLWRTLKSHQANGTASRTFGALDPVQVTMMAKHLDTIYVS
GWQCSSTHTSTNEPGPDLADYPYDTVPNKVEHLFFAQQYHDRKQREARMSM
SREERTKTPFVDYLKPIIADGDTGFGGTTATVKLCKLFVERGAAGVHIEDQSS
VTKKCGHMAGKVLVAVSEHINRLVAARLQFDVMGTETVLVARTDAVAATLI
QSNIDARDHQFILGATNPSLRGKSLSSLLAEGMTVGKNGPALQSIEDQWLGSA
GLMTFSEAVVQAIKRMNLNENEKNQRLSEWLTHARYENCLSNEQGRVLAAK
LGVTDLFWDWDLPRTREGFYRFQGSVAAAVVRGWAFAQIADIIWMETASPD
LNECTQFAEGIKSKTPEVMLAYNLSPSFNWDASGMTDQQMVEFIPRIARLGY
CWQFITLAGFHADALVVDTFAKDYARRGMLAYVERIQREERTHGVDTLAHQ
KWSGANYYDRYLKTVQGGISSTAAMGKGVTEEQFKESWTRPGADGMGEGT
SLVVAKSRM

Figure 9A

SEQ ID NO:21, Nucleotide sequence of the open reading frame of Pk114

ATGGGGTTAGAGAGGAAAGTGTACGGTTTGGTTATGGTATCTTTGGTACTT
ATGGCTATTGCAACGATGTGTTGTGTCCAAGCTACGATCGAGGAAGAAGC
GGCTAAGGATGAATCATGGACTGATTGGGCAAAGGAGAAGATCGGTCTCA
AGCACGAAGACAACATCCAACCCACTCACACCACCACGACCGTTCAAGAC
GACGCTTGGAGAGCGAGTCAAAAAGCCGAGGACGCAAAGGAGGCGGCTA
AACGCAAAGCAGAGGAAGCGGTTGGAGCCGCGAAGGAGAAAGCGGGTTC
GGCATACGAGACAGCTAAATCGAAAGTTGAGGAGGGTTTGGCTTCTGTAA
AAGACAAGGCCTCGCAGAGTTACGACTCAGCTGGTCAAGTTAAGGATGAC
GTGTCTCACAAGTCAAAGCAAGTTAAAGATAGCTTGTCGGGAGACGAAAA
CGATGAGTCTTGGACCGGTTGGGCCAAAGAGAAATCGGAATCAAGAAC
GAAGACATCAACAGCCCTAACTTGGGAGAGACGGTATCTGAGAAGGCAA
AAGAAGCTAAGGAAGCGGCTAAACGCAAAGCAGGAGATGCTAAAGAGAA
GTTGGCGGAGACAGTTGAGACGGCGAAAGAGAAGGCGAGCGATATGACG
AGTGCAGCTAAGGAGAAGGCGGAGAAGTTGAAGGAGGAAGCAGAGAGA
GAGAGTAAGAGTGCGAAGGAGAAAATTAAAGAAAGTTATGAGACTGCAA
AATCAAAAGCCGATGAGACTTTAGAGTCCGCGAAAGATAAGGCGTCGCA
GAGTTACGACTCAGCTGCGCGTAAATCGGAGGAAGCTAAAGATACCGCGT
CTCACAAGTCAAAACGTGTTAAAGAGAGCTTGACCGACGATGATGCTGAG
CTCTGA

Figure 9B

SEQ ID NO:22, Amino acid sequence of the open reading frame of Pk1 14

MGLERKVYGLVMVSLVLMAIATMCCVQATIEEEAAKDESWTDWAKEKIGL
KHEDNIQPTHTTTTVQDDAWRASQKAEDAKEAAKRKAEEAVGAAKEKAGS
AYETAKSKVEEGLASVKDKASQSYDSAGQVKDDVSHKSKQVKDSLSGDEND
ESWTGWAKEKIGIKNEDINSPNLGETVSEKAKEAKEAAKRKAGDAKEKLAET
VETAKEKASDMTSAAKEKAEKLKEEAERESKSAKEKIKESYETAKSKADETL
ESAKDKASQSYDSAARKSEEAKDTASHKSKRVKESLTDDDAEL

Figure 10A

SEQ ID NO:23, Nucleotide sequence of the open reading frame of Pk1 16

ATGGCGACTCAATTCAGCGCTTCTGTCTCATTGCAAACTTCTTGTCTGGCA
ACAACAAGGATTAGTTTCCAAAAGCCAGCTTTGATTTCCAACCATGGAAA
GACTAATCTATCCTTCAACCTCCGCCGTTCAATCCCATCTCGCCGCCTCTCT
GTTTCTTGCGCGGCAAAACAAGAGACGATAGAGAAGTGTCTGCTATAGT
TAAGAAGCAACTATCACTTACACCGGATAAAAAGTCGTTGCAGAAACCA
AATTTGCTGACCTTGGAGCAGATTCTCTCGACACGGTTGAGATAGTAATG
GGTTTAGAGGAAGAGTTTAACATCCAAATGGCCGAAGAGAAAGCACAGA
AGATTGCCACAGTTGAGCAAGCTGCTGAACTCATTGAAGAGCTCATCAAC
GAGAAGAAGTAA

Figure 10B

SEQ ID NO:24, Amino acid sequence of the open reading frame of Pk1 16

MATQFSASVSLQTSCLATTRISFQKPALISNHGKTNLSFNLRRSIPSRRLSVSCA
AKQETIEKVSAIVKKQLSLTPDKKVVAETKFADLGADSLDTVEIVMGLEEEFN
IQMAEEKAQKIATVEQAAELIEELINEKK

Figure 11A

SEQ ID NO:25, Nucleotide sequence of the open reading frame of Pk117

ATGCCGGCTACTAGAGTGTTAACTGCAGCGACGGCCGTGACCCAAACCAC
CTCCTGTTTCCTCGCCAAGCAAGCTTTCACTCTTCCGGCGAAGAAATCCTG
CGGCGGATTTGGTGGTCTCTGCTTCAGCAGAAGAGCTTTGGTGTTGAAATC
TAAGAGACCTTTCTCCTGCAGTGCCATTTACAATCCTCAGGTTAAGGTTCA
AGAAGAAGGTCCGGCCGAATCCCTAGATTATCGAGTTTTCTTCCTCGATGG
TTCTGGAAAGAAGGTTTCTCCATGGCATGATATACCATTGACCTTAGGCGA
TGGAGTTTTCAACTTTATAGTTGAAATACCTAAAGAGTCAAAAGCAAAAA
TGGAGGTTGCTACTGATGAAGATTTCACTCCTATTAAGCAGGATACTAAG
AAGGGGAAGCTCAGATATTATCCGTATAACATTAACTGGAACTATGGGTT
GCTTCCTCAAACATGGAAGATCCATCTCATGCAAATTCTGAAGTTGAAG
GATGTTTTGGGGATAATGATCCAGTTGATGTTGTTGAGATTGGTGAAACAC
AAAGGAAGATAGGCGATATTCTAAAGATAAAGCCTTTAGCTGCTTTAGCT
ATGATTGATGAAGGTGAGCTAGACTGGAAGATTGTTGCCATTTCTTTGGAT
GACCCAAAAGCTCATCTTGTGAATGATGTTGAAGATGTTGAGAAACATTT
CCCGGGTACACTAACAGCCATTAGAGACTGGTTTAGAGACTACAAGATCC
CAGATGGAAAGCCTGCTAACAGATTTGGTCTTGGAGACAAACCAGCAAAC
AAAGACTATGCTTTGAAGATCATCCAAGAAACAAATGAATCATGGGCTAA
ACTTGTGAAGAGATCAGTTGATGCTGGAGTCCTTTCACTTTACTGA

Figure 11B

SEQ ID NO:26, Amino acid sequence of the open reading frame of Pk117

MPATRVLTAATAVTQTTSCFLAKQAFTLPAKKSCGGFGGLCFSRRALVLKSK
RPFSCSAIYNPQVKVQEEGPAESLDYRVFFLDGSGKKVSPWHDIPLTLGDGVF
NFIVEIPKESKAKMEVATDEDFTPIKQDTKKGKLRYYPYNINWNYGLLPQTW
EDPSHANSEVEGCFGDNDPVDVVEIGETQRKIGDILKIKPLAALAMIDEGELD
WKIVAISLDDPKAHLVNDVEDVEKHFPGTLTAIRDWFRDYKIPDGKPANRFG
LGDKPANKDYALKIIQETNESWAKLVKRSVDAGVLSLY

Figure 12A

SEQ ID NO:27, Nucleotide sequence of the open reading frame of PK118

ATGGCGTCTTTCTTTGATCTCGTATACATAAGCTGGATTGGTTTCTTAAAC
AAATTCCTCTCCTTTTGGGTCTTCTGGGTTGCCTTGTAAGATATGTAGCCC
AGGGAAGGGGATATTGCAGTCCCACCAGCTGATTGATGAGTTCCTTAAG
ACTGTGAAAGTTGATGGAACATTAGAAGATCTTAACAAAAGTCCATTCAT
GAAAGTTCTGCAGGAAGCCATAGTTTTGCCTCCATTTGTTGCTTTGGCTAT
ACGTCCCAGACCTGGTGTTAGGGAATATGTCCGTGTGAATGTGTATGAGC
TGAGCGTAGATC

FIGURE 12A CONTINUED

ATTTAACTGTTTCTGAATATCTTCGGTTTAAGGAAGAGCTCGTTAATGGCC
ATGCCAATGGAGATTATCTCCTTGAACTTGATTTTGAACCTTTCAATGCAA
CATTGCCTCGCCCAACTCGTTCATCATCCATTGGGAATGGGGTTCAGTTCC
TCAATCGTCACCTCTCTTCAATTATGTTCCGTAACAAAGAAAGCATGGAGC
CTTTGCTTGAGTTTCTCCGCACTCACAAACATGATGGCCGTCCTATGATGC
TGAATGATCGAATACAGAATATCCCCATACTTCAGGGAGCTTTGGCAAGA
GCAGAGGAGTTCCTTTCTAAACTTCCTCTGGCAACACCATACTCTGAATTC
GAATTTGAACTACAAGGGATGGGATTTGAAGGGGATGGGGTGACACAG
CACAGAAGGTTTCAGAAATGGTGCATCTTCTTCTGGACATACTCCAGGCA
CCTGATCCTTCTGTCTTGGAGACGTTTCTAGGAAGGATTCCTATGGTGTTC
AATGTTGTGATTTTGTCTCCGCATGGTTACTTTGGCCAAGCCAATGTCTTG
GGTCTGCCTGATACTGGTGGACAGGTTGTCTACATTCTTGATCAAGTACGT
GCATTGGAAAATGAGATGCTCCTTAGGATACAGAAGCAAGGACTGGAAGT
TATTCCAAAGATTCTCATTGTAACAAGACTGCTACCCGAAGCAAAGGGAA
CAACGTGCAACCAGAGGTTAGAAAGAGTTAGTGGTACAGAACACGCACA
CATTCTGCGAATACCATTTAGGACTGAAAAGGGAATTCTTCGCAAGTGGA
TCTCAAGGTTTGATGTCTGGCCATACCTGGAGACTTTTGCAGAGGATGCAT
CAAATGAAATTTCTGCGGAGTTGCAGGGTGTACCAAATCTCATCATTGGC
AACTACAGTGATGGAAATCTCGTTGCTTCTTTGTTAGCTAGTAAGCTAGGT
GTGATACAGTGTAATATTGCTCATGCTTTAGAGAAAACCAAGTACCCCGA
GTCTGACATTTACTGGAGAAACCATGAAGATAAGTATCACTTTTCAAGTC
AGTTCACTGCAGATCTAATTGCCATGAATAATGCCGATTTCATCATCACCA
GCACATACCAAGAGATTGCGGGAAGCAAGAACAATGTTGGGCAATACGA
GAGCCACACAGCTTTCACTATGCCTGGTCTTTACCGAGTTGTTCATGGAAT
TGATGTCTTTGATCCTAAGTTTAATATAGTCTCTCCAGGAGCTGATATGAC
CATATACTTTCCATATTCTGACAAGGAAAGAAGACTCACTGCCCTTCATGA
GTCAATTGAAGAACTCCTCTTTAGTGCCGAACAGAATGATGAGCATGTTG
GTTTACTGAGCGACCAATCGAAGCCAATCATCTTCTATGGCAAGACTTG
ACAGGGTGAAAAACTTGACTGGGCTAGTTGAATGCTATGCCAAGAATAGC
AAGCTTAGAGAGCTTGCAAATCTTGTTATAGTCGGTGGCTACATCGATGA
GAATCAGTCCAGGGATAGAGAGGAAATGGCTGAGATACAAAAGATGCAC
AGCCTGATTGAGCAGTATGATTTACACGGTGAGTTTAGGTGGATAGCTGC
TCAAATGAACCGTGCTCGAAATGGTGAGCTTACCGTTATATCGCAGACA
CAAAAGGTGTTTTTGTTCAGCCTGCTTTCTATGAAGCATTTGGGCTTACGG
TTGTGGAATCAATGACTTGTGCACTCCAACGTTTGCTACCTGTCATGGTG
GACCCGCAGAGATTATCGAAAACGGAGTTTCTGGGTTCCACATTGACCCA
TATCATCCAGACCAGGTTGCAGCTACCTTGGTCAGCTTCTTTGAGACCTGT
AACACCAATCCAAATCATTGGGTTAAAATCTCTGAAGGAGGGCTCAAGCG
AATCTATGAAAGGTACACATGGAAGAAGTACTCAGAGAGACTGCTTACCC
TGGCTGGAGTCTATGCATTCTGGAAACATGTGTCTAAGCTCGAAAGGAGA
GAAACACGACGTTACCTAGAGATGTTTACTCATTGAAATTTCGTGATTTG
GCCAATTCAATCCCGCTGGCAACAGATGAGAACTGA

Figure 12B

SEQ ID NO:28, Amino acid sequence of the open reading frame of PK118

MASFFDLVYISWIGFLNKFLSFWVFWVCLVRYVAQGKGILQSHQLIDEFLKTV
KVDGTLEDLNKSPFMKVLQEAIVLPPFVALAIRPRPGVREYVRVNVYELSVD
HLTVSEYLRFKEELVNGHANGDYLLELDFEPFNATLPRPTRSSSIGNGVQFLN
RHLSSIMFRNKESMEPLLEFLRTHKHDGRPMMLNDRIQNIPILQGALARAEEF
LSKLPLATPYSEFEFELQGMGFERGWGDTAQKVSEMVHLLLDILQAPDPSVL
ETFLGRIPMVFNVVILSPHGYFGQANVLGLPDTGGQVVYILDQVRALENEML
LRIQKQGLEVIPKILIVTRLLPEAKGTTCNQRLERVSGTEHAHILRIPFRTEKGIL
RKWISRFDVWPYLETFAEDASNEISAELQGVPNLIIGNYSDGNLVASLLASKL
GVIQCNIAHALEKTKYPESDIYWRNHEDKYHFSSQFTADLIAMNNADFIITSTY
QEIAGSKNNVGQYESHTAFTMPGLYRVVHGIDVFDPKFNIVSPGADMTIYFPY
SDKERRLTALHESIEELLFSAEQNDEHVGLLSDQSKPIIFSMARLDRVKNLTGL
VECYAKNSKLRELANLVIVGGYIDENQSRDREEMAEIQKMHSLIEQYDLHGE
FRWIAAQMNRARNGELYRYIADTKGVFVQPAFYEAFGLTVVESMTCALPTFA
TCHGGPAEIIENGVSGFHIDPYHPDQVAATLVSFFETCNTNPNHWVKISEGGL
KRIYERYTWKKYSERLLTLAGVYAFWKHVSKLERRETRRYLEMFYSLKFRD
LANSIPLATDEN

Figure 12C

SEQ ID NO:29, Nucleotide sequence of the open reading frame of PK118-1

ATGTGTGTTGTGATTGGTCTCAAGTCATGGGTAATGGTTTTGGTTGTTATC
TTTATTAGATATGTAGCCCAGGGAAAGGGGATATTGCAGTCCCACCAGCT
GATTGATGAGTTCCTTAAGACTGTGAAAGTTGATGGAACATTAGAAGATC
TTAACAAAAGTCCATTCATGAAAGTTCTGCAGTCTGCAGAGGAAGCCATA
GTTTTGCCTCCATTTGTTGCTTTGGCTATACGTCCCAGACCTGGTGTTAGG
GAATATGTCCGTGTGAATGTGTATGAGCTGAGCGTAGATCATTTAACTGTT
TCTGAATATCTTCGGTTTAAGGAAGAGCTCGTTAATGGCCATGCCAATGG
AGATTATCTCCTTGAACTTGATTTGAACCTTTCAATGCAACATTGCCTCG
CCCAACTCGTTCATCATCCATTGGGAATGGGGTTCAGTTCCTCAATCGTCA
CCTCTCTTCAATTATGTTCCGTAACAAAGAAAGCATGGAGCCTTTGCTTGA
GTTTCTCCGCACTCACAAACATGATGGCCGTCCTATGATGCTGAATGATCG
AATACAGAATATCCCCATACTTCAGGGAGCTTTGGCAAGAGCAGAGGAGT
TCCTTTCTAAACTTCCTCTGGCAACACCATACTCTGAATTCGAATTTGAAC
TACAAGGGATGGGATTTGAAGGGGATGGGTGACACAGCACAGAAGGT
TTCAGAAATGGTGCATCTTCTTCTGGACATACTCCAGGCACCTGATCCTTC
TGTCTTGGAGACGTTTCTAGGAAGGATTCCTATGGTGTTCAATGTTGTGAT
TTTGTCTCCGCATGGTTACTTTGGCCAAGCCAATGTCTTGGGTCTGCCTGA
TACTGGTGGACAGGTTGTCTACATTCTTGATCAAGTACGTGCATTGGAAAA
TGAGATGCTCCTTAGGATACAGAAGCAAGGACTGGAAGTTATTCCAAAGA
TTCTCATTGTAACAAGACTGCTACCCGAAGCAAAGGGAACAACGTGCAAC
CAGAGGTTAGAAAGAGTTAGTGGTACAGAACACGCACACA

FIGURE 12C CONTINUED

```
TTCTGCGAATACCATTTAGGACTGAAAAGGGAATTCTTCGCAAGTGGATC
TCAAGGTTTGATGTCTGGCCATACCTGGAGACTTTTGCAGAGGATGCATCA
AATGAAATTTCTGCGGAGTTGCAGGGTGTACCAAATCTCATCATTGGCAA
CTACAGTGATGGAAATCTCGTTGCTTCTTTGTTAGCTAGTAAGCTAGGTGT
GATACAGTGTAATATTGCTCATGCTTTAGAGAAAACCAAGTACCCCGAGT
CTGACATTTACTGGAGAAACCATGAAGATAAGTATCACTTTTCAAGTCAG
TTCACTGCAGATCTAATTGCCATGAATAATGCCGATTTCATCATCACCAGC
ACATACCAAGAGATTGCGGGAAGCAAGAACAATGTTGGGCAATACGAGA
GCCACACAGCTTTCACTATGCCTGGTCTTTACCGAGTTGTTCATGGAATTG
ATGTCTTTGATCCTAAGTTTAATATGGTCTCTCCAGGAGCTGATATGACCA
TATACTTTCCATATTCCGACAAGGAAAGAAGACTCACTGCCCTTCATGAGT
CAATTGAAGAACTCCTCTTTAGTGCCGAACAGAATGATGAGCATGTTGGT
TTACTGAGCGACCAATCGAAGCCAATCATCTTCTCTATGGCAAGACTTGAC
AGGGTGAAAAACTTGACTGGGCTAGTTGAATGCTATGCCAAGAATAGCAA
GCTTAGAGAGCTTGCAAATCTTGTTATAGTCGGTGGCTACATCGATGAGA
ATCAGTCCAGGGATAGAGAGGAAATGGCTGAGATACAAAGATGCACAG
CCTGATTGAGCAGTATGATTTACACGGTGAGTTTAGGTGGATAGCTGCTCA
AATGAACCGTGCTCGAAATGGTGAGCTTTACCGTTATATCGCAGACACAA
AAGGTGTTTTTGTTCAGCCTGCTTTCTATGAAGCATTTGGGCTTACGGTTG
TGGAATCAATGACTTGTGCACTCCAACGTTTGCTACCTGTCATGGTGGAC
CCGCAGAGATTATCGAAAACGGAGTTTCTGGGTTCCACATTGACCCATAT
CATCCAGACCAGGTTGCAGCTACCTTGGTCAGCTTCTTTGAGACCTGTAAC
ACCAATCCAAATCATTGGGTTAAAATCTCTGAAGGAGGGCTCAAGCGAAT
CTATGAAAGGTACACATGGAAGAAGTACTCAGAGAGACTGCTTACCCTGG
CTGGAGTCTATGCATTCTGGAAACATGTGTCTAAGCTCGAAAGGAGAGAA
ACACGACGTTACCTAGAGATGTTTTACTCATTGAAATTTCGTGATTTGGCC
AATTCAATCCCGCTGGCAACAGATGAGAACTGA
```

Figure 12D

SEQ ID NO:30, Amino acid sequence of the open reading frame of PK118-1

MCVVIGLKSWVMVLVVIFIRYVAQGKGILQSHQLIDEFLKTVKVDGTLEDLN
KSPFMKVLQSAEEAIVLPPFVALAIRPRPGVREYVRVNVYELSVDHLTVSEYL
RFKEELVNGHANGDYLLELDFEPFNATLPRPTRSSSIGNGVQFLNRIHLSSIMFR
NKESMEPLLEFLRTHKHDGRPMMLNDRIQNIPILQGALARAEEFLSKLPLATP
YSEFEFELQGMGFERGWGDTAQKVSEMVHLLLDILQAPDPSVLETFLGRIPM
VFNVVILSPHGYFGQANVLGLPDTGGQVVYILDQVRALENEMLLRIQKQGLE
VIPKILIVTRLLPEAKGTTCNQRLERVSGTEHAHILRIPFRTEKGILRKWISRFD
VWPYLETFAEDASNEISAELQGVPNLIIGNYSDGNLVASLLASKLGVIQCNIAH
ALEKTKYPESDIYWRNHEDKYHFSSQFTADLIAMNNADFIITSTYQEIAGSKN
NVGQYESHTAFTMPGLYRVVHGIDVFDPKFNMVSPGADMTIYFPYSDKERRL
TALHESIEELLFSAEQNDEHVGLLSDQSKPIIFSMARLDRVKNLTGLVECYAK
NSKLRELANLVIVGGYIDENQSRDREEMAEIQKMHSLIEQYDLHGEFRWIAA
QMNRARNGELYRYIADTKGVFVQPAF

FIGURE 12D CONTINUED

YEAFGLTVVESMTCALPTFATCHGGPAEHENGVSGFHIDPYHPDQVAATLVS
FFETCNTNPNHWVKISEGGLKRIYERYTWKKYSERLLTLAGVYAFWKHVSKL
ERRETRRYLEMFYSLKFRDLANSIPLATDEN

Figure 13A

SEQ ID NO:31, Nucleotide sequence of the open reading frame of PK120

ATGTCGAACATAGACATAGAAGGGATCTTGAAGGAGCTACCTAATGATGG
GAGGATCCCAAAGACGAAGATAGTTTGCACATTAGGACCAGCTTCTCGCA
CTGTTTCCATGATCGAAAAGCTTTTGAAAGCCGGTATGAATGTGGCTCGCT
TCAACTTCTCACATGGAAGCCATGAATACCATCAAGAGACACTCGACAAC
CTCCGCTCTGCTATGCATAATACCGGCATTCTCGCTGCTGTCATGCTTGAT
ACTAAGGGGCCTGAGATTCGTACTGGTTTCTTGAAAGATGGGAACCCTAT
ACAACTGAAGGAAGGTCAAGAGATTACTATAACCACTGATTATGACATTC
AAGGAGACGAATCAACGATATCCATGAGCTATAAAAGCTGCCTTTGGAT
GTGAAGCCCGGAAACACCATACTCTGTGCAGATGGAAGCATAAGTCTAGC
TGTCTTGTCATGTGATCCTGAGTCTGGAACTGTTAGGTGCCGGTGTGAAAA
CTCGGCGATGCTTGGTGAAAGAAGAATGTGAATCTTCCTGGCGTTGTTGT
TGATCTTCCCACTTTGACAGATAAGGATATTGAAGATATTCTCGGTTGGGG
TGTTCCGAACAGCATTGATATGATTGCTCTTTCGTTTGTCCGTAAAGGTTC
GGATCTTGTTAATGTCCGCAAGGTTCTTGGATCTCATGCTAAAAGCATAAT
GCTCATGTCAAAGGTTGAGAACCAGGAAGGTGTGATTAACTTTGATGAGA
TCTTGCGTGAAACAGATGCGTTCATGGTTGCCCGTGGTGATCTCGGGATGG
AGATTCCGATAGAGAAGATCTTCTTGGCTCAAAAGTTGATGATCTACAAG
TGTAACCTTGCGGGTAAACCGGTGGTCACAGCCACTCAGATGCTGGAGTC
AATGATCAAATCACCTCGGCCAACCCGAGCTGAAGCCACAGATGTTGCAA
ATGCTGTTCTTGATGGTACTGACTGTGTGATGCTTAGCGGTGAGAGTGCAG
CAGGAGCTTATCCGGAAATAGCTGTGAAAGTCATGGCTAAGATCTGCATT
GAAGCCGAATCCTCGCTTGATTACAACACAATCTTTAAAGAGATGATCCG
AGCAACTCCACTTCCAATGAGCCCACTCGAGAGTCTTGCATCATCCGCTGT
ACGGACTGCTAACAAAGCGAGGGCAAAACTCATCATTGTGTTGACACGTG
GAGGTTCAACTGCTAATCTCGTGGCTAAATACAGACCGGCTGTTCCGATTC
TGTCAGTGGTTGTCCCGGTTATGACCACTGATTCCTTTGACTGGTCTTGTA
GTGACGAGTCACCTGCAAGGCATAGTCTGATATACAGAGGTCTAATCCCT
ATGTTGGCTGAAGGATCTGCAAAGGCAACAGATAGTGAAGCCACCGAAGT
TATCATTGAAGCTGCTCTGAAGTCGGCTACTCAGAGAGGACTGTGCAACC
GTGGTGATGCAATCGTGGCGCTGCACCGTATTGGAGCTGCCTCAGTTATTA
AGATCTGTGTGGTTAAGTGA

Figure 13B

SEQ ID NO:32, Amino acid sequence of the open reading frame of PK120

MSNIDIEGILKELPNDGRIPKTKIVCTLGPASRTVSMIEKLLKAGMNVARFNFS
HGSHEYHQETLDNLRSAMHNTGILAAVMLDTKGPEIRTGFLKDGNPIQLKEG
QEITITTDYDIQGDESTISMSYKKLPLDVKPGNTILCADGSISLAVLSCDPESGT
VRCRCENSAMLGERKNVNLPGVVVDLPTLTDKDIEDILGWGVPNSIDMIALSF
VRKGSDLVNVRKVLGSHAKSIMLMSKVENQEGVINFDEILRETDAFMVARG
DLGMEIPIEKIFLAQKLMIYKCNLAGKPVVTATQMLESMIKSPRPTRAEATDV
ANAVLDGTDCVMLSGESAAGAYPEIAVKVMAKICIEAESSLDYNTIFKEMIRA
TPLPMSPLESLASSAVRTANKARAKLIIVLTRGGSTANLVAKYRPAVPILSVVV
PVMTTDSFDWSCSDESPARHSLIYRGLIPMLAEGSAKATDSEATEVIIEAALKS
ATQRGLCNRGDAIVALHRIGAASVIKICVVK

SUGAR AND LIPID METABOLISM REGULATORS IN PLANTS III

RELATED APPLICATIONS

This application is a divisional of U.S. patent application Ser. No. 12/631,262, filed Dec. 4, 2009, which is a divisional of U.S. patent application Ser. No. 11/520,850, filed Sep. 13, 2006, which is a divisional of U.S. patent application Ser. No. 10/217,939, filed Aug. 12, 2002, now U.S. Pat. No. 7,135,618, which claims benefit to U.S. Provisional Application No. 60/311,414 filed Aug. 10, 2001. The entire contents of each of these applications are hereby incorporated by reference herein.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing__13987__00132_US. The size of the text file is 103 KB, and the text file was created on Nov. 9, 2010.

FIELD OF THE INVENTION

This invention relates generally to nucleic acid sequences encoding proteins that are related to the presence of seed storage compounds in plants. More specifically, the present invention relates to nucleic acid sequences encoding sugar and lipid metabolism regulator proteins and the use of these sequences in transgenic plants. The invention further relates to methods of applying these novel plant polypeptides to the identification and stimulation of plant growth and/or to the increase of yield of seed storage compounds.

BACKGROUND

The study and genetic manipulation of plants has a long history that began even before the framed studies of Gregor Mendel. In perfecting this science, scientists have accomplished modification of particular traits in plants ranging from potato tubers having increased starch content to oilseed plants such as canola and sunflower having increased or altered fatty acid content. With the increased consumption and use of plant oils, the modification of seed oil content and seed oil levels has become increasingly widespread (e.g. Töpfer et al. 1995, Science 268:681-686). Manipulation of biosynthetic pathways in transgenic plants provides a number of opportunities for molecular biologists and plant biochemists to affect plant metabolism giving rise to the production of specific higher-value products. The seed oil production or composition has been altered in numerous traditional oilseed plants such as soybean (U.S. Pat. No. 5,955,650), canola (U.S. Pat. No. 5,955,650), sunflower (U.S. Pat. No. 6,084,164) and rapeseed (Töpfer et al. 1995, Science 268:681-686), and non-traditional oil seed plants such as tobacco (Cahoon et al. 1992, Proc. Natl. Acad. Sci. USA 89:11184-11188).

Plant seed oils comprise both neutral and polar lipids (see Table 1). The neutral lipids contain primarily triacylglycerol, which is the main storage lipid that accumulates in oil bodies in seeds. The polar lipids are mainly found in the various membranes of the seed cells, e.g. the endoplasmic reticulum, microsomal membranes and the cell membrane. The neutral and polar lipids contain several common fatty acids (see Table 2) and a range of less common fatty acids. The fatty acid composition of membrane lipids is highly regulated and only a select number of fatty acids are found in membrane lipids. On the other hand, a large number of unusual fatty acids can be incorporated into the neutral storage lipids in seeds of many plant species (Van de Loo F. J. et al. 1993, Unusual Fatty Acids in Lipid Metabolism in Plants pp. 91-126, editor TS Moore Jr. CRC Press; Millar et al. 2000, Trends Plant Sci. 5:95-101).

TABLE 1

Plant Lipid Classes

| | |
|---|---|
| Neutral Lipids | Triacylglycerol (TAG) |
| | Diacylglycerol (DAG) |
| | Monoacylglycerol (MAG) |
| Polar Lipids | Monogalactosyldiacylglycerol (MGDG) |
| | Digalactosyldiacylglycerol (DGDG) |
| | Phosphatidylglycerol (PG) |
| | Phosphatidylcholine (PC) |
| | Phosphatidylethanolamine (PE) |
| | Phosphatidylinositol (PI) |
| | Phosphatidylserine (PS) |
| | Sulfoquinovosyldiacylglycerol |

TABLE 2

Common Plant Fatty Acids

| | |
|---|---|
| 16:0 | Palmitic acid |
| 16:1 | Palmitoleic acid |
| 16:3 | Palmitolenic acid |
| 18:0 | Stearic acid |
| 18:1 | Oleic acid |
| 18:2 | Linoleic acid |
| 18:3 | Linolenic acid |
| γ-18:3 | Gamma-linolenic acid * |
| 20:0 | Arachidic acid |
| 22:6 | Docosahexanoic acid (DHA) * |
| 20:2 | Eicosadienoic acid |
| 20:4 | Arachidonic acid (AA) * |
| 20:5 | Eicosapentaenoic acid (EPA) * |
| 22:1 | Erucic acid |

These fatty acids do not normally occur in plant seed oils, but their production in transgenic plant seed oil is of importance in plant biotechnology.

Lipids are synthesized from fatty acids and their synthesis may be divided into two parts: the prokaryotic pathway and the eukaryotic pathway (Browse et al. 1986, Biochemical J. 235:25-31; Ohlrogge & Browse 1995, Plant Cell 7:957-970). The prokaryotic pathway is located in plastids that are the primary site of fatty acid biosynthesis. Fatty acid synthesis begins with the conversion of acetyl-CoA to malonyl-CoA by acetyl-CoA carboxylase (ACCase). Malonyl-CoA is converted to malonyl-acyl carrier protein (ACP) by the malonyl-CoA:ACP transacylase. The enzyme beta-keto-acyl-ACP-synthase III (KAS III) catalyzes a condensation reaction in which the acyl group from acetyl-CoA is transferred to malonyl-ACP to form 3-ketobutyryl-ACP. In a subsequent series of condensation, reduction and dehydration reactions the nascent fatty acid chain on the ACP cofactor is elongated by the step-by-step addition (condensation) of two carbon atoms donated by malonyl-ACP until a 16- or 18-carbon saturated fatty acid chain is formed. The plastidial delta-9 acyl-ACP desaturase introduces the first unsaturated double bond into the fatty acid. Thioesterases cleave the fatty acids from the ACP cofactor and free fatty acids are exported to the cytoplasm where they participate as fatty acyl-CoA esters in the eukaryotic pathway. In this pathway the fatty acids are esterified by glycerol-3-phosphate acyltransferase and lysophosphatidic acid acyltransferase to the sn-1 and sn-2 positions of glycerol-3-phosphate, respectively, to yield phosphatidic acid (PA). The PA is the precursor for other polar and neutral lipids, the latter being formed in the Kennedy pathway (Voelker 1996, Genetic Engineering ed.:Setlow 18:111-113; Shanklin & Cahoon 1998, Annu Rev. Plant Physiol. Plant Mol. Biol. 49:611-641; Frentzen 1998, Lipids 100:161-166; Millar et al. 2000, Trends Plant Sci. 5:95-101).

Storage lipids in seeds are synthesized from carbohydrate-derived precursors. Plants have a complete glycolytic pathway in the cytosol (Plaxton 1996, Annu. Rev. Plant Physiol. Plant Mol. Biol. 47:185-214) and it has been shown that a complete pathway also exists in the plastids of rapeseeds (Kang & Rawsthorne 1994, Plant J. 6:795-805). Sucrose is the primary source of carbon and energy, transported from the leaves into the developing seeds. During the storage phase of seeds, sucrose is converted in the cytosol to provide the metabolic precursors glucose-6-phosphate and pyruvate. These are transported into the plastids and converted into acetyl-CoA that serves as the primary precursor for the synthesis of fatty acids. Acetyl-CoA in the plastids is the central precursor for lipid biosynthesis. Acetyl-CoA can be formed in the plastids by different reactions and the exact contribution of each reaction is still being debated (Ohlrogge & Browse 1995, Plant Cell 7:957-970). It is however accepted that a large part of the acetyl-CoA is derived from glucose-6-phospate and pyruvate that are imported from the cytoplasm into the plastids. Sucrose is produced in the source organs (leaves, or anywhere that photosynthesis occurs) and is transported to the developing seeds that are also termed sink organs. In the developing seeds, the sucrose is the precursor for all the storage compounds, i.e. starch, lipids and partly the seed storage proteins. Therefore, it is clear that carbohydrate metabolism in which sucrose plays a central role is very important to the accumulation of seed storage compounds.

Although lipid and fatty acid content of seed oil can be modified by the traditional methods of plant breeding, the advent of recombinant DNA technology has allowed for easier manipulation of the seed oil content of a plant, and in some cases, has allowed for the alteration of seed oils in ways that could not be accomplished by breeding alone (see, e.g., Töpfer et al. 1995, Science 268:681-686). For example, introduction of a $\Delta^{12}$-hydroxylase nucleic acid sequence into transgenic tobacco resulted in the introduction of a novel fatty acid, ricinoleic acid, into the tobacco seed oil (Van de Loo et al. 1995, Proc. Natl. Acad. Sci. USA 92:6743-6747). Tobacco plants have also been engineered to produce low levels of petroselinic acid by the introduction and expression of an acyl-ACP desaturase from coriander (Cahoon et al. 1992, Proc. Natl. Acad. Sci. USA 89:11184-11188).

The modification of seed oil content in plants has significant medical, nutritional and economic ramifications. With regard to the medical ramifications, the long chain fatty acids (C18 and longer) found in many seed oils have been linked to reductions in hypercholesterolemia and other clinical disorders related to coronary heart disease (Brenner 1976, Adv. Exp. Med. Biol. 83:85-101). Therefore, consumption of a plant having increased levels of these types of fatty acids may reduce the risk of heart disease. Enhanced levels of seed oil content also increase large-scale production of seed oils and thereby reduce the cost of these oils.

In order to increase or alter the levels of compounds such as seed oils in plants, nucleic acid sequences and proteins regulating lipid and fatty acid metabolism must be identified. As mentioned earlier, several desaturase nucleic acids such as the $\Delta^6$-desaturase nucleic acid, $\Delta^{12}$-desaturase nucleic acid and acyl-ACP desaturase nucleic acid have been cloned and demonstrated to encode enzymes required for fatty acid synthesis in various plant species. Oleosin nucleic acid sequences from such different species as *Brassica*, soybean, carrot, pine and *Arabidopsis thaliana* have also been cloned and determined to encode proteins associated with the phospholipid monolayer membrane of oil bodies in those plants.

It has also been determined that two phytohormones, gibberellic acid (GA) and absisic acid (ABA), are involved in overall regulatory processes in seed development (e.g. Ritchie & Gilroy 1998, Plant Physiol. 116:765-776; Arenas-Huertero et al. 2000, Genes Dev. 14:2085-2096). Both the GA and ABA pathways are affected by okadaic acid, a protein phosphatase inhibitor (Kuo et al. 1996, Plant Cell. 8:259-269). The regulation of protein phosphorylation by kinases and phosphatases is accepted as a universal mechanism of cellular control (Cohen 1992, Trends Biochem. Sci. 17:408-413. Likewise, the plant hormones ethylene (e.g. Zhou et al. 1998, Proc. Natl. Acad. Sci. USA 95:10294-10299; Beaudoin et al. 2000, Plant Cell 2000:1103-1115) and auxin (e.g. Colon-Carmona et al. 2000, Plant Physiol. 124:1728-1738) are involved in controlling plant development as well.

Although several compounds are known that generally affect plant and seed development, there is a clear need to specifically identify factors that are more specific for the developmental regulation of storage compound accumulation and to identify genes which have the capacity to confer altered or increased oil production to its host plant and to other plant species. This invention discloses a large number of nucleic acid sequences from *Arabidopsis thaliana*. These nucleic acid sequences can be used to alter or increase the levels of seed storage compounds such as proteins, sugars and oils, in plants, including transgenic plants, such as rapeseed, canola, linseed, soybean, sunflower maize, oat, rye, barley, wheat, pepper, tagetes, cotton, oil palm, coconut palm, flax, castor and peanut, which are oilseed plants containing high amounts of lipid compounds.

SUMMARY OF THE INVENTION

The present invention provides novel isolated nucleic acid and amino acid sequences associated with the metabolism of seed storage compounds in plants.

The present invention also provides an isolated nucleic acid from *Arabidopsis* encoding a Lipid Metabolism Protein (LMP), or a portion thereof. These sequences may be used to modify or increase lipids and fatty acids, cofactors and enzymes in microorganisms and plants.

*Arabidopsis* plants are known to produce considerable amounts of fatty acids like linoleic and linolenic acid (see, e.g., Table 2) and for their close similarity in many aspects (gene homology etc.) to the oil crop plant *Brassica*. Therefore nucleic acid molecules originating from a plant like *Arabidopsis thaliana* are especially suited to modify the lipid and fatty acid metabolism in a host, especially in microorganisms and plants. Furthermore, nucleic acids from the plant *Arabidopsis thaliana* can be used to identify those DNA sequences and enzymes in other species which are useful to modify the biosynthesis of precursor molecules of fatty acids in the respective organisms.

The present invention further provides an isolated nucleic acid comprising a fragment of at least 15 nucleotides of a nucleic acid from a plant (*Arabidopsis thaliana*) encoding a Lipid Metabolism Protein (LMP), or a portion thereof.

Also provided by the present invention are polypeptides encoded by the nucleic acids, and heterologous polypeptides comprising polypeptides encoded by the nucleic acids, and antibodies to those polypeptides.

Additionally, the present invention relates to and provides the use of LMP nucleic acids in the production of transgenic plants having a modified level of a seed storage compound. A method of producing a transgenic plant with a modified level of a seed storage compound includes the steps of transforming a plant cell with an expression vector comprising a LMP nucleic acid, and generating a plant with a modified level of the seed storage compound from the plant cell. In a preferred embodiment, the plant is an oil producing species selected from the group consisting of rapeseed, canola, linseed, soybean, sunflower, maize, oat, rye, barley, wheat, pepper, tagetes, cotton, oil palm, coconut palm, flax, castor and peanut, for example.

According to the present invention, the compositions and methods described herein can be used to increase or decrease the level of a LMP in a transgenic plant comprising increasing or decreasing the expression of a LMP nucleic acid in the plant. Increased or decreased expression of the LMP nucleic acid can be achieved through in vivo mutagenesis of the LMP nucleic acid. The present invention can also be used to increase or decrease the level of a lipid in a seed oil, to increase or decrease the level of a fatty acid in a seed oil, or to increase or decrease the level of a starch in a seed or plant.

Also included herein is a seed produced by a transgenic plant transformed by a LMP DNA sequence, wherein the seed contains the LMP DNA sequence and wherein the plant is true breeding for a modified level of a seed storage compound. The present invention additionally includes a seed oil produced by the aforementioned seed.

Further provided by the present invention are vectors comprising the nucleic acids, host cells containing the vectors, and descendent plant materials produced by transforming a plant cell with the nucleic acids and/or vectors.

According to the present invention, the compounds, compositions, and methods described herein can be used to increase or decrease the level of a lipid in a seed oil, or to increase or decrease the level of a fatty acid in a seed oil, or to increase or decrease the level of a starch or other carbohydrate in a seed or plant. A method of producing a higher or lower than normal or typical level of storage compound in a transgenic plant, comprises expressing a LMP nucleic acid from *Arabidopsis thaliana* in the transgenic plant, wherein the transgenic plant is *Arabidopsis thaliana* or a species different from *Arabidopsis thaliana*. Also included herein are compositions and methods of the modification of the efficiency of production of a seed storage compound.

Accordingly, it is an object of the present invention to provide novel isolated LMP nucleic acids and isolated LMP amino acid sequences from *Arabidopsis thaliana*, as well as active fragments, analogs and orthologs thereof.

It is another object of the present invention to provide transgenic plants having modified levels of seed storage compounds, and in particular, modified levels of a lipid, a fatty acid or a sugar.

It is a further object of the present invention to provide methods for producing such aforementioned transgenic plants.

It is another object of the present invention to provide seeds and seed oils from such aforementioned transgenic plants.

These and other objects, features and advantages of the present invention will become apparent after a review of the following detailed description of the disclosed embodiments and the appended claims.

BRIEF DESCRIPTION OF THE FIGURES

FIGS. 1A-B: FIG. 1A shows the polynucleotide sequences of the open reading frame of Clone ID NO: AT004002024 from *Arabidopsis thaliana* (SEQ ID NO:1) of the present invention. The polynucleotide sequence contains 648 nucleotides. FIG. 1B shows the deduced amino acid sequence of SEQ ID NO:1 (SEQ ID NO:2) (Clone ID NO: AT004002024) of the present invention. The polypeptide sequence contains 216 amino acids. The standard one-letter abbreviation for amino acids is used to illustrate the deduced amino acid sequence.

FIG. 2A-B: FIG. 2A shows the polynucleotide sequences of the open reading frame of Clone ID NO: AT004004054 from *Arabidopsis thaliana* (SEQ ID NO:3) of the present invention. The polynucleotide sequence contains 720 nucleotides. FIG. 2B shows the deduced amino acid sequence of SEQ ID NO:3 (SEQ ID NO:4) (Clone ID NO: AT004004054) of the present invention. The polypeptide sequence contains 240 amino acids. The standard one-letter abbreviation for amino acids is used to illustrate the deduced amino acid sequence.

FIGS. 3A-B: FIG. 3A shows the polynucleotide sequences of the open reading frame of Clone ID NO: AT004005069 from *Arabidopsis thaliana* (SEQ ID NO:5) of the present invention. The polynucleotide sequence contains 1995 nucleotides. FIG. 3B shows the deduced amino acid sequence of SEQ ID NO:5 (SEQ ID NO:6) (Clone ID NO: AT004005069) of the present invention. The polypeptide sequence contains 665 amino acids. The standard one-letter abbreviation for amino acids is used to illustrate the deduced amino acid sequence.

FIGS. 4A-B: FIG. 4A shows the polynucleotide sequences of the open reading frame of Clone ID NO: AT004009021 from *Arabidopsis thaliana* (SEQ ID NO:7) of the present invention. The polynucleotide sequence contains 1200 nucleotides. FIG. 4B shows the deduced amino acid sequence of SEQ ID NO:7 (SEQ ID NO:8) (Clone ID NO: AT004009021) of the present invention. The polypeptide sequence contains 400 amino acids. The standard one-letter abbreviation for amino acids is used to illustrate the deduced amino acid sequence.

FIGS. 5A-D: FIG. 5A shows the polynucleotide sequences of the open reading frame of Clone ID NO: pk109 from *Arabidopsis thaliana* (SEQ ID NO:9) of the present invention. The polynucleotide sequence contains 1173 nucleotides. FIG. 5B shows the deduced amino acid sequence of SEQ ID NO:9 (SEQ ID NO:10) (Clone ID NO: pk109) of the present invention. The polypeptide sequence contains 391 amino acids. FIG. 5C shows the polynucleotide sequences of the open reading frame of Clone ID NO: pk109-1 from *Arabidopsis thaliana* (SEQ ID NO:11) of the present invention. The polynucleotide sequence contains 843 nucleotides. FIG. 5D shows the deduced amino acid sequence of SEQ ID NO:11 (SEQ ID NO:12) (Clone ID NO: pk109-1) of the present invention. The polypeptide sequence contains 281 amino acids. The standard one-letter abbreviation for amino acids is used to illustrate the deduced amino acid sequence.

FIGS. 6A-B: FIG. 6A shows the polynucleotide sequences of the open reading frame of Clone ID NO: pk110 from *Arabidopsis thaliana* (SEQ ID NO:13) of the present invention. The polynucleotide sequence contains 2013 nucleotides. FIG. 6B shows the deduced amino acid sequence of SEQ ID NO:13 (SEQ ID NO:14) (Clone ID NO: pk110) of the present invention. The polypeptide sequence contains 671 amino acids. The standard one-letter abbreviation for amino acids is used to illustrate the deduced amino acid sequence.

FIGS. 7A-D: FIG. 7A shows the polynucleotide sequences of the open reading frame of Clone ID NO: pk111 from *Arabidopsis thaliana* (SEQ ID NO:15) of the present invention. The polynucleotide sequence contains 2337 nucleotides.

FIG. 7B shows the deduced amino acid sequence of SEQ ID NO:15 (SEQ ID NO:16) (Clone ID NO: pk111) of the present invention. The polypeptide sequence contains 779 amino acids. FIG. 7C shows the polynucleotide sequences of the open reading frame of Clone ID NO: pk111-1 from *Arabidopsis thaliana* (SEQ ID NO:17) of the present invention. The polynucleotide sequence contains 1667 nucleotides. FIG. 7D shows the deduced amino acid sequence of SEQ ID NO:17 (SEQ ID NO:18) (Clone ID NO: pk111-1) of the present invention. The polypeptide sequence contains 557 amino acids. The standard one-letter abbreviation for amino acids is used to illustrate the deduced amino acid sequence.

FIGS. 8A-B: FIG. 8A shows the polynucleotide sequences of the open reading frame of Clone ID NO: pk113 from *Arabidopsis thaliana* (SEQ ID NO:19) of the present invention. The polynucleotide sequence contains 1719 nucleotides. FIG. 8B shows the deduced amino acid sequence of SEQ ID NO:19 (SEQ ID NO:20) (Clone ID NO: pk113) of the present invention. The polypeptide sequence contains 573 amino acids. The standard one-letter abbreviation for amino acids is used to illustrate the deduced amino acid sequence.

FIGS. 9A-B: FIG. 9A shows the polynucleotide sequences of the open reading frame of Clone ID NO: pk114 from *Arabidopsis thaliana* (SEQ ID NO:21) of the present invention. The polynucleotide sequence contains 894 nucleotides. FIG. 9B shows the deduced amino acid sequence of SEQ ID NO:21 (SEQ ID NO:22) (Clone ID NO: pk114) of the present invention. The polypeptide sequence contains 298 amino acids. The standard one-letter abbreviation for amino acids is used to illustrate the deduced amino acid sequence.

FIGS. 10A-B: FIG. 116 shows the polynucleotide sequences of the open reading frame of Clone ID NO: pk116 from *Arabidopsis thaliana* (SEQ ID NO:23) of the present invention. The polynucleotide sequence contains 411 nucleotides. FIG. 10B shows the deduced amino acid sequence of SEQ ID NO:23 (SEQ ID NO:24) (Clone ID NO: pk116) of the present invention. The polypeptide sequence contains 137 amino acids. The standard one-letter abbreviation for amino acids is used to illustrate the deduced amino acid sequence.

FIGS. 11A-B. FIG. 11A shows the polynucleotide sequences of the open reading frame of Clone ID NO: pk117 from *Arabidopsis thaliana* (SEQ ID NO:25) of the present invention. The polynucleotide sequence contains 900 nucleotides. FIG. 11B shows the deduced amino acid sequence of SEQ ID NO:25 (SEQ ID NO:26) (Clone ID NO: pk117) of the present invention. The polypeptide sequence contains 300 amino acids. The standard one-letter abbreviation for amino acids is used to illustrate the deduced amino acid sequence.

FIGS. 12A-D. FIG. 12A shows the polynucleotide sequences of the open reading frame of Clone ID NO: pk118 from *Arabidopsis thaliana* (SEQ ID NO:27) of the present invention. The polynucleotide sequence contains 2415 nucleotides. FIG. 12B shows the deduced amino acid sequence of SEQ ID NO:27 (SEQ ID NO:28) (Clone ID NO: pk118) of the present invention. The polypeptide sequence contains 805 amino acids. FIG. 12C shows the polynucleotide sequences of the open reading frame of Clone ID NO: pk118-1 from *Arabidopsis thaliana* (SEQ ID NO:29) of the present invention. The polynucleotide sequence contains 2391 nucleotides. FIG. 12D shows the deduced amino acid sequence of SEQ ID NO:29 (SEQ ID NO:30) (Clone ID NO: pk118-1) of the present invention. The polypeptide sequence contains 797 amino acids. The standard one-letter abbreviation for amino acids is used to illustrate the deduced amino acid sequence.

FIGS. 13A-B. FIG. 13A shows the polynucleotide sequences of the open reading frame of Clone ID NO: pk120 from *Arabidopsis thaliana* (SEQ ID NO:31) of the present invention. The polynucleotide sequence contains 1530 nucleotides. FIG. 13B shows the deduced amino acid sequence of SEQ ID NO:31 (SEQ ID NO:32) (Clone ID NO: pk120) of the present invention. The polypeptide sequence contains 510 amino acids. The standard one-letter abbreviation for amino acids is used to illustrate the deduced amino acid sequence.

DETAILED DESCRIPTION OF THE INVENTION

The present invention may be understood more readily by reference to the following detailed description of the preferred embodiments of the invention and the Examples included therein.

Before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing particular embodiments only and is not intended to be limiting. As used in the specification and in the claims, "a" or "an" can mean one or more, depending upon the context in which it is used. Thus, for example, reference to "a cell" can mean that at least one cell can be utilized.

In accordance with the purpose(s) of this invention, as embodied and broadly described herein, this invention, in one aspect, provides an isolated nucleic acid from a plant (*Arabidopsis thaliana*) encoding a Lipid Metabolism Protein (LMP), or a portion thereof.

One aspect of the invention pertains to isolated nucleic acid molecules that encode LMP polypeptides or biologically active portions thereof, as well as nucleic acid fragments sufficient for use as hybridization probes or primers for the identification or amplification of an LMP-encoding nucleic acid (e.g., LMP DNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of a gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA. An "isolated" nucleic acid molecule is one which is substantially separated from other nucleic acid molecules which are present in the natural source of the nucleic acid. Preferably, an "isolated" nucleic acid is substantially free of sequences which naturally flank the nucleic acid (i.e., sequences located at the 5' and 3' ends of the nucleic acid) in the genomic DNA of the organism from which the nucleic acid is derived. For example, in various embodiments, the isolated LMP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Arabidopsis thaliana* cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having a nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, or a portion thereof, can be isolated using standard molecular biology techniques and the sequence information provided herein. For example, an *Arabidopsis thaliana* LMP cDNA can be isolated from an *Arabidopsis thaliana* library using all or portion of one of the sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 as a hybridization probe and standard hybridization techniques (e.g., as described in Sambrook et al. 1989, *Molecular Cloning: A Laboratory Manual*. 2nd, ed., Cold Spring Harbor Laboratory, Cold Spring Harbor Laboratory Press, Cold Spring Harbor, N.Y.). Moreover, a nucleic acid molecule encompassing all or a portion of one of the sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 can be isolated by the polymerase chain reaction using oligonucleotide primers designed based upon this sequence (e.g., a nucleic acid molecule encompassing all or a portion of one of the sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 can be isolated by the polymerase chain reaction using oligonucleotide primers designed based upon this same sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31). For example, mRNA can be isolated from plant cells (e.g., by the guanidinium-thiocyanate extraction procedure of Chirgwin et al. 1979, Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a LMP nucleotide sequence can be prepared by standard synthetic techniques, e.g., using an automated DNA synthesizer.

In a preferred embodiment, an isolated nucleic acid of the invention comprises one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. These polynucleotides correspond to the *Arabidopsis thaliana* LMP cDNAs of the invention. These cDNAs comprise sequences encoding LMPs (i.e., the "coding region"), as well as 5' untranslated sequences and 3' untranslated sequences. Alternatively, the nucleic acid molecules can comprise only the coding region of any of the polynucleotide sequences described herein. Examples of polynucleotides comprising only the coding region or open reading frame (ORF) are shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31.

For the purposes of this application, it will be understood that each of the sequences set forth in the Figures has an identifying entry number (e.g., pk109). Each of these sequences may generally comprise three parts: a 5' upstream region, a coding region, and a downstream region. The particular sequences shown in the figures represent the open reading frames. The putative functions of these proteins are indicated in Table 3. In another preferred embodiment, an isolated nucleic acid molecule of the present invention encodes a polypeptide that is able to participate in the metabolism of seed storage compounds such as lipids, starch and seed storage proteins and that contains an antioxidant domain, a beta-oxidation domain, an acyltransferase domain, a dehydrogenase domain, an ATP synthase domain, a kinase domain, an isocitrate lyase domain, a sucrose synthase domain, or a membrane-associated domain. Examples of isolated LMPs that contain such domains can be found in Table 4. LMPs containing an antioxidant domain include that shown in SEQ ID NO:1. LMPs containing a beta-oxidation domain include that shown in SEQ ID NO:3. LMPs containing an acyltransferase domain include that shown in SEQ ID NO:5. LMPs containing a dehydrogenase domain include those shown in SEQ ID NO:7 and SEQ ID NO:25. LMPs containing an ATP synthase domain include that shown in SEQ ID NO:21. LMPs containing a kinase domain include those shown in SEQ ID NO:9, SEQ ID NO:11, SEQ ID NO:13, SEQ ID NO:23, and SEQ ID NO:31. LMPs containing an isocitrate lyase domain include that shown in SEQ ID NO:19. LMPs containing a membrane-associated domain include those shown in SEQ ID NO:15 and SEQ ID NO:17.

In another preferred embodiment, an isolated nucleic acid molecule of the invention comprises a nucleic acid molecule which is a complement of any of the nucleic acid sequences disclosed herein, including one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, or a portion thereof. As used herein, the term "complementary" refers to a nucleotide sequence that can hybridize to one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31.

In still another preferred embodiment, an isolated nucleic acid molecule of the invention comprises a nucleotide sequence which is at least about 50-60%, preferably at least about 60-70%, more preferably at least about 70-80%, 80-90%, or 90-95%, and even more preferably at least about 95%, 96%, 97%, 98%, 99% or more homologous to a nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, or a portion thereof. In an additional preferred embodiment, an isolated nucleic acid molecule of the invention comprises a nucleotide sequence which hybridizes, e.g., hybridizes under stringent conditions, to one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, or a portion thereof. These hybridization conditions include washing with a solution having a salt concentration of about 0.02 molar at pH 7 at about 60° C.

Moreover, the nucleic acid molecule of the invention can comprise only a portion of the coding region of one of the sequences in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, for example a fragment which can be used as a probe or primer or a fragment encoding a biologically active portion of a LMP. The nucleotide sequences determined from the cloning of the LMP genes from *Arabidopsis thaliana* allows for the generation of probes and primers designed for use in identifying and/or cloning LMP homologues in other cell types and organisms, as well as LMP homologues from other plants or related species. Therefore this invention also provides compounds comprising the nucleic acids disclosed herein, or fragments thereof. These compounds include the nucleic acids attached to a moiety. These moieties include, but are not limited to, detection moieties, hybridization moieties, purification moieties, delivery moieties, reaction moieties, binding moieties, and the like. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, an anti-sense sequence of one of the sequences set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, or naturally occurring mutants thereof. Primers based on a nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 can be used in PCR reactions to clone LMP homologues. Probes based on the LMP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a LMP, such as by measuring a level of a LMP-encoding nucleic acid in a sample of cells, e.g., detecting LMP mRNA levels or determining whether a genomic LMP gene has been mutated or deleted.

In one embodiment, the nucleic acid molecule of the invention encodes a protein or portion thereof which includes an amino acid sequence which is sufficiently homologous to an amino acid encoded by a sequence of shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32 such that the protein or portion thereof maintains the same or a similar function as the wild-type protein. As used herein, the language "sufficiently homologous" refers to proteins or portions thereof which have amino acid sequences which include a minimum number of identical or equivalent (e.g., an amino acid residue which has a similar side chain as an amino acid residue in one of the ORFs of a sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32) amino acid residues to an amino acid sequence such that the protein or portion thereof is able to participate in the metabolism of compounds necessary for the production of seed storage compounds in plants, construction of cellular membranes in microorganisms or plants, or in the transport of molecules across these membranes. Regulatory proteins, such as DNA binding proteins, transcription factors, kinases, phosphatases, or protein members of metabolic pathways such as the lipid, starch and protein biosynthetic pathways, or membrane transport systems, may play a role in the biosynthesis of seed storage compounds. Examples of such activities are described herein (see putative annotations in Table 3). Examples of LMP-encoding nucleic acid sequences are set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31.

As altered or increased sugar and/or fatty acid production is a general trait wished to be inherited into a wide variety of plants like maize, wheat, rye, oat, triticale, rice, barley, soybean, peanut, cotton, rapeseed, canola, *manihot*, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut) and perennial grasses and forage crops, these crop plants are also preferred target plants for genetic engineering as one further embodiment of the present invention.

Portions of proteins encoded by the LMP nucleic acid molecules of the invention are preferably biologically active portions of one of the LMPs. As used herein, the term "biologically active portion of a LMP" is intended to include a portion, e.g., a domain/motif, of a LMP that participates in the metabolism of compounds necessary for the biosynthesis of seed storage lipids, or the construction of cellular membranes in microorganisms or plants, or in the transport of molecules across these membranes, or has an activity as set forth in Table 3. To determine whether a LMP or a biologically active portion thereof can participate in the metabolism of compounds necessary for the production of seed storage compounds and cellular membranes, an assay of enzymatic activity may be performed. Such assay methods are well known to those skilled in the art, and as described in Example 14 of the Exemplification.

Biologically active portions of a LMP include peptides comprising amino acid sequences derived from the amino acid sequence of a LMP (e.g., an amino acid sequence encoded by a nucleic acid shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 or the amino acid sequence of a protein homologous to a LMP, which include fewer amino acids than a full length LMP or the full length protein which is homologous to a LMP) and exhibit at least one activity of a LMP. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of a LMP. Moreover, other biologically active portions, in which other regions of the protein are deleted, can be prepared by recombinant techniques and evaluated for one or more of the activities described herein. Preferably, the biologically active portions of a LMP include one or more selected domains/motifs or portions thereof having biological activity.

Additional nucleic acid fragments encoding biologically active portions of a LMP can be prepared by isolating a portion of one of the sequences, expressing the encoded portion of the LMP or peptide (e.g., by recombinant expression in vitro) and assessing the activity of the encoded portion of the LMP or peptide.

The invention further encompasses nucleic acid molecules that differ from one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 (and portions thereof) due to degeneracy of the genetic code and thus encode the same LMP as that encoded by the nucleotide sequences shown in the above SEQ ID Nos in the Figures. In a further embodiment, the nucleic acid molecule of the invention encodes a full length protein which is substantially homologous to an amino acid sequence of a polypeptide encoded by an open reading frame shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. In one embodiment, the full-length nucleic acid or protein or fragment of the nucleic acid or protein is from *Arabidopsis thaliana*.

In addition to the *Arabidopsis thaliana* LMP nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, it will be appreciated by those skilled in the art that DNA sequence polymorphisms that lead to changes in the amino acid sequences of LMPs may exist within a population (e.g., the *Arabidopsis thaliana* population). Such genetic polymorphism in the LMP gene may exist among individuals within a population due to natural variation. As used herein, the terms "gene" and "recombinant gene" refer to nucleic acid molecules comprising an open reading frame encoding a LMP, preferably a *Arabidopsis thaliana* LMP. Such natural variations can typically result in 1-40% variance in the nucleotide sequence of the LMP gene. Any and all such nucleotide variations and resulting amino acid polymorphisms in LMP that are the result of natural variation and that do not alter the functional activity of LMPs are intended to be within the scope of the invention.

Nucleic acid molecules corresponding to natural variants and non-*Arabidopsis thaliana* orthologs of the *Arabidopsis thaliana* LMP cDNA of the invention can be isolated based on their homology to *Arabidopsis thaliana* LMP nucleic acid disclosed herein using the *Arabidopsis thaliana* cDNA, or a portion thereof, as a hybridization probe according to standard hybridization techniques under stringent hybridization conditions. As used herein, the term "orthologs" refers to two nucleic acids from different species, but that have evolved from a common ancestral gene by speciation. Normally, orthologs encode proteins having the same or similar functions. Accordingly, in another embodiment, an isolated nucleic acid molecule of the invention is at least 15 nucleotides in length and hybridizes under stringent conditions to the nucleic acid molecule comprising a nucleotide sequence shown SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. In other embodiments, the nucleic acid is at least 30, 50, 100, 250 or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to a sequence shown SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *Arabidopsis thaliana* LMP.

In addition to naturally-occurring variants of the LMP sequence that may exist in the population, the skilled artisan will further appreciate that changes can be introduced by mutation into a nucleotide sequence shown SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, thereby leading to changes in the amino acid sequence of the encoded LMP, without altering the functional ability of the LMP. For example, nucleotide substitutions leading to amino acid substitutions at "non-essential" amino acid residues can be made in a sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. A "non-essential" amino acid residue is a residue that can be altered from the wild-type sequence of one of the LMPs (SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32) without altering the activity of said LMP, whereas an "essential" amino acid residue is required for LMP activity. Other amino acid residues, however, (e.g., those that are not conserved or only semi-conserved in the domain having LMP activity) may not be essential for activity and thus are likely to be amenable to alteration without altering LMP activity.

Accordingly, another aspect of the invention pertains to nucleic acid molecules encoding LMPs that contain changes in amino acid residues that are not essential for LMP activity. Such LMPs differ in amino acid sequence from a sequence yet retain at least one of the LMP activities described herein. In one embodiment, the isolated nucleic acid molecule comprises a nucleotide sequence encoding a protein, wherein the protein comprises an amino acid sequence at least about 50% homologous to an amino acid sequence encoded by a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, and is capable of participation in the metabolism of compounds necessary for the production of seed storage compounds in *Arabidopsis thaliana*, or cellular membranes, or has one or more activities set forth in Table 3. Preferably, the protein encoded by the nucleic acid molecule is at least about 50-60% homologous to one of the sequences encoded by a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, more preferably at least about 60-70% homologous to one of the sequences encoded by a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, even more preferably at least about 70-80%, 80-90%, 90-95% homologous to one of the sequences encoded by a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, and most preferably at least about 96%, 97%, 98%, or 99% homologous to one of the sequences encoded by a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31.

To determine the percent homology of two amino acid sequences (e.g., one of the sequences encoded by a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences encoded by a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31) is occupied by the same amino acid residue or nucleotide as the corresponding position in the other sequence (e.g., a mutant form of the sequence selected from the polypeptide encoded by a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100).

An isolated nucleic acid molecule encoding a LMP homologous to a protein sequence encoded by a nucleic acid shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 can be created by introducing one or more nucleotide substitutions, additions or deletions into a nucleotide sequence SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 such that one or more amino acid substitutions, additions or deletions are introduced into the encoded protein. Mutations can be introduced into one of the sequences SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a LMP is preferably replaced with another amino acid residue from the same side chain family. Alternatively, in another embodiment, mutations can be introduced randomly along all or part of a LMP coding sequence, such as by saturation mutagenesis, and the resultant mutants can be screened for a LMP activity described herein to identify mutants that retain LMP activity. Following mutagenesis of one of the sequences SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, the encoded protein can be expressed recombinantly and the activity of the protein can be determined using, for example, assays described herein (see Examples 11-13 of the Exemplification).

LMPs are preferably produced by recombinant DNA techniques. For example, a nucleic acid molecule encoding the protein is cloned into an expression vector (as described above), the expression vector is introduced into a host cell (as described herein) and the LMP is expressed in the host cell. The LMP can then be isolated from the cells by an appropriate purification scheme using standard protein purification techniques. Alternative to recombinant expression, a LMP or peptide thereof can be synthesized chemically using standard peptide synthesis techniques. Moreover, native LMP can be isolated from cells, for example using an anti-LMP antibody, which can be produced by standard techniques utilizing a LMP or fragment thereof of this invention.

The invention also provides LMP chimeric or fusion proteins. As used herein, a LMP "chimeric protein" or "fusion protein" comprises a LMP polypeptide operatively linked to a non-LMP polypeptide. An "LMP polypeptide" refers to a polypeptide having an amino acid sequence corresponding to a LMP, whereas a "non-LMP polypeptide" refers to a polypeptide having an amino acid sequence corresponding to a protein which is not substantially homologous to the LMP, e.g., a protein which is different from the LMP and which is derived from the same or a different organism. Within the fusion protein, the term "operatively linked" is intended to indicate that the LMP polypeptide and the non-LMP polypeptide are fused to each other so that both sequences fulfill the proposed function attributed to the sequence used. The non-LMP polypeptide can be fused to the N-terminus or C-terminus of the LMP polypeptide. For example, in one embodiment, the fusion protein is a GST-LMP (glutathione S-transferase) fusion protein in which the LMP sequences are fused to the C-terminus of the GST sequences. Such fusion proteins can facilitate the purification of recombinant LMPs. In another embodiment, the fusion protein is a LMP containing a heterologous signal sequence at its N-terminus. In certain host cells (e.g., mammalian host cells), expression and/or secretion of a LMP can be increased through use of a heterologous signal sequence.

Preferably, a LMP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al., John Wiley & Sons: 1992). Moreover, many expression vectors are commercially available that already encode a fusion moiety (e.g., a GST polypeptide). An LMP-encoding nucleic acid can be cloned into such an expression vector such that the fusion moiety is linked in-frame to the LMP.

In addition to the nucleic acid molecules encoding LMPs described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire LMP coding strand, or to only a portion thereof. In one embodiment, an antisense nucleic acid molecule is antisense to a "coding region" of the coding strand of a nucleotide sequence encoding a LMP. The term "coding region" refers to the region of the nucleotide sequence comprising codons which are translated into amino acid residues (e.g., the entire coding region of Pk109 comprises nucleotides 1 to 1173). In another embodiment, the antisense nucleic acid molecule is antisense to a "noncoding region" of the coding strand of a nucleotide sequence encoding LMP. The term "noncoding region" refers to 5' and 3' sequences which flank the coding region that are not translated into amino acids (i.e., also referred to as 5' and 3' untranslated regions).

Given the coding strand sequences encoding LMP disclosed herein (e.g., the sequences set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31), antisense nucleic acids of the invention can be designed according to the rules of Watson and Crick base pairing. The antisense nucleic acid molecule can be complementary to the entire coding region of LMP mRNA, but more preferably is an oligonucleotide which is antisense to only a portion of the coding or noncoding region of LMP mRNA. For example, the antisense oligonucleotide can be complementary to the region surrounding the translation start site of LMP mRNA. An antisense oligonucleotide can be, for example, about 5, 10, 15, 20, 25, 30, 35, 40, 45 or 50 nucleotides in length. An antisense or sense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylamino-methyl-2-thiouridine, 5-carboxymethylaminomethyluracil, dihydro-uracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methyl-cytosine, N-6-adenine, 7-methylguanine, 5-methylaminomethyluracil, 5-methoxyamino-methyl-2-thiouracil, beta-D-mannosylqueosine, 5'-methoxycarboxymethyl-uracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diamino-purine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another variation of the antisense technology, a double-strand interfering RNA construct can be used to cause a down-regulation of the LMP mRNA level and LMP activity in transgenic plants. This requires transforming the plants with a chimeric construct containing a portion of the LMP sequence in the sense orientation fused to the antisense sequence of the same portion of the LMP sequence. A DNA linker region of variable length can be used to separate the sense and antisense fragments of LMP sequences in the construct (see, for example Chuang & Meyerowitz 2000, Proc. Natl. Acad Sci USA 97:4985-4990).

The antisense nucleic acid molecules of the invention are typically administered to a cell or generated in situ such that they hybridize with or bind to cellular mRNA and/or genomic DNA encoding a LMP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic including plant promoters are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. 1987, Nucleic Acids Res. 15:6625-6641). The antisense nucleic acid molecule can also comprise a 2'-o-methylribonucleotide (Inoue et al. 1987, Nucleic Acids Res. 15:6131-6148) or a chimeric RNA-DNA analogue (Inoue et al. 1987, FEBS Lett 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff & Gerlach 1988, Nature 334:585-591)) can be used to catalytically cleave LMP mRNA transcripts to thereby inhibit translation of LMP mRNA. A ribozyme having specificity for a LMP-encoding nucleic acid can be designed based upon the nucleotide sequence of a LMP cDNA disclosed herein (i.e., Pk109 in FIG. 9A) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a LMP-encoding mRNA (see, e.g., Cech et al., U.S. Pat. No. 4,987,071 and Cech et al., U.S. Pat. No. 5,116,742). Alternatively, LMP mRNA can be used to select a catalytic RNA having a specific ribonuclease activity from a pool of RNA molecules (see, e.g., Bartel, D. & Szostak J. W. 1993, Science 261:1411-1418).

Alternatively, LMP gene expression can be inhibited by targeting nucleotide sequences complementary to the regulatory region of a LMP nucleotide sequence (e.g., a LMP promoter and/or enhancers) to form triple helical structures that prevent transcription of a LMP gene in target cells (See generally, Helene C. 1991, Anticancer Drug Des. 6:569-84; Helene C. et al. 1992, Ann N.Y. Acad. Sci. 660:27-36; and Maher, L. J. 1992, Bioassays 14:807-15).

Another aspect of the invention pertains to vectors, preferably expression vectors, containing a nucleic acid encoding a LMP (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used inter-changeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence and both sequences are fused to each other so that each fulfills its proposed function (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990) or see: Gruber and Crosby, in: Methods in Plant Molecular Biology and Biotechnolgy, CRC Press, Boca Raton, Fla., eds.: Glick & Thompson, Chapter 7, 89-108 including the references therein. Regulatory sequences include those which direct constitutive expression of a nucleotide sequence in many types of host cell and those which direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., LMPs, mutant forms of LMPs, fusion proteins, etc.).

The recombinant expression vectors of the invention can be designed for expression of LMPs in prokaryotic or eukaryotic cells. For example, LMP genes can be expressed in bacterial cells, insect cells (using baculovirus expression vectors), yeast and other fungal cells (see Romanos M. A. et al. 1992, Foreign gene expression in yeast: a review, Yeast 8:423-488; van den Hondel, C. A. M. J. J. et al. 1991, Heterologous gene expression in filamentous fungi, in: More Gene Manipulations in Fungi, Bennet & Lasure, eds., p. 396-428:Academic Press: an Diego; and van den Hondel & Punt 1991, Gene transfer systems and vector development for filamentous fungi, in: Applied Molecular Genetics of Fungi, Peberdy et al., eds., p. 1-28, Cambridge University Press: Cambridge), algae (Falciatore et al. 1999, Marine Biotechnology 1:239-251), ciliates of the types: Holotrichia, Peritrichia, Spirotrichia, Suctoria, *Tetrahymena, Paramecium, Colpidium, Glaucoma, Platyophrya, Potomacus, Pseudocohnilembus, Euplotes, Engelmaniella*, and *Stylonychia*, especially of the genus *Stylonychia lemnae* with vectors following a transformation method as described in WO 98/01572 and multicellular plant cells (see Schmidt & Willmitzer 1988, High efficiency *Agrobacterium tumefaciens*-mediated transformation of *Arabidopsis thaliana* leaf and cotyledon plants, Plant Cell Rep.: 583-586); Plant Molecular Biology and Biotechnology, C Press, Boca Raton, Fla., chapter 6/7, S.71-119 (1993); White, Jenes et al., Techniques for Gene Transfer, in: Transgenic Plants, Vol. 1, Engineering and Utilization, eds.: Kung and Wu, Academic Press 1993, 128-43; Potrykus 1991, Annu Rev. Plant Physiol. Plant Mol. Biol. 42:205-225 (and references cited therein) or mammalian cells. Suitable host cells are discussed further in Goeddel, Gene Expression Technology: Methods in Enzymology 185, Academic Press, San Diego, Calif. 1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve one or more of the following purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith & Johnson 1988, Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the LMP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant LMP unfused to GST can be recovered by cleavage of the fusion protein with thrombin.

Examples of suitable inducible non-fusion *E. coli* expression vectors include pTrc (Amann et al. 1988, Gene 69:301-315) and pET 11d (Studier et al. 1990, Gene Expression Technology:Methods in Enzymology 185, Academic Press, San Diego, Calif. 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman S. 1990, Gene Expression Technology:Methods in Enzymology 185:119-128, Academic Press, San Diego, Calif.). Another strategy is to alter the nucleic acid sequence of the nucleic acid to be inserted into an expression vector so that the individual codons for each amino acid are those preferentially utilized in the bacterium chosen for expression (Wada et al. 1992, Nucleic Acids Res. 20:2111-2118). Such alteration of nucleic acid sequences of the invention can be carried out by standard DNA synthesis techniques.

In another embodiment, the LMP expression vector is a yeast expression vector. Examples of vectors for expression in yeast *S. cerevisiae* include pYepSec1 (Baldari et al. 1987, Embo J. 6:229-234), pMFa (Kurjan & Herskowitz 1982, Cell 30:933-943), pJRY88 (Schultz et al. 1987, Gene 54:113-123), and pYES2 (Invitrogen Corporation, San Diego, Calif.). Vectors and methods for the construction of vectors appropriate for use in other fungi, such as the filamentous fungi, include those detailed in: van den Hondel & Punt 1991, "Gene transfer systems and vector development for filamentous fungi, in: Applied Molecular Genetics of Fungi, Peberdy et al., eds., p. 1-28, Cambridge University Press: Cambridge.

Alternatively, the LMPs of the invention can be expressed in insect cells using baculovirus expression vectors. Baculovirus vectors available for expression of proteins in cultured insect cells (e.g., Sf 9 cells) include the pAc series (Smith et al. 1983, Mol. Cell. Biol. 3:2156-2165) and the pVL series (Lucklow & Summers 1989, Virology 170:31-39).

In yet another embodiment, a nucleic acid of the invention is expressed in mammalian cells using a mammalian expression vector. Examples of mammalian expression vectors include pCDM8 (Seed 1987, Nature 329:840) and pMT2PC (Kaufman et al. 1987, EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, Fritsh and Maniatis, *Molecular Cloning: A Laboratory Manual.* 2nd, ed, *Cold Spring Harbor Laboratory*, Cold Spring Harbor Laboratory Press, Cold Spring Harbor, N.Y., 1989.

In another embodiment, the LMPs of the invention may be expressed in uni-cellular plant cells (such as algae, see Falciatore et al. (1999, Marine Biotechnology 1:239-251 and references therein) and plant cells from higher plants (e.g., the spermatophytes, such as crop plants). Examples of plant expression vectors include those detailed in: Becker, Kemper, Schell and Masterson (1992, "New plant binary vectors with selectable markers located proximal to the left border", Plant Mol. Biol. 20:1195-1197) and Bevan (1984, "Binary *Agrobacterium* vectors for plant transformation, Nucleic Acids Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38).

A plant expression cassette preferably contains regulatory sequences capable to drive gene expression in plant cells and which are operably linked so that each sequence can fulfil its function such as termination of transcription such as polyadenylation signals. Preferred polyadenylation signals are those originating from *Agrobacterium tumefaciens* t-DNA such as the gene 3 known as octopine synthase of the Ti-plasmid pTiACH5 (Gielen et al. 1984, EMBO J. 3:835) or functional equivalents thereof but also all other terminators functionally active in plants are suitable.

As plant gene expression is very often not limited on transcriptional levels a plant expression cassette preferably contains other operably linked sequences like translational enhancers such as the overdrive-sequence containing the 5'-untranslated leader sequence from tobacco mosaic virus enhancing the protein per RNA ratio (Gallie et al. 1987, Nucleic Acids Res. 15:8693-8711).

Plant gene expression has to be operably linked to an appropriate promoter conferring gene expression in a timely, cell or tissue specific manner. Preferred are promoters driving constitutive expression (Benfey et al. 1989, EMBO J. 8:2195-2202) like those derived from plant viruses like the 35S CAMV (Franck et al. 1980, Cell 21:285-294), the 19S CaMV (see also U.S. Pat. No. 5,352,605 and WO 84/02913) or plant promoters like those from Rubisco small subunit described in U.S. Pat. No. 4,962,028. Even more preferred are seed-specific promoters driving expression of LMP proteins during all or selected stages of seed development. Seed-specific plant promoters are known to those of ordinary skill in the art and are identified and characterized using seed-specific mRNA libraries and expression profiling techniques. Seed-specific promoters include the napin-gene promoter from rapeseed (U.S. Pat. No. 5,608,152), the USP-promoter from *Vicia faba* (Baeumlein et al. 1991, Mol. Gen. Genetics 225:459-67), the oleosin-promoter from *Arabidopsis* (WO 98/45461), the phaseolin-promoter from *Phaseolus vulgaris* (U.S. Pat. No. 5,504,200), the Bce4-promoter from *Brassica* (WO9113980) or the legumin B4 promoter (LeB4; Baeumlein et al. 1992, Plant J. 2:233-239) as well as promoters conferring seed specific expression in monocot plants like maize, barley, wheat, rye, rice etc. Suitable promoters to note are the lpt2 or lpt1-gene promoter from barley (WO 95/15389 and WO 95/23230) or those described in WO 99/16890 (promoters from the barley hordein-gene, the rice glutelin gene, the rice oryzin gene, the rice prolamin gene, the wheat gliadin gene, wheat glutelin gene, the maize zein gene, the oat glutelin gene, the *Sorghum* kasirin-gene, the rye secalin gene).

Plant gene expression can also be facilitated via an inducible promoter (for review see Gatz 1997, Annu. Rev. Plant Physiol. Plant Mol. Biol. 48:89-108). Chemically inducible promoters are especially suitable if gene expression is desired in a time specific manner. Examples for such promoters are a salicylic acid inducible promoter (WO 95/19443), a tetracycline inducible promoter (Gatz et al. 1992, Plant J. 2:397-404) and an ethanol inducible promoter (WO 93/21334).

Promoters responding to biotic or abiotic stress conditions are also suitable promoters such as the pathogen inducible PRP1-gene promoter (Ward et al., 1993, Plant. Mol. Biol. 22:361-366), the heat inducible hsp80-promoter from tomato (U.S. Pat. No. 5,187,267), cold inducible alpha-amylase promoter from potato (WO 96/12814) or the wound-inducible pinII-promoter (EP 375091).

Other preferred sequences for use in plant gene expression cassettes are targeting-sequences necessary to direct the gene-product in its appropriate cell compartment (for review see Kermode 1996, Crit. Rev. Plant Sci. 15:285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells. Also especially suited are promoters that confer plastid-specific gene expression, as plastids are the compartment where precursors and some end products of lipid biosynthesis are synthesized. Suitable promoters such as the viral RNA-polymerase promoter are described in WO 95/16783 and WO 97/06250 and the clpP-promoter from *Arabidopsis* described in WO 99/46394.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to LMP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986, Antisense RNA as a molecular tool for genetic analysis, Reviews—Trends in Genetics, Vol. 1) and Mol et al. (1990, FEBS Lett. 268:427-430).

Another aspect of the invention pertains to host cells into which a recombinant expression vector of the invention has been introduced. The terms "host cell" and "recombinant host cell" are used interchangeably herein. It is to be understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a LMP can be expressed in bacterial cells, insect cells, fungal cells, mammalian cells (such as Chinese hamster ovary cells (CHO) or COS cells), algae, ciliates or plant cells. Other suitable host cells are known to those skilled in the art.

Vector DNA can be introduced into prokaryotic or eukaryotic cells via conventional transformation or transfection techniques. As used herein, the terms "transformation" and "transfection", "conjugation" and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells including plant cells can be found in Sambrook et al. (1989, *Molecular Cloning: A Laboratory Manual.* 2nd, ed., Cold Spring Harbor Laboratory, Cold Spring Harbor Laboratory Press, Cold Spring Harbor, N.Y.) and other laboratory manuals such as Methods in Molecular Biology 1995, Vol. 44, *Agrobacterium* protocols, ed: Gartland and Davey, Humana Press, Totowa, N.J.

For stable transfection of mammalian and plant cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, kanamycin and methotrexate or in plants that confer resistance towards an herbicide such as glyphosate or glufosinate. A nucleic acid encoding a selectable marker can be introduced into a host cell on the same vector as that encoding a LMP or can be introduced on a separate vector. Cells stably transfected with the introduced nucleic acid can be identified by, for example, drug selection (e.g., cells that have incorporated the selectable marker gene will survive, while the other cells die).

To create a homologous recombinant microorganism, a vector is prepared which contains at least a portion of a LMP gene into which a deletion, addition or substitution has been introduced to thereby alter, e.g., functionally disrupt, the LMP gene. Preferably, this LMP gene is an *Arabidopsis thaliana* LMP gene, but it can be a homologue from a related plant or even from a mammalian, yeast, or insect source. In a preferred embodiment, the vector is designed such that, upon homologous recombination, the endogenous LMP gene is functionally disrupted (i.e., no longer encodes a functional protein; also referred to as a knock-out vector). Alternatively, the vector can be designed such that, upon homologous recombination, the endogenous LMP gene is mutated or otherwise altered but still encodes functional protein (e.g., the upstream regulatory region can be altered to thereby alter the expression of the endogenous LMP). To create a point mutation via homologous recombination, DNA-RNA hybrids can be used in a technique known as chimeraplasty (Cole-Strauss et al. 1999, Nucleic Acids Res. 27:1323-1330 and Kmiec 1999, American Scientist 87:240-247). Homologous recombination procedures in *Arabidopsis thaliana* are also well known in the art and are contemplated for use herein.

In a homologous recombination vector, the altered portion of the LMP gene is flanked at its 5' and 3' ends by additional nucleic acid of the LMP gene to allow for homologous recombination to occur between the exogenous LMP gene carried by the vector and an endogenous LMP gene in a microorganism or plant. The additional flanking LMP nucleic acid is of sufficient length for successful homologous recombination with the endogenous gene. Typically, several hundreds of base pairs up to kilobases of flanking DNA (both at the 5' and 3' ends) are included in the vector (see e.g., Thomas & Capecchi 1987, Cell 51:503, for a description of homologous recombination vectors). The vector is introduced into a microorganism or plant cell (e.g., via polyethyleneglycol mediated DNA). Cells in which the introduced LMP gene has homologously recombined with the endogenous LMP gene are selected using art-known techniques.

In another embodiment, recombinant microorganisms can be produced which contain selected systems which allow for regulated expression of the introduced gene. For example, inclusion of a LMP gene on a vector placing it under control of the lac operon permits expression of the LMP gene only in the presence of IPTG. Such regulatory systems are well known in the art.

A host cell of the invention, such as a prokaryotic or eukaryotic host cell in culture can be used to produce (i.e., express) a LMP. Accordingly, the invention further provides methods for producing LMPs using the host cells of the invention. In one embodiment, the method comprises culturing a host cell of the invention (into which a recombinant expression vector encoding a LMP has been introduced, or which contains a wild-type or altered LMP gene in it's genome) in a suitable medium until LMP is produced. In another embodiment, the method further comprises isolating LMPs from the medium or the host cell.

Another aspect of the invention pertains to isolated LMPs, and biologically active portions thereof. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of LMP in which the protein is separated from cellular components of the cells in which it is naturally or recombinantly produced. In one embodiment, the language "substantially free of cellular material" includes preparations of LMP having less than about 30% (by dry weight) of non-LMP (also referred to herein as a "contaminating protein"), more preferably less than about 20% of non-LMP, still more preferably less than about 10% of non-LMP, and most preferably less than about 5% non-LMP. When the LMP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of LMP in which the protein is separated from chemical precursors or other chemicals which are involved in the synthesis of the protein. In one embodiment, the language "substantially free of chemical precursors or other chemicals" includes preparations of LMP having less than about 30% (by dry weight) of chemical precursors or non-LMP chemicals, more preferably less than about 20% chemical precursors or non-LMP chemicals, still more preferably less than about 10% chemical precursors or non-LMP chemicals, and most preferably less than about 5% chemical precursors or non-LMP chemicals. In preferred embodiments, isolated proteins or biologically active portions thereof lack contaminating proteins from the same organism from which the LMP is derived. Typically, such proteins are produced by recombinant expression of, for example, an *Arabidopsis thaliana* LMP in other plants than *Arabidopsis thaliana* or microorganisms, algae or fungi.

An isolated LMP or a portion thereof of the invention can participate in the metabolism of compounds necessary for the production of seed storage compounds in *Arabidopsis thaliana*, or of cellular membranes, or has one or more of the activities set forth in Table 3. In preferred embodiments, the protein or portion thereof comprises an amino acid sequence which is sufficiently homologous to an amino acid sequence encoded by a nucleic acid of the Figures such that the protein or portion thereof maintains the ability to participate in the metabolism of compounds necessary for the construction of cellular membranes in *Arabidopsis thaliana*, or in the transport of molecules across these membranes. The portion of the protein is preferably a biologically active portion as described herein. In another preferred embodiment, a LMP of the invention has an amino acid sequence encoded by a nucleic acid shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. In yet another preferred embodiment, the LMP has an amino acid sequence which is encoded by a nucleotide sequence which hybridizes, e.g., hybridizes under stringent conditions, to a nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. In still another preferred embodiment, the LMP has an amino acid sequence which is encoded by a nucleotide sequence that is at least about 50-60%, preferably at least about 60-70%, more preferably at least about 70-80%, 80-90%, 90-95%, and even more preferably at least about 96%, 97%, 98%, 99% or more homologous to one of the amino acid sequences encoded by a nucleic acid shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. The preferred LMPs of the present invention also preferably possess at least one of the LMP activities described herein. For example, a preferred LMP of the present invention includes an amino acid sequence encoded by a nucleotide sequence which hybridizes, e.g., hybridizes under stringent conditions, to a nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 of the Figures, and which can participate in the metabolism of compounds necessary for the construction of cellular membranes in *Arabidopsis thaliana*, or in the transport of molecules across these membranes, or which has one or more of the activities set forth in Table 3.

In other embodiments, the LMP is substantially homologous to an amino acid sequence encoded by a nucleic acid shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 and retains the functional activity of the protein of one of the sequences encoded by a nucleic acid shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 yet differs in amino acid sequence due to natural variation or mutagenesis, as described in detail above. Accordingly, in another embodiment, the LMP is a protein which comprises an amino acid sequence which is at least about 50-60%, preferably at least about 60-70%, and more preferably at least about 70-80, 80-90, 90-95%, and most preferably at least about 96%, 97%, 98%, 99% or more homologous to an entire amino acid sequence and which has at least one of the LMP activities described herein. In another embodiment, the invention pertains to a full *Arabidopsis thaliana* protein which is substantially homologous to an entire amino acid sequence encoded by a nucleic acid shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31.

Homologues of the LMP can be generated by mutagenesis, e.g., discrete point mutation or truncation of the LMP. As used herein, the term "homologue" refers to a variant form of the LMP which acts as an agonist or antagonist of the activity of the LMP. An agonist of the LMP can retain substantially the same, or a subset, of the biological activities of the LMP. An antagonist of the LMP can inhibit one or more of the activities of the naturally occurring form of the LMP, by, for example, competitively binding to a downstream or upstream member of the cell membrane component metabolic cascade which includes the LMP, or by binding to a LMP which mediates transport of compounds across such membranes, thereby preventing translocation from taking place.

In an alternative embodiment, homologues of the LMP can be identified by screening combinatorial libraries of mutants, e.g., truncation mutants, of the LMP for LMP agonist or antagonist activity. In one embodiment, a variegated library of LMP variants is generated by combinatorial mutagenesis at the nucleic acid level and is encoded by a variegated gene library. A variegated library of LMP variants can be produced by, for example, enzymatically ligating a mixture of synthetic oligonucleotides into gene sequences such that a degenerate set of potential LMP sequences is expressible as individual polypeptides, or alternatively, as a set of larger fusion proteins (e.g., for phage display) containing the set of LMP sequences therein. There are a variety of methods which can be used to produce libraries of potential LMP homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential LMP sequences. Methods for synthesizing degenerate oligonucleotides are known in the art (see, e.g., Narang 1983, Tetrahedron 39:3; Itakura et al. 1984, Annu Rev. Biochem. 53:323; Itakura et al. 1984, Science 198:1056; Ike et al. 1983, Nucleic Acids Res. 11:477).

In addition, libraries of fragments of the LMP coding sequences can be used to generate a variegated population of LMP fragments for screening and subsequent selection of homologues of a LMP. In one embodiment, a library of coding sequence fragments can be generated by treating a double stranded PCR fragment of a LMP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the LMP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of LMP homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify LMP homologues (Arkin & Yourvan 1992, Proc. Natl. Acad. Sci. USA 89:7811-7815; Delgrave et al. 1993, Protein Engineering 6:327-331).

In another embodiment, cell based assays can be exploited to analyze a variegated LMP library, using methods well known in the art.

The nucleic acid molecules, proteins, protein homologues, fusion proteins, primers, vectors, and host cells described herein can be used in one or more of the following methods: identification of *Arabidopsis thaliana* and related organisms; mapping of genomes of organisms related to *Arabidopsis thaliana*; identification and localization of *Arabidopsis thaliana* sequences of interest; evolutionary studies; determination of LMP regions required for function; modulation of a LMP activity; modulation of the metabolism of one or more cell functions; modulation of the transmembrane transport of one or more compounds; and modulation of seed storage compound accumulation.

The plant *Arabidopsis thaliana* represents one member of higher (or seed) plants. It is related to other plants such as *Brassica napus* or soybean which require light to drive photosynthesis and growth. Plants like *Arabidopsis thaliana* and *Brassica napus* share a high degree of homology on the DNA sequence and polypeptide level, allowing the use of heterologous screening of DNA molecules with probes evolving from other plants or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of *Arabidopsis* genomes, or of genomes of related organisms.

The LMP nucleic acid molecules of the invention have a variety of uses. First, they may be used to identify an organism as being *Arabidopsis thaliana* or a close relative thereof. Also, they may be used to identify the presence of *Arabidopsis thaliana* or a relative thereof in a mixed population of microorganisms. The invention provides the nucleic acid sequences of a number of *Arabidopsis thaliana* genes; by probing the extracted genomic DNA of a culture of a unique or mixed population of microorganisms under stringent conditions with a probe spanning a region of an *Arabidopsis thaliana* gene which is unique to this organism, one can ascertain whether this organism is present.

Further, the nucleic acid and protein molecules of the invention may serve as markers for specific regions of the genome. This has utility not only in the mapping of the genome, but also for functional studies of *Arabidopsis thaliana* proteins. For example, to identify the region of the genome to which a particular *Arabidopsis thaliana* DNA-binding protein binds, the *Arabidopsis thaliana* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *Arabidopsis thaliana*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related plants.

The LMP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the LMP nucleic acid molecules of the invention may result in the production of LMPs having functional differences from the wild-type LMPs. These proteins may be improved in efficiency or activity, may be present in greater numbers in the cell than is usual, or may be decreased in efficiency or activity.

There are a number of mechanisms by which the alteration of a LMP of the invention may directly affect the accumulation of seed storage compounds. In the case of plants expressing LMPs, increased transport can lead to altered accumulation of compounds and/or solute partitioning within the plant tissue and organs which ultimately could be used to affect the accumulation of one or more seed storage compounds during seed development. An example is provided by Mitsukawa et al. (1997, Proc. Natl. Acad. Sci. USA 94:7098-7102), where over expression of an *Arabidopsis* high-affinity phosphate transporter gene in tobacco cultured cells enhanced cell growth under phosphate-limited conditions. Phosphate availability also affects significantly the production of sugars and metabolic intermediates (Hurry et al. 2000, Plant J. 24:383-396) and the lipid composition in leaves and roots (Härtel et al. 2000, Proc. Natl. Acad. Sci. USA 97:10649-10654). Likewise, the activity of the plant ACCase has been demonstrated to be regulated by phosphorylation (Savage & Ohlrogge 1999, Plant J. 18:521-527) and alterations in the activity of the kinases and phosphatases (LMPs) that act on the ACCase could lead to increased or decreased levels of seed lipid accumulation. Moreover, the presence of lipid kinase activities in chloroplast envelope membranes suggests that signal transduction pathways and/or membrane protein regulation occur in envelopes (see, e.g., Müller et al. 2000, J. Biol. Chem. 275:19475-19481 and literature cited therein). The ABI1 and ABI2 genes encode two protein serine/threonine phosphatases 2C, which are regulators in abscisic acid signaling pathway, and thereby in early and late seed development (e.g. Merlot et al. 2001, Plant J. 25:295-303).

The present invention also provides antibodies which specifically bind to an LMP-polypeptide, or a portion thereof, as encoded by a nucleic acid disclosed herein or as described herein. Antibodies can be made by many well-known methods (see, e.g. Harlow and Lane, "Antibodies; A Laboratory Manual" Cold Spring Harbor Laboratory, Cold Spring Harbor, N.Y., 1988). Briefly, purified antigen can be injected into an animal in an amount and in intervals sufficient to elicit an immune response. Antibodies can either be purified directly, or spleen cells can be obtained from the animal. The cells can then be fused with an immortal cell line and screened for antibody secretion. The antibodies can be used to screen nucleic acid clone libraries for cells secreting the antigen. Those positive clones can then be sequenced (see, for example, Kelly et al. 1992, Bio/Technology 10:163-167; Bebbington et al. 1992, Bio/Technology 10:169-175).

The phrase "selectively binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application, various publications are referenced. The disclosures of all of these publications and those references cited within those publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and Examples be considered as exemplary only, with a true scope and spirit of the invention being indicated by the claims included herein.

EXAMPLES

Example 1

General Processes a) General Cloning Processes:

Cloning processes such as, for example, restriction cleavages, agarose gel electrophoresis, purification of DNA fragments, transfer of nucleic acids to nitrocellulose and nylon membranes, linkage of DNA fragments, transformation of *Escherichia coli* and yeast cells, growth of bacteria and sequence analysis of recombinant DNA were carried out as described in Sambrook et al. (1989, Cold Spring Harbor Laboratory Press: ISBN 0-87969-309-6) or Kaiser, Michaelis and Mitchell (1994, "Methods in Yeast Genetics", Cold Spring Harbor Laboratory Press: ISBN 0-87969-451-3).

b) Chemicals:

The chemicals used were obtained, if not mentioned otherwise in the text, in p.a. quality from the companies Fluka (Neu-Ulm), Merck (Darmstadt), Roth (Karlsruhe), Serva (Heidelberg) and Sigma (Deisenhofen). Solutions were prepared using purified, pyrogen-free water, designated as $H_2O$ in the following text, from a Milli-Q water system water purification plant (Millipore, Eschborn). Restriction endonucleases, DNA-modifying enzymes and molecular biology kits were obtained from the companies AGS (Heidelberg), Amersham (Braunschweig), Biometra (Göttingen), Boehringer (Mannheim), Genomed (Bad Oeynnhausen), New England Biolabs (Schwalbach/Taunus), Novagen (Madison, Wis., USA), Perkin-Elmer (Weiterstadt), Pharmacia (Freiburg), Qiagen (Hilden) and Stratagene (Amsterdam, Netherlands). They were used, if not mentioned otherwise, according to the manufacturer's instructions.

c) Plant Material:

For this study, in one series of experiments, root material of wild-type and pickle mutant plants of *Arabidopsis thaliana* were used. The pkl mutant was isolated from an ethyl methanesulfonate-mutagenized population of the Columbia ecotype as described (Ogas et al. 1997, Science 277:91-94; Ogas et al. 1999, Proc. Natl. Acad. Sci. USA 96:13839-13844). In other series of experiments, siliques of individual ecotypes of *Arabidopsis thaliana* and of selected *Arabidopsis* phytohormone mutants were used. Seeds were obtained from the *Arabidopsis* stock center.

d) Plant Growth:

Plants were either grown on Murashige-Skoog medium as described in Ogas et al. (1997, Science 277:91-94; 1999, Proc. Natl. Acad. Sci. USA 96:13839-13844) or on soil under standard conditions as described in Focks & Benning (1998, Plant Physiol. 118:91-101).

Example 2

Total DNA Isolation from Plants

The details for the isolation of total DNA relate to the working up of one gram fresh weight of plant material.

CTAB buffer: 2% (w/v) N-cethyl-N,N,N-trimethylammonium bromide (CTAB); 100 mM Tris HCl pH 8.0; 1.4 M NaCl; 20 mM EDTA. N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 μl of N-laurylsarcosine buffer, 20 μl of β-mercaptoethanol and 10 μl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000 g and RT for 15 min in each case. The DNA was then precipitated at −70° C. for 30 min using ice-cold isopropanol. The precipitated DNA was sedimented at 4° C. and 10,000 g for 30 min and resuspended in 180 μl of TE buffer (Sambrook et al. 1989, Cold Spring Harbor Laboratory Press: ISBN 0-87969-309-6). For further purification, the DNA was treated with NaCl (1.2 M final concentration) and precipitated again at −70° C. for 30 min using twice the volume of absolute ethanol. After a washing step with 70% ethanol, the DNA was dried and subsequently taken up in 50 μl of $H_2O$+RNAse (50 mg/ml final concentration). The DNA was dissolved overnight at 4° C. and the RNAse digestion was subsequently carried out at 37° C. for 1 h. Storage of the DNA took place at 4° C.

Example 3

Isolation of Total RNA and Poly-(A)+ RNA from Plants

For the investigation of transcripts, both total RNA and poly-(A)+ RNA were isolated. RNA is isolated from siliques of *Arabidopsis* plants according to the following procedure: RNA Preparation from *Arabidopsis* Seeds—"Hot" Extraction:

1. Buffers, Enzymes and Solution
   2M KCl
   Proteinase K
   Phenol (for RNA)
   Chloroform:Isoamylalcohol
   (Phenol:choloroform 1:1; pH adjusted for RNA)
   4 M LiCl, DEPC-treated
   DEPC-treated water
   3M NaOAc, pH 5, DEPC-treated
   Isopropanol
   70% ethanol (made up with DEPC-treated water)
   Resuspension buffer: 0.5% SDS, 10 mM Tris pH 7.5, 1 mM EDTA made up
with
   DEPC-treated water as this solution can not be DEPC-treated
   Extraction Buffer:
   0.2M Na Borate
   30 mM EDTA
   30 mM EGTA
   1% SDS (250 µl of 10% SDS-solution for 2.5 ml buffer)
   1% Deoxycholate (25 mg for 2.5 ml buffer)
   2% PVPP (insoluble—50 mg for 2.5 ml buffer)
   2% PVP 40K (50 mg for 2.5 ml buffer)
   10 mM DTT
   100 mM β-Mercaptoethanol (fresh, handle under fume hood—use 35 µl of 14.3M solution for 5 ml buffer)
2. Extraction
   Heat extraction buffer up to 80° C. Grind tissue in liquid nitrogen-cooled mortar, transfer tissue powder to 1.5 ml tube. Tissue should kept frozen until buffer is added so transfer the sample with pre-cooled spatula and keep the tube in liquid nitrogen all time. Add 350 µl preheated extraction buffer (here for 100 mg tissue, buffer volume can be as much as 500 µl for bigger samples) to tube, vortex and heat tube to 80° C. for ~1 min. Keep then on ice. Vortex sample, grind additionally with electric mortar.
3. Digestion
   Add Proteinase K (0.15 mg/100 mg tissue), vortex and keep at 37° C. for one hour.
4. First Purification
   Add 27 µl 2M KCl. Chill on ice for 10 min. Centrifuge at 12.000 rpm for 10 minutes at room temperature. Transfer supernatant to fresh, RNAase-free tube and do one phenol extraction, followed by a choloroform:isoamylalcohol extraction. Add 1 vol. isopropanol to supernatant and chill on ice for 10 min Pellet RNA by centrifugation (7000 rpm for 10 min at RT). Resolve pellet in 1 ml 4M LiCl by 10 to 15 min vortexing. Pellet RNA by 5 min centrifugation.
5. Second Purification
   Resuspend pellet in 50 µl Resuspension buffer. Add 500 µl phenol and vortex. Add 250 µl chloroform:isoamylalcohol and vortex. Spin for 5 min. and transfer supernatant to fresh tube. Repeat choloform:isoamylalcohol extraction until interface is clear. Transfer supernatant to fresh tube and add 1/10 vol 3M NaOAc, pH 5 and 600 µl isopropanol. Keep at −20 for 20 min or longer. Pellet RNA by 10 min centrifugation. Wash pellet once with 70% ethanol. Remove all remaining alcohol before resolving pellet with 15 to 20 µl DEPC-water. Determine quantity and quality by measuring the absorbance of a 1:200 dilution at 260 and 280 nm. 40 µg RNA/ml=1OD$_{260}$ RNA from roots of wild-type and the pickle mutant of *Arabidopsis* was isolated as described (Ogas et al. 1997, Science 277:91-94; Ogas et al. 1999, Proc. Natl. Acad. Sci. USA 96:13839-13844).

The mRNA was prepared from total RNA, using the Amersham Pharmacia Biotech mRNA purification kit, which utilizes oligo(dT)-cellulose columns.

Isolation of Poly-(A)+ RNA was isolated using Dyna Beads® (Dynal, Oslo, Norway) following the instructions of the manufacturer's protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

Example 4 cDNA Library Construction

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 h), 16° C. (1 h) and 22° C. (1 h). The reaction was stopped by incubation at 65° C. (10 min) and subsequently transferred to ice. Double stranded DNA molecules were blunted by T4-DNA-polymerase (Roche, Mannheim) at 37° C. (30 min). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 min). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 5

Identification of LMP Genes of Interest

The pickle *Arabidopsis* mutant was used to identify LMP-encoding genes. The pickle mutant accumulates seed storage compounds, such as seed storage lipids and seed storage proteins, in the root tips (Ogas et al. 1997, Science 277:91-94; Ogas et al. 1999, Proc. Natl. Acad. Sci. USA 96:13839-13844). mRNA isolated from roots of wild-type and pickle plants was used to create a subtracted and normalized cDNA library (SSH library, see example 4) containing cDNAs that are only present in the pickle roots, but not in the wild-type roots. Clones from the SSH library were spotted onto nylon membranes and hybridized with radio-labeled pickle or wild-type root mRNA to ascertain that the SSH clones were more abundant in pickle roots compared to wild-type roots. These SSH clones were randomly sequenced and the sequences were annotated using the annotation program PedantPro (see example 11). Based on the expression levels and on these initial functional annotations (see Table 3), clones from the SSH library were identified as potential LMP-encoding genes.

To identify additional potential gene targets from the *Arabidopsis* pickle mutant, the MPSS RNA expression profiling technology of Lynx Therapeutics Inc. was used (Brenner et al. 2000 Nature Biotechnology 18:630-634. Gene expression analysis by massively parallel signature sequencing (MPSS) on microbead arrays). The MPSS technology enables the quantitation of the abundance of mRNA transcripts in mRNA samples and was used to obtain expression profiles of wild-type and pickle root mRNAs. RNA was harvested from roots of 10 day old wild-type and pkl mutant seedlings that were grown on a defined medium on Petri plates. Candidate genes were selected based on the significant upregulation of their expression levels in pickle roots compared to wild-type roots. Since the pickle root exhibits various embryonic phenotypes such as the accumulation of seed storage lipids and proteins the upregulation of genes in the pickle root implied that the same genes could play important roles in the regulation of seed development and the accumulation of seed storage compounds in developing seeds.

TABLE 3

Putative LMP Functions

| Sequence code | Function | ORF position | SEQ ID NO: |
|---|---|---|---|
| AT004002024 | Per1 gene; peroxiredoxin | 1-648 | 1 |
| AT004004054 | Enoyl-CoA hydratase | 1-720 | 3 |
| AT004005069 | similarity to phosphatidylcholine-sterol O-acyltransferase (EC 2.3.1.43) precursor | 1-1995 | 5 |
| AT004009021 | Plastidic dihydroxyacetone 3-phosphate reductase | 1-1200 | 7 |
| Pk109 | putative protein | 1-1173 | 9 |
| Pk109-1 | Putative protein | 1-843 | 11 |
| Pk110 | phosphoenolpyruvate carboxykinase (ATP)-like protein | 1-2013 | 13 |
| Pk111 | hypothetical protein | 1-2337 | 15 |
| Pk111-1 | hypothetical protein | 1-1667 | 17 |
| Pk113 | putative isocitrate lyase | 1-1719 | 19 |
| Pk114 | unknown protein | 1-894 | 21 |
| Pk116 | acyl carrier protein 1 precursor (ACP) | 1-411 | 23 |
| Pk117 | inorganic pyrophosphatase - like protein | 1-900 | 25 |
| Pk118 | sucrose synthase | 1-2415 | 27 |
| Pk118-1 | sucrose synthase | 1-2391 | 29 |
| Pk120 | pyruvate kinase | 1-1530 | 31 |

TABLE 4

Grouping of LMPs based on Functional protein domains

| Functional category | SEQ ID: | SEQ Code: | Functional domain | Domain position |
|---|---|---|---|---|
| Antioxidant | 1 | AT004002024 | AhpC-TSA familyAlkyl Hydroperoxide peroxidases AhpC, Thiol-specific antioxidant protein TSA | 6-152 |
| Beta-oxidation | 3 | AT004004054 | Enoyl-CoA hydratase/isomerase | 13-181 |
| Acyltransferase | 5 | AT004005069 | lecithin: cholesterol acyltransferase (LCAT) | 103-627 |
| Dehydrogenase | 7 | AT004009021 | NAD-dependent glycerol-3-phosphate dehydrogenase | 54-396 |
| Dehydrogenase | 25 | Pk117 | UDP-glucose/GDP-mannose dehydrogenase | 36-45 |
| ATP synthase | 21 | Pk114 | ATP synthase (E/31 kDa) subunit | 74-95 |
| Kinase | 13 | Pk110 | Phosphoenolpyruvate carboxykinase | 147-618 |
| Kinase | 9 | Pk109 | Cytidilate kinase | 200-234 |
| Kinase | 11 | Pk109-1 | Cytidilate kinase | 165-199 |
| Kinase | 23 | Pk116 | Polyphospate kinase | 76-126 |
| Kinase | 31 | Pk120 | Pyruvate kinase | 16-365 |
| Isocitrate lyase | 19 | Pk113 | Isocitrate lyase | 18-548 |
| Sucrose synthase | 27 | Pk118 | Sucrose synthase | 11-551 |
| Sucrose synthase | 29 | Pk118-1 | Sucrose synthase | 2-543 |
| Membrane-associated | 15 | Pk111 | Ca-activated BK potassium channel α subunit | 315-330 |
| Membrane-associated | 15 | Pk111 | Anion-transporting ATPase | 402-413 |
| Membrane-associated | 17 | Pk111-1 | Ca-activated BK potassium channel α subunit | 93-108 |
| Membrane-associated | 17 | Pk111-1 | Anion-transporting ATPase | 180-191 |

Classification of the proteins was done by Blasting against the BLOCKS database (S. Henikoff & J. G. Henikoff, "Protein family classification based on searching a database of blocks", Genomics 19:97-107 (1994)).

Example 6

Cloning of Full-Length cDNAs and Binary Plasmids for Plant Transformation

RACE-PCR to Determine Full-Length Sequences

Full-length sequences of the *Arabidopsis thaliana* cDNAs that were identified in the SSH library and by MPSS RNA expression profiling were isolated by RACE PCR using the SMART RACE cDNA amplification kit from Clontech allowing both 5'- and 3' rapid amplification of cDNA ends (RACE). The isolation of first-strand cDNAs and the RACE PCR protocol used were based on the manufacturer's conditions. The RACE product fragments were extracted from agarose gels with a QIAquick® Gel Extraction Kit (Qiagen) and ligated into the TOPO® pCR 2.1 vector (Invitrogen) following manufacturer's instructions. Recombinant vectors were transformed into TOP10 cells (Invitrogen) using standard conditions (Sambrook et al. 1989). Transformed cells were grown overnight at 37° C. on LB agar containing 50 µg/ml kanamycin and spread with 40 µl of a 40 mg/ml stock solution of X-gal in dimethylformamide for blue-white selection. Single white colonies were selected and used to inoculate 3 ml of liquid LB containing 50 µg/ml kanamycin and grown overnight at 37° C. Plasmid DNA was extracted using the QIAprep® Spin Miniprep Kit (Qiagen) following manufacturer's instructions. Subsequent analyses of clones and restriction mapping was performed according to standard molecular biology techniques (Sambrook et al. 1989). The sequences obtained from the RACE reactions were compiled to give the nucleotide sequences for the LMP genes (SEQ ID NOs: 1, 3, 5, 7, 9, 11, 13, 15, 17, 19, 21, 23, 25, 27, 29 and 31).

RT-PCR and Cloning of *Arabidopsis thaliana* LMP Genes

Full-length LMP cDNAs were isolated by RT-PCR from *Arabidopsis thaliana* RNA. The synthesis of the first strand cDNA was achieved using AMV Reverse Transcriptase (Roche, Mannheim, Germany). The resulting single-stranded cDNA was amplified via Polymerase Chain Reaction (PCR) utilizing two gene-specific primers. The conditions for the reaction were standard conditions with Expand High Fidelity PCR system (Roche). The parameters for the reaction were: five minutes at 94° C. followed by five cycles of 40 seconds at 94° C., 40 seconds at 50° C. and 1.5 minutes at 72° C. This was followed by thirty cycles of 40 seconds at 94° C., 40 seconds at 65° C. and 1.5 minutes at 72° C. The fragments generated under these RT-PCR conditions were analyzed by agarose gel electrophoresis to make sure that PCR products of the expected length had been obtained.

Full-length LMP cDNA were isolated by using synthetic oligonucleotide primers (MWG-Biotech) designed based on the LMP gene specific DNA sequence that was determined by EST sequencing and by sequencing of RACE PCR products. For SEQ ID NO:1, SEQ ID NO:5, and SEQ ID NO:7, 5' PCR primers contained a Not1 restriction site 5' upstream of the ATG start codon and a Not1 restriction site 3' downstream of the stop codon. In the case of SEQ ID NO:3 PCR primers contained a BamHI and a Xba1 restriction site, respectively. All other 5' PCR primers ("forward primer", F) contained an AscI restriction site 5' upstream of the ATG start codon. All 3' PCR primers ("reverse primers", R) contained a PacI restriction site 3' downstream of the stop codon. The restriction sites were added so that the RT-PCR amplification products could be cloned into the AscI and PacI restriction sites located in the multiple cloning site of the binary vector pBPS-GB1. The first 2 nucleotides are used as spacers so the restriction enzymes cut properly. The following "forward" (F) and "reverse" (R) primers were used to amplify the full-length *Arabidopsis thaliana* cDNAs by RT-PCR using RNA from *Arabidopsis thaliana* as original template:

```
For amplification of SEQ ID NO: 1
AT004002024F
                                       (SEQ ID NO: 33)
(5'-ATAAGAATGCGGCCGCATGCCAGGGATCACACTAG-3')

AT004002024R
                                       (SEQ ID NO: 34)
(5'-ATAAGAATGCGGCCGCTCAAGAGACCTCTGTGTGA-3')

For amplification of SEQ ID NO: 3
AT004004054F
                                       (SEQ ID NO: 35)
(5'-GCGGATCCAGAGAAATGTGTTCATTAGAG-3')

AT004004054R
                                       (SEQ ID NO: 36)
(5'-CGTCTAGAGTTCTAAAGTTTAGATCCAGT-3')

For amplification of SEQ ID NO: 5
AT004005069F
                                       (SEQ ID NO: 37)
(5'-ATAAGAATGCGGCCGCATGTCTCCACTTCTCCGGTTTAG-3')

AT004005069R
                                       (SEQ ID NO: 38)
(5'-ATAAGAATGCGGCCGCTCACAACTTGATGCTAATTC-3')

For amplification of SEQ ID NO: 7
AT004009021F
                                       (SEQ ID NO: 39)
(5'-ATAAGAATGCGGCCGCATGCGCTTCCGATCATTCTTCTTCTCC
TCCTCTATC-3')

AT004009021R
                                       (SEQ ID NO: 40)
(3'-ATAAGAATGCGGCCGCTTATAGTTTGTTCTCGCGG-5')

For amplification of SEQ ID NO: 9
Pk109F
                                       (SEQ ID NO: 41)
(5'-ATGGCGCGCCATGTTGCCCAGATTAGCTCGAGTCG-3')

pk109R
                                       (SEQ ID NO: 42)
(5'-GCTTAATTAACTAACAGCTAGCACATTCCCTTGTG-3')

For amplification of SEQ ID NO: 11
Pk109F
                                       (SEQ ID NO: 43)
(5'-ATGGCGCGCCATGTTGCCCAGATTAGCTCGAGTCG-3')

pk109R
                                       (SEQ ID NO: 44)
(5'-GCTTAATTAACTAACAGCTAGCACATTCCCTTGTG-3')

For amplification of SEQ ID NO: 13
Pk110F
                                       (SEQ ID NO: 45)
(5'-ATGGCGCGCCATGTCGGCCGGTAACGGAAATGCTAC-3')

pk110R
                                       (SEQ ID NO: 46)
(5'-GCTTAATTAACTAAAAGATAGGACCAGCAGCGAG-3')

For amplification of SEQ ID NO: 15
Pk111F
                                       (SEQ ID NO: 47)
(5'-ATGGCGCGCCATGGTTTCGTTTACGGGTTTCGC-3')
```

-continued pk111R
(SEQ ID NO: 48)
(5'-GCTTAATTAATCAAGGTCCTCTCATCTTTTCAACA-3')

For amplification of SEQ ID NO: 17
Pk111F
(SEQ ID NO: 49)
(5'-ATGGCGCGCCATGGTTTCGTTTACGGGTTTCGC-3')

pk111R
(SEQ ID NO: 50)
(5' -GCTTAATTAATCAAGGTCCTCTCATCTTTTCAACA-3')

For amplification of SEQ ID NO: 19
Pk113F
(SEQ ID NO: 51)
(5'-ATGGCGCGCCAAGACTAACATGGAAATTGATGGCCG-3')

pk113R
(SEQ ID NO: 52)
(5'-GCTTAATTAACTTCTACCGGGTTTTTTCACTACG-3')

For amplification of SEQ ID NO: 21
Pk114F
(SEQ ID NO: 53)
(5'-ATGGCGCGCCATGGGGTTAGAGAGGAAAGTGTACGG-3')

pk114R
(SEQ ID NO: 54)
(5'-GCTTAATTAATCAGAGCTCAGCATCATCGTCGGT-3')

For amplification of SEQ ID NO: 23
Pk116F
(SEQ ID NO: 55)
(5'-ATGGCGCGCCATGGCGACTCAATTCAGCGCTTC-3')

pk116R
(SEQ ID NO: 56)
(5'-GCTTAATTAATTACTTCTTCTCGTTGATGAGCTCTTC-3')

For amplification of SEQ ID NO: 25
Pk117F
(SEQ ID NO: 57)
(5'-ATGGCGCGCCATGGCGGCTACTAGAGTGTTAACTG-3')

pk117R
(SEQ ID NO: 58)
(5'-GCTTAATTAATCAGTAAAGTGAAAGGTCTCCAGCA-3')

For amplification of SEQ ID NO: 27
Pk118F
(SEQ ID NO: 59)
(5'-ATGGCGCGCCAACAATGGCGTCTTTCTTTGATCTCG-3')

pk118R
(SEQ ID NO:60)
(5'-GCTTAATTAATCAGTTCTCATCTGTTGCCAG-3')

For amplification of SEQ ID NO: 29
Pk118F
(SEQ ID NO: 61)
(5'-ATGGCGCGCCAACAATGGCGTCTTTCTTTGATCTCG-3')

pk118R
(SEQ ID NO: 62)
(5'-GCTTAATTAATCAGTTCTCATCTGTTGCCAG-3')

For amplification of SEQ ID NO: 31
Pk120F
(SEQ ID NO: 63)
(5' -ATGGCGCGCCATGTCGAACATAGACATAGAAGGGATC-3')

pk120R
(SEQ ID NO: 64)
(5'-GCTTAATTAATCACTTAACCACACAGATCTTAATAACTG-3')

Example 7

*Agrobacterium* Mediated Plant Transformation

For plant transformation, binary vectors such as pBinAR can be used (Höfgen & Willmitzer 1990, Plant Sci. 66: 221-230). Plant binary vectors encoding LMP genes were constructed with the aim to achieve the overexpression of functionally active proteins in transgenic plants. All LMP gene candidates were cloned into the plant binary vector pBPS-GB1 vector. The binary vector contains a selectable marker gene driven under the control of the AtAct2-I promoter (Ann Y-Q et al., 1996, Plant Journal 10:107-121) and a USP (unknown seed protein, Bäumlein et al., Mol Gen Genet. 225: 459-467, 1991) seed-specific promoter driving the candidate LMP gene with the NOSpA terminator. Full-length LMP cDNAs were cloned into AscI and PacI restriction sites in the multiple cloning site of pBPS-GB1 in sense orientation behind the USP seed-specific promoter. The recombinant binary vectors (based on pBPS-GB1) containing the genes of interest were transformed into *E. coli* Top10 cells (Invitrogen) using standard conditions. Transformed cells were selected for on LB agar containing an antibiotic and grown overnight at 37° C. Plasmid DNA was extracted using the QIAprep Spin Miniprep Kit (Qiagen) following manufacturer's instructions. Analysis of subsequent clones and restriction mapping was performed according to standard molecular biology techniques (Sambrook et al. 1989, Molecular Cloning, A Laboratory Manual. $2^{nd}$ Edition. Cold Spring Harbor Laboratory Press. Cold Spring Harbor, N.Y.). The nucleotide sequence of the inserted LMP genes was verified by "2+1" sequencing (the insert DNA was sequence by determining the nucleotide sequence of one DNA stand with two independent sequence reactions and the complementary DNA strand with on sequencing reaction according to the Bermuda convention). The full length sequences are shown as SEQ ID NOs: 1, 3, 5, 7, 9, 11, 13, 15, 17, 19, 21, 23, 25, 27, 29 and 31.

*Agrobacterium* mediated plant transformation with binary vectors encoding the LMP nucleic acids described herein was performed using standard transformation and regeneration techniques (Gelvin, Stanton B. & Schilperoort R. A, Plant Molecular Biology Manual, 2nd ed. Kluwer Academic Publ., Dordrecht 1995 in Sect., Ringbuc Zentrale Signatur: BT11-P; Glick, Bernard R. and Thompson, John E. Methods in Plant Molecular Biology and Biotechnology, S. 360, CRC Press, Boca Raton 1993).

The *Agrobacterium* mediated transformation of *Arabidopsis thaliana* was performed using the GV3 (pMP90) (Koncz & Schell, 1986, Mol. Gen. Genet. 204: 383-396) *Agrobacterium tumefaciens* strain. *Arabidopsis thaliana* ecotype Col-2 was grown and transformed according to standard conditions (Bechtold 1993, Acad. Sci. Paris. 316: 1194-1199; Bent et al. 1994, Science 265: 1856-1860). Kanamycin was used as antibiotic selection marker for *Agrobacterium* transformation. The presence and correct orientation of the LMP-encoding binary vectors in *Agrobacterium* cultures was verified by PCR using the LMP gene-specific primers described in example 6. For the plant transformation flowering *Arabidopsis* plants were dipped into the recombinant *Agrobacterium* cultures and allowed to go to seed. Transgenic *Arabidopsis* T1 plants were identified by growing the seeds on Petri plates containing the selection agent appropriate for the selection marker present on the T-DNA. Surviving healthy seedlings were transferred to soil and grown in a growth chamber under controlled conditions. T2 seeds were harvested from these T1 plants. The transgenic lines were propagated through successive generations and T2, T3 and T4 seeds were obtained. The segregation ratio of the presence or absence of the T-DNA was monitored in order to determine whether the lines contained single-locus or multi-locus insertions and whether the lines were homozygous or heterozygous for the T-DNA insertion. T2, T3 and T4 seeds were analyzed for seed oil content (see also example 8).

*Agrobacterium* mediated plant transformation is also applicable to *Brassica* and other crops. In particular, seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. The seed coats are removed and the seeds are air dried overnight in a half-open sterile Petri dish. During this period, the seeds lose approximately 85% of their water content. The seeds are then stored at room temperature in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and re-suspended in MS (Murashige & Skoog 1962, Physiol. Plant. 15: 473-497) medium supplemented with 100 µM acetosyringone. Bacteria cultures are incubated in this pre-induction medium for 2 hours at room temperature before use. The axis of soybean zygotic seed embryos at approximately 44% moisture content are imbibed for 2 hours at room temperature with the pre-induced *Agrobacterium* suspension culture. (The imbibition of dry embryos with a culture of *Agrobacterium* is also applicable to maize embryo axes). The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/l carbenicillin or 300 mg/l cefotaxime to kill the *agrobacteria*. The liquid medium is used to moisten the sterile filter paper. The embryos are incubated during 4 weeks at 25° C., under 440 µmol m$^{-2}$ sec$^{-1}$ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 440 µmol m$^{-2}$ s$^{-1}$ light intensity and 12 h photoperiod for about 80 days.

Samples of the primary transgenic plants (T$_0$) are analyzed by PCR to confirm the presence of T-DNA. These results are confirmed by Southern hybridization wherein DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labeled probe by PCR, and used as recommended by the manufacturer.

Transformation of soybean can be performed using for example a technique described in EP 424 047, U.S. Pat. No. 5,322,783 (Pioneer Hi-Bred International) or in EP 0397 687, U.S. Pat. No. 5,376,543 or U.S. Pat. No. 5,169,770 (University Toledo).

Example 8

Analysis of the Impact of Recombinant LMPs on the Production of a Desired Seed Storage Compound: Fatty Acid Production The total fatty acid content of *Arabidopsis* seeds was determined by saponification of seeds in 0.5 M KOH in methanol at 80° C. for 2 h followed by LC-MS analysis of the free fatty acids. Total fatty acid content of seeds of control and transgenic plants was measured with bulked seeds (usually 5 mg seed weight) of a single plant. Three different types of controls have been used: Col-2 and Col-0 (Columbia-2 and Columbia-0, the *Arabidopsis* ecotypes LMP gene of interest have been transformed in), C-24 (an *Arabidopsis* ecotype found to accumulate high amounts of total fatty acids in seeds) and GB1 (BPS empty, without LMP gene of interest, binary vector construct). The controls indicated in the tables below have been grown side by side with the transgenic lines. Differences in the total values of the controls are explained either by differences in the growth conditions, which were found to be very sensitive to small variations in the plant cultivation, or by differences in the standards added to quantify the fatty acid content. Because of the seed bulking all values obtained with T2 seeds and in part also with T3 seeds are the result of a mixture of homozygous (for the gene of interest) and heterozygous events, implying that these data underestimate the LMP gene effect.

TABLE 5

Determination of the T2 seed total fatty acid content of transgenic lines of AT004002024 (containing SEQ ID NO: 1).

| Genotype | g total fatty acids/ g seed weight |
|---|---|
| Pks002-1 transgenic seeds | 0.321 ± 0.009 |
| Pks002-7 transgenic seeds | 0.330 ± 0.005 |
| Pks002-8 transgenic seeds | 0.300 ± 0.029 |
| Pks002-10 transgenic seeds | 0.363 ± 0.013 |
| Pks002-16 transgenic seeds | 0.278 ± 0.013 |
| Col-0 wild-type seeds | 0.247 ± 0.008 |

Shown are the means (±standard deviation). (Average mean values are shown ± standard deviation, number of individual measurements per plant line: 12-18; Col-0 is the *Arabidopsis* ecotype the LMP gene has been transformed in)

TABLE 6

Determination of the T3 seed total fatty acid content of transgenic lines of AT004004054 (containing SEQ ID NO: 3).

| Genotype | g total fatty acids/ g seed weight |
|---|---|
| Pks001-22 (2-7) transgenic seeds | 0.379 ± 0.038 |
| Pks001-27 (2, 5, 8-9) transgenic seeds | 0.371 ± 0.053 |
| Pks001-39 (1, 2, 4-7) transgenic seeds | 0.333 ± 0.038 |
| Pks001-89 (1-7) transgenic seeds | 0.295 ± 0.036 |
| Pks001-106 (1-3, 5-7) transgenic seeds | 0.261 ± 0.040 |
| Col-0 wild-type seeds (1-8) | 0.284 ± 0.032 |

Shown are the means (±standard deviation) of individual plants (number in parenthesis).

TABLE 7

Determination of the T2 seed total fatty acid content of transgenic lines of AT004005069 (containing SEQ ID NO: 5 in antisense orientation).

| Genotype | g total fatty acids/ g seed weight |
| --- | --- |
| Pks004-1 transgenic seeds | 0.532 ± 0.014 |
| Pks004-3 transgenic seeds | 0.488 ± 0.013 |
| Pks004-4 transgenic seeds | 0.492 ± 0.016 |
| Pks004-18 transgenic seeds | 0.488 ± 0.012 |
| Pks004-20 transgenic seeds | 0.461 ± 0.011 |
| Pks004-21 transgenic seeds | 0.421 ± 0.035 |
| Col-0 wild-type seeds | 0.301 ± 0.026 |

Shown are the means (±standard deviation) of 18 individual plants, respectively.

TABLE 8

Determination of the T2 seed total fatty acid content of transgenic lines of AT004009021 (containing SEQ ID NO: 7).

| Genotype | g total fatty acids/ g seed weight |
| --- | --- |
| Pks003-3 transgenic seeds | 0.353 ± 0.019 |
| Pks003-4 transgenic seeds | 0.293 ± 0.046 |
| Pks003-8 transgenic seeds | 0.265 ± 0.073 |
| Pks003-16 transgenic seeds | 0.312 ± 0.021 |
| Pks003-17 transgenic seeds | 0.311 ± 0.026 |
| Pks003-18 transgenic seeds | 0.322 ± 0.023 |
| Col-0 wild-type seeds | 0.259 ± 0.048 |

Shown are the means (±standard deviation) of 10 individual plants.

TABLE 9

Determination of the T3 seed total fatty acid content of transgenic lines of pk109 (containing SEQ ID NO: 11).

| Genotype | g total fatty acids/ g seed weight |
| --- | --- |
| C-24 wild type seeds | 0.393 ± 0.047 |
| Col-2 wild type seeds | 0.351 ± 0.024 |
| GB-1 empty vector control | 0.350 ± 0.027 |
| Pk109-11 transgenic seeds | 0.377 ± 0.038 |
| Pk109-16 transgenic seeds | 0.384 ± 0.035 |
| Pk109-12 transgenic seeds | 0.384 ± 0.046 |

Shown are the means (±standard deviation) of 14-20 individual plants per line.

TABLE 10

Determination of the T2 seed total fatty acid content of transgenic lines of pk110 (containing SEQ ID NO: 13).

| Genotype | g total fatty acids/ g seed weight |
| --- | --- |
| C-24 wild type seeds | 0.405 ± 0.029 |
| Col-2 wild type seeds | 0.390 ± 0.019 |
| Pk110 (7, 9, 10, 11, 13, 19) transgenic seeds | 0.409 ± 0.016 |

Shown are the means (±standard deviation) of 6-10 individual plants per line.

TABLE 11

Determination of the T2 seed total fatty acid content of transgenic lines of pk111-1 (containing SEQ ID NO: 17).

| Genotype | g total fatty acids/ g seed weight |
| --- | --- |
| C-24 wild type seeds | 0.405 ± 0.029 |
| Col-2 wild type seeds | 0.390 ± 0.019 |
| Pk111 (1, 2, 4, 5, 6, 8, 14, 17, 19) transgenic seeds | 0.417 ± 0.015 |

Shown are the means (±standard deviation) of 8-10 individual plants per line.

TABLE 12

Determination of the T3 seed total fatty acid content of transgenic lines of pk114 (containing SEQ ID NO: 21).

| Genotype | g total fatty acids/ g seed weight |
| --- | --- |
| C-24 wild-type seeds | 0.435 ± 0.027 |
| Col-2 wild-type seeds | 0.398 ± 0.021 |
| GB-1 empty vector control | 0.412 ± 0.027 |
| Pk114-16 transgenic seeds | 0.430 ± 0.036 |
| Pk114-19 transgenic seeds | 0.419 ± 0.034 |
| Pk114-19 transgenic seeds | 0.438 ± 0.028 |

Shown are the means (±standard deviation) of 12-19 individual plants per line.

TABLE 13

Determination of the T2 seed total fatty acid content of transgenic lines of pk116 (containing SEQ ID NO: 23).

| Genotype | g total fatty acids/ g seed weight |
| --- | --- |
| C-24 wild-type seeds | 0.405 ± 0.029 |
| Col-2 wild-type seeds | 0.390 ± 0.019 |
| Pk116 (2, 4, 5, 11, 13, 16) transgenic seeds | 0.409 ± 0.013 |

Shown are the means (±standard deviation) of 6-10 individual plants per line.

TABLE 14

Determination of the T3 seed total fatty acid content of transgenic lines of pk117-1 (containing SEQ ID NO: 25).

| Genotype | g total fatty acids/ g seed weight |
| --- | --- |
| C-24 wild type seeds | 0.442 ± 0.022 |
| Col-2 wild type seeds | 0.407 ± 0.028 |
| GB-1 empty vector control | 0.403 ± 0.023 |
| Pk117-10 transgenic seeds | 0.421 ± 0.011 |
| Pk117-3 transgenic seeds | 0.424 ± 0.031 |

Shown are the means (±standard deviation) of bulked seeds (5 mg) of 16-19 individual plants per line.

TABLE 15

Determination of the T2 seed total fatty acid content of transgenic lines of pk120 (containing SEQ ID NO: 31).

| Genotype | g total fatty acids/ g seed weight |
| --- | --- |
| C-24 wild type seeds | 0.408 ± 0.026 |
| Col-2 wild type seeds | 0.363 ± 0.023 |
| Pk120 (1, 5, 6, 10, 11, 16) transgenic seeds | 0.397 ± 0.010 |

Shown are the means (±standard deviation) of 6-12 individual plants per line.

Example 9

Analysis of the Impact of Recombinant Proteins on the Production of a Desired Seed Storage Compound The effect of the genetic modification in plants on a desired seed storage compound (such as a sugar, lipid or fatty acid) can be assessed by growing the modified plant under suitable conditions and analyzing the seeds or any other plant organ for increased production of the desired product (i.e., a lipid or a fatty acid). Such analysis techniques are well known to one skilled in the art, and include spectroscopy, thin layer chromatography, staining methods of various kinds, enzymatic and microbiological methods, and analytical chromatography such as high performance liquid chromatography (see, for example, Ullman 1985, Encyclopedia of Industrial Chemistry, vol. A2, pp. 89-90 and 443-613, VCH: Weinheim; Fallon, A. et al. 1987, Applications of HPLC in Biochemistry in: Laboratory Techniques in Biochemistry and Molecular Biology, vol. 17; Rehm et al., 1993 Product recovery and purification, Biotechnology, vol. 3, Chapter III, pp. 469-714, VCH: Weinheim; Belter, P. A. et al., 1988 Bioseparations: downstream processing for biotechnology, John Wiley & Sons; Kennedy J. F. & Cabral J. M. S. 1992, Recovery processes for biological materials, John Wiley and Sons; Shaeiwitz J. A. & Henry J. D. 1988, Biochemical separations in: Ulmann's Encyclopedia of Industrial Chemistry, Separation and purification techniques in biotechnology, vol. B3, Chapter 11, pp. 1-27, VCH: Weinheim; and Dechow F. J. 1989).

Besides the above-mentioned methods, plant lipids are extracted from plant material as described by Cahoon et al. (1999, Proc. Natl. Acad. Sci. USA 96, 22:12935-12940) and Browse et al. (1986, Anal. Biochemistry 442:141-145). Qualitative and quantitative lipid or fatty acid analysis is described in Christie, William W., Advances in Lipid Methodology. Ayr/Scotland:Oily Press.—(Oily Press Lipid Library; Christie, William W., Gas Chromatography and Lipids. A Practical Guide—Ayr, Scotland: Oily Press, 1989 Repr. 1992.—IX, 307 S.—(Oily Press Lipid Library; and "Progress in Lipid Research, Oxford:Pergamon Press, 1 (1952)-16 (1977) Progress in the Chemistry of Fats and Other Lipids CODEN.

Unequivocal proof of the presence of fatty acid products can be obtained by the analysis of transgenic plants following standard analytical procedures: GC, GC-MS or TLC as variously described by Christie and references therein (1997 in: Advances on Lipid Methodology 4th ed.: Christie, Oily Press, Dundee, pp. 119-169; 1998). Detailed methods are described for leaves by Lemieux et al. (1990, Theor. Appl. Genet. 80:234-240) and for seeds by Focks & Benning (1998, Plant Physiol. 118:91-101).

Positional analysis of the fatty acid composition at the C-1, C-2 or C-3 positions of the glycerol backbone is determined by lipase digestion (see, e.g., Siebertz & Heinz 1977, Z. Naturforsch. 32c:193-205, and Christie 1987, Lipid Analysis $2^{nd}$ Edition, Pergamon Press, Exeter, ISBN 0-08-023791-6).

A typical way to gather information regarding the influence of increased or decreased protein activities on lipid and sugar biosynthetic pathways is for example via analyzing the carbon fluxes by labeling studies with leaves or seeds using $^{14}C$-acetate or $^{14}C$-pyruvate (see, e.g. Focks & Benning 1998, Plant Physiol. 118:91-101; Eccleston & Ohlrogge 1998, Plant Cell 10:613-621). The distribution of carbon-14 into lipids and aqueous soluble components can be determined by liquid scintillation counting after the respective separation (for example on TLC plates) including standards like $^{14}C$-sucrose and $^{14}C$-malate (Eccleston & Ohlrogge 1998, Plant Cell 10:613-621).

Material to be analyzed can be disintegrated via sonification, glass milling, liquid nitrogen and grinding or via other applicable methods. The material has to be centrifuged after disintegration. The sediment is re-suspended in distilled water, heated for 10 minutes at 100° C., cooled on ice and centrifuged again followed by extraction in 0.5 M sulfuric acid in methanol containing 2% dimethoxypropane for 1 hour at 90° C. leading to hydrolyzed oil and lipid compounds resulting in transmethylated lipids. These fatty acid methyl esters are extracted in petrolether and finally subjected to GC analysis using a capillary column (Chrompack, WCOT Fused Silica, CP-Wax-52 CB, 25 m, 0.32 mm) at a temperature gradient between 170° C. and 240° C. for 20 minutes and 5 min at 240° C. The identity of resulting fatty acid methylesters is defined by the use of standards available form commercial sources (i.e., Sigma).

In case of fatty acids where standards are not available, molecule identity is shown via derivatization and subsequent GC-MS analysis. For example, the localization of triple bond fatty acids is shown via GC-MS after derivatization via 4,4-Dimethoxy-oxazolin-Derivaten (Christie, Oily Press, Dundee, 1998).

A common standard method for analyzing sugars, especially starch, is published by Stitt M., Lilley R. Mc. C., Gerhardt R. and Heldt M. W. (1989, "Determination of metabolite levels in specific cells and subcellular compartments of plant leaves" Methods Enzymol. 174:518-552; for other methods see also Härtel et al. 1998, Plant Physiol. Biochem. 36:407-417 and Focks & Benning 1998, Plant Physiol. 118:91-101).

For the extraction of soluble sugars and starch, 50 seeds are homogenized in 500 µl of 80% (v/v) ethanol in a 1.5-ml polypropylene test tube and incubated at 70° C. for 90 min. Following centrifugation at 16,000 g for 5 min, the supernatant is transferred to a new test tube. The pellet is extracted twice with 500 µl of 80% ethanol. The solvent of the combined supernatants is evaporated at room temperature under a vacuum. The residue is dissolved in 50 µl of water, representing the soluble carbohydrate fraction. The pellet left from the ethanol extraction, which contains the insoluble carbohydrates including starch, is homogenized in 200 µl of 0.2 N KOH, and the suspension is incubated at 95° C. for 1 h to dissolve the starch. Following the addition of 35 µl of 1 N acetic acid and centrifugation for 5 min at 16,000 g, the supernatant is used for starch quantification.

To quantify soluble sugars, 10 µl of the sugar extract is added to 990 µl of reaction buffer containing 100 mM imidazole, pH 6.9, 5 mM $MgCl_2$, 2 mM NADP, 1 mM ATP, and 2 units 2 $ml^{-1}$ of Glucose-6-P-dehydrogenase. For enzymatic determination of glucose, fructose and sucrose, 4.5 units of hexokinase, 1 unit of phosphoglucoisomerase, and 2 µl of a saturated fructosidase solution are added in succession. The production of NADPH is photometrically monitored at a wavelength of 340 nm. Similarly, starch is assayed in 30 µl of the insoluble carbohydrate fraction with a kit from Boehringer Mannheim.

An example for analyzing the protein content in leaves and seeds can be found by Bradford M. M. (1976, "A rapid and sensitive method for the quantification of microgram quantities of protein using the principle of protein dye binding" Anal. Biochem. 72:248-254). For quantification of total seed protein, 15-20 seeds are homogenized in 250 µl of acetone in a 1.5-ml polypropylene test tube. Following centrifugation at 16,000 g, the supernatant is discarded and the vacuum-dried pellet is resuspended in 250 μl of extraction buffer containing 50 mM Tris-HCl, pH 8.0, 250 mM NaCl, 1 mM EDTA, and 1% (w/v) SDS. Following incubation for 2 h at 25° C., the homogenate is centrifuged at 16,000 g for 5 min and 200 ml of the supernatant will be used for protein measurements. In the assay, γ-globulin is used for calibration. For protein measurements, Lowry DC protein assay (Bio-Rad) or Bradford-assay (Bio-Rad) are used.

Enzymatic assays of hexokinase and fructokinase are performed spectrophotometrically according to Renz et al. (1993, Planta 190:156-165), of phosphoglucoisomerase, ATP-dependent 6-phosphofructokinase, pyrophosphate-dependent 6-phospho-fructokinase, Fructose-1,6-bisphosphate aldolase, triose phosphate isomerase, glyceral-3-P dehydrogenase, phosphoglycerate kinase, phosphoglycerate mutase, enolase and pyruvate kinase are performed according to Burrell et al. (1994, Planta 194:95-101) and of UDP-Glucose-pyrophosphorylase according to Zrenner et al. (1995, Plant J. 7:97-107).

Intermediates of the carbohydrate metabolism, like Glucose-1-phosphate, Glucose-6-phosphate, Fructose-6-phosphate, Phosphoenolpyruvate, Pyruvate, and ATP are measured as described in Härtel et al. (1998, Plant Physiol. Biochem. 36:407-417) and metabolites are measured as described in Jelitto et al. (1992, Planta 188:238-244).

In addition to the measurement of the final seed storage compound (i.e., lipid, starch or storage protein) it is also possible to analyze other components of the metabolic pathways utilized for the production of a desired seed storage compound, such as intermediates and side-products, to determine the overall efficiency of production of the compound (Fiehn et al. 2000, Nature Biotech. 18:1447-1161).

Example 10

Northern-Hybridization

For RNA hybridization, 20 μg of total RNA or 1 μg of poly-(A)+ RNA is separated by gel electrophoresis in 1.25% strength agarose gels using formaldehyde as described in Amasino (1986, Anal. Biochem. 152:304), transferred by capillary attraction using 10×SSC to positively charged nylon membranes (Hybond N+, Amersham, Braunschweig), immobilized by UV light and pre-hybridized for 3 hours at 68° C. using hybridization buffer (10% dextran sulfate w/v, 1 M NaCl, 1% SDS, 100 μg/ml of herring sperm DNA). The labeling of the DNA probe with the Highprime DNA labeling kit (Roche, Mannheim, Germany) is carried out during the pre-hybridization using alpha-$^{32}$P dCTP (Amersham, Braunschweig, Germany). Hybridization is carried out after addition of the labeled DNA probe in the same buffer at 68° C. overnight. The washing steps are carried out twice for 15 min using 2×SSC and twice for 30 min using 1×SSC, 1% SDS at 68° C. The exposure of the sealed filters is carried out at −70° C. for a period of 1 day to 14 days.

Example 11

DNA Sequencing and Computational Functional Analysis of SSH Library

The SSH cDNA library as described in Examples 4 and 5 was used for DNA sequencing according to standard methods, in particular by the chain termination method using the ABI PRISM Big Dye Terminator Cycle Sequencing Ready Reaction Kit (Perkin-Elmer, Weiterstadt, Germany). Random sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown E. coli cultures grown in Luria-Broth medium containing ampicillin (see Sambrook et al. (1989, Cold Spring Harbor Laboratory Press: ISBN 0-87969-309-6) on a Qiagene DNA preparation robot (Qiagen, Hilden) according to the manufacturer's protocols). Sequencing primers with the following nucleotide sequences were used:

| | |
|---|---|
| 5'-CAGGAAACAGCTATGACC-3' | (SEQ ID NO: 65) |
| 5'-CTAAAGGGAACAAAAGCTG-3' | (SEQ ID NO: 66) |
| 5'-TGTAAAACGACGGCCAGT-3' | (SEQ ID NO: 67) |

Sequences were processed and annotated using the software package EST-MAX commercially provided by Bio-Max (Munich, Germany). The program incorporates practically all bioinformatics methods important for functional and structural characterization of protein sequences. For reference see the pedant.mips.biochem.mpg.de web page.

The most important algorithms incorporated in EST-MAX are: FASTA: Very sensitive protein sequence database searches with estimates of statistical significance (Pearson W. R. 1990, Rapid and sensitive sequence comparison with FASTP and FASTA. Methods Enzymol. 183:63-98). BLAST: Very sensitive protein sequence database searches with estimates of statistical significance (Altschul S. F., Gish W., Miller W., Myers E. W. and Lipman D. J. Basic local alignment search tool. J. Mol. Biol. 215:403-410). PREDATOR: High-accuracy secondary structure prediction from single and multiple sequences. (Frishman & Argos 1997, 75% accuracy in protein secondary structure prediction. Proteins 27:329-335). CLUSTALW: Multiple sequence alignment (Thompson, J. D., Higgins, D. G. and Gibson, T. J. 1994, CLUSTAL W: improving the sensitivity of progressive multiple sequence alignment through sequence weighting, positions-specific gap penalties and weight matrix choice, Nucleic Acids Res. 22:4673-4680). TMAP: Transmembrane region prediction from multiply aligned sequences (Persson B. & Argos P. 1994, Prediction of transmembrane segments in proteins utilizing multiple sequence alignments, J. Mol. Biol. 237:182-192). ALOM2:Transmembrane region prediction from single sequences (Klein P., Kanehisa M., and DeLisi C. 1984, Prediction of protein function from sequence properties: A discriminant analysis of a database. Biochim. Biophys. Acta 787:221-226. Version 2 by Dr. K. Nakai). PROSEARCH: Detection of PROSITE protein sequence patterns. Kolakowski L. F. Jr., Leunissen J. A. M. and Smith J. E. 1992, ProSearch: fast searching of protein sequences with regular expression patterns related to protein structure and function. Biotechniques 13:919-921). BLIMPS: Similarity searches against a database of ungapped blocks (Wallace & Henikoff 1992, PATMAT:A searching and extraction program for sequence, pattern and block queries and databases, CABIOS 8:249-254. Written by Bill Alford).

Example 12

In Vivo Mutagenesis

In vivo mutagenesis of microorganisms can be performed by incorporation and passage of the plasmid (or other vector) DNA through E. coli or other microorganisms (e.g. Bacillus spp. or yeasts such as Saccharomyces cerevisiae) which are impaired in their capabilities to maintain the integrity of their genetic information. Typical mutator strains have mutations in the genes for the DNA repair system (e.g., mutHLS, mutD, mutT, etc.; for reference, see Rupp W. D. 1996, DNA repair mechanisms, in: *Escherichia coli* and *Salmonella*, p. 2277-2294, ASM: Washington.) Such strains are well known to those skilled in the art. The use of such strains is illustrated, for example, in Greener and Callahan 1994, Strategies 7:32-34. Transfer of mutated DNA molecules into plants is preferably done after selection and testing in microorganisms. Transgenic plants are generated according to various examples within the exemplification of this document.

Example 13

Assessment of the mRNA Expression and Activity of a Recombinant Gene Product in the Transformed Organism The activity of a recombinant gene product in the transformed host organism can be measured on the transcriptional or/and on the translational level. A useful method to ascertain the level of transcription of the gene (an indicator of the amount of mRNA available for translation to the gene product) is to perform a Northern blot (for reference see, for example, Ausubel et al. 1988, Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information at least partially demonstrates the degree of transcription of the transformed gene. Total cellular RNA can be prepared from plant cells, tissues or organs by several methods, all well-known in the art, such as that described in Bormann et al. (1992, Mol. Microbiol. 6:317-326).

To assess the presence or relative quantity of protein translated from this mRNA, standard techniques, such as a Western blot, may be employed (see, for example, Ausubel et al. 1988, Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or colorimetric label which may be readily detected. The presence and quantity of label observed indicates the presence and quantity of the desired mutant protein present in the cell.

The activity of LMPs that bind to DNA can be measured by several well-established methods, such as DNA band-shift assays (also called gel retardation assays). The effect of such LMP on the expression of other molecules can be measured using reporter gene assays (such as that described in Kolmar H. et al. 1995, EMBO J. 14:3895-3904 and references cited therein). Reporter gene test systems are well known and established for applications in both prokaryotic and eukaryotic cells, using enzymes such as beta-galactosidase, green fluorescent protein, and several others.

The determination of activity of lipid metabolism membrane-transport proteins can be performed according to techniques such as those described in Gennis R. B. (1989 Pores, Channels and Transporters, in Biomembranes, Molecular Structure and Function, Springer: Heidelberg, pp. 85-137, 199-234 and 270-322).

Example 14

In vitro Analysis of the Function of *Arabidopsis thaliana* Genes in Transgenic Plants The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M. & Webb, E. C. 1979, Enzymes. Longmans: London; Fersht, (1985) Enzyme Structure and Mechanism. Freeman: New York; Walsh (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, 3rd ed. Academic Press: New York; Bisswanger, H., (1994) Enzymkinetik, 2nd ed. VCH: Weinheim (ISBN 3527300325); Bergmeyer, H. U., Bergmeyer, J., Graβ1, M., eds. (1983-1986) Methods of Enzymatic Analysis, 3rd ed., vol. I-XII, Verlag Chemie: Weinheim; and Ullmann's Encyclopedia of Industrial Chemistry (1987) vol. A9, Enzymes. VCH: Weinheim, p. 352-363.

Example 15

Purification of the Desired Product from Transformed Organisms

An LMP can be recovered from plant material by various methods well known in the art. Organs of plants can be separated mechanically from other tissue or organs prior to isolation of the seed storage compound from the plant organ. Following homogenization of the tissue, cellular debris is removed by centrifugation and the supernatant fraction containing the soluble proteins is retained for further purification of the desired compound. If the product is secreted from cells grown in culture, then the cells are removed from the culture by low-speed centrifugation and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There are a wide array of purification methods known to the art and the preceding method of purification is not meant to be limiting. Such purification techniques are described, for example, in Bailey J. E. & Ollis D. F. 1986, Biochemical Engineering Fundamentals, McGraw-Hill: New York).

The identity and purity of the isolated compounds may be assessed by techniques standard in the art. These include high-performance liquid chromatography (HPLC), spectroscopic methods, staining methods, thin layer chromatography, analytical chromatography such as high performance liquid chromatography, NIRS, enzymatic assay, or microbiologically. Such analysis methods are reviewed in: Patek et al. (1994, Appl. Environ. Microbiol. 60:133-140), Malakhova et al. (1996, Biotekhnologiya 11:27-32) and Schmidt et al. (1998, Bioprocess Engineer 19:67-70), Ulmann's Encyclopedia of Industrial Chemistry (1996, Vol. A27, VCH: Weinheim, p. 89-90, p. 521-540, p. 540-547, p. 559-566, 575-581 and p. 581-587) and Michal G. (1999, Biochemical Pathways: An Atlas of Biochemistry and Molecular Biology, John Wiley and Sons; Fallon, A. et al. 1987, Applications of HPLC in Biochemistry in: Laboratory Techniques in Biochemistry and Molecular Biology, vol. 17).

We claim:

1. A method of producing a transgenic plant having an increased level of total fatty acids in a seed of the transgenic plant relative to a seed of a corresponding wild type plant comprising:
   i) transforming a plant cell with an expression vector comprising a lipid metabolism protein (LMP) nucleic acid and
   ii) generating from the plant cell the transgenic plant that expresses the LMP nucleic acid and that has an increased level of total fatty acids in the seed of the transgenic plant,
   wherein the LMP nucleic acid comprises a nucleic acid sequence selected from the group consisting of:
   a) the isolated nucleic acid sequence of SEQ ID NO: 27;
   b) an isolated nucleic acid encoding the polypeptide of SEQ ID NO: 28;
   c) an isolated nucleic acid that hybridizes under stringent conditions to the full-length nucleic acid sequence of SEQ ID NO: 27 or to a nucleic acid encoding the polypeptide of SEQ ID NO: 28, wherein the stringent conditions comprise hybridization in a 6× sodium chloride/sodium citrate (SSC) solution at about 45° C., followed by at least one wash in a 0.2×SSC, 0.1% sodium dodecyl sulfate (SDS) solution at 65° C.;
   d) an isolated nucleic acid having at least 95% sequence identity with the isolated full-length nucleic acid sequence of SEQ ID NO: 27 or with the nucleic acid encoding the polypeptide of SEQ ID NO: 28; and
   e) a nucleic acid encoding a polypeptide comprising an amino acid sequence having at least 95% identity to the amino acid sequence of SEQ ID NO: 28.

2. The method of claim 1, wherein the nucleic acid comprises the nucleic acid sequence of SEQ ID NO: 27.

3. The method of claim 1, wherein the nucleic acid comprises a nucleic acid having at least 95% sequence identity with the isolated full-length nucleic acid sequence of SEQ ID NO: 27.

4. The method of claim 1, wherein the nucleic acid comprises a nucleic acid that hybridizes under stringent conditions to the complement of the nucleic acid sequence of SEQ ID NO: 27 and wherein the stringent conditions comprise hybridization in a 6× sodium chloride/sodium citrate (SSC) solution at about 45° C., followed by at least one wash in a 0.2×SSC, 0.1% sodium dodecyl sulfate (SDS) solution at 65° C.

5. The method of claim 1, wherein the nucleic acid comprises a nucleic acid encoding the polypeptide of SEQ ID NO: 28 or a nucleic acid encoding a polypeptide comprising an amino acid sequence having at least 95% identity to the amino acid sequence of SEQ ID NO: 28.

6. The method of claim 1, wherein the nucleic acid comprises a nucleic acid having at least 95% sequence identity with the isolated full-length nucleic acid encoding the polypeptide of SEQ ID NO: 28.

7. The method of claim 1, wherein the nucleic acid comprises a nucleic acid that hybridizes under stringent conditions to the nucleic acid encoding the polypeptide of SEQ ID NO: 28 and wherein the stringent conditions comprise hybridization in a 6× sodium chloride/sodium citrate (SSC) solution at about 45° C., followed by at least one wash in a 0.2×SSC, 0.1% sodium dodecyl sulfate (SDS) solution at 65° C.

8. A transgenic plant or plant cell produced by the method of claim 1, wherein the LMP nucleic acid is expressed in the plant or plant cell, and wherein the seed of the plant has an increased level of the total fatty acid content as compared to the seed of a corresponding untransformed wild type plant.

9. The transgenic plant of claim 8, wherein the plant is a dicotyledonous plant.

10. The transgenic plant of claim 8, wherein the plant is a monocotyledonous plant.

11. The transgenic plant of claim 8, wherein the plant is an oil producing species.

12. The transgenic plant of claim 8, wherein the plant is selected from the group consisting of rapeseed, canola, linseed, soybean, sunflower, maize, oat, rye, barley, wheat, sugarbeet, tagetes, cotton, oil palm, coconut palm, flax, castor, and peanut.

13. A transgenic seed produced by the transgenic plant of claim 8, wherein the plant is true breeding for an increased level of the total fatty acid content in the seed as compared to a corresponding wild type plant.

14. A method of increasing the level of the total fatty acid content in a transgenic seed of a transgenic plant comprising,
   increasing the expression of an isolated lipid metabolism protein (LMP) nucleic acid in a transgenic plant,
   wherein the LMP nucleic acid comprises a nucleic acid sequence selected from the group consisting of:
   a) the isolated nucleic acid sequence of SEQ ID NO: 27;
   b) an isolated nucleic acid encoding the polypeptide of SEQ ID NO: 28;
   c) an isolated nucleic acid that hybridizes under stringent conditions to the full-length nucleic acid sequence of SEQ ID NO: 27 or to a nucleic acid encoding the polypeptide of SEQ ID NO: 28, wherein the stringent conditions comprise hybridization in a 6× sodium chloride/sodium citrate (SSC) solution at about 45° C., followed by at least one wash in a 0.2×SSC, 0.1% sodium dodecyl sulfate (SDS) solution at 65° C.;
   d) an isolated nucleic acid having at least 95% sequence identity with the isolated full-length nucleic acid sequence of SEQ ID NO: 27 or with the nucleic acid encoding the polypeptide of SEQ ID NO: 28; and
   e) an isolated nucleic acid encoding a polypeptide comprising an amino acid sequence having at least 95% identity to the amino acid sequence of SEQ ID NO: 28.

15. The method of claim 14, wherein the nucleic acid comprises the nucleic acid sequence of SEQ ID NO: 27.

16. The method of claim 14, wherein the nucleic acid comprises a nucleic acid having at least 95% sequence identity with the isolated full-length nucleic acid sequence of SEQ ID NO: 27.

17. The method of claim 14, wherein the nucleic acid comprises a nucleic acid that hybridizes under stringent conditions to the nucleic acid sequence of SEQ ID NO: 27, and wherein the stringent conditions comprise hybridization in a 6× sodium chloride/sodium citrate (SSC) solution at about 45° C., followed by at least one wash in a 0.2×SSC, 0.1% sodium dodecyl sulfate (SDS) solution at 65° C.

18. The method of claim 14, wherein the nucleic acid comprises the nucleic acid encoding the polypeptide of SEQ ID NO: 28 or a nucleic acid encoding a polypeptide comprising an amino acid sequence having at least 95% identity to the amino acid sequence of SEQ ID NO: 28.

19. The method of claim 14, wherein the nucleic acid comprises a nucleic acid having at least 95% sequence identity with the isolated full-length nucleic acid encoding the polypeptide of SEQ ID NO: 28.

20. The method of claim 14, wherein the nucleic acid comprises a nucleic acid that hybridizes under stringent conditions to a nucleic acid encoding the polypeptide of SEQ ID NO: 28, wherein the stringent conditions comprise hybridization in a 6× sodium chloride/sodium citrate (SSC) solution at about 45° C., followed by at least one wash in a 0.2×SSC, 0.1% sodium dodecyl sulfate (SDS) solution at 65° C.

21. A transgenic plant or part thereof comprising an isolated nucleic acid selected from the group consisting of
   a) the isolated nucleic acid sequence of SEQ ID NO: 27;
   b) an isolated nucleic acid encoding the polypeptide of SEQ ID NO: 28;
   c) an isolated nucleic acid having at least 95% sequence identity with the isolated full-length nucleic acid sequence of SEQ ID NO: 27 or with the nucleic acid encoding the polypeptide of SEQ ID NO: 28; and
   d) a nucleic acid encoding a polypeptide comprising an amino acid sequence having at least 95% sequence identity to the amino acid sequence of SEQ ID NO: 28,
   wherein the transgenic plant has an increased level of total fatty acids in a seed of the transgenic plant relative to a seed of a corresponding wild type plant.

22. A transgenic seed produced by the transgenic plant of claim 21, wherein the plant is true breeding for an increased level of the total fatty acid content in the seed as compared to a corresponding wild type plant.

23. The transgenic plant or part thereof of claim 21, wherein the part thereof comprises a transgenic seed.

* * * * *

```
                         SEQUENCE LISTING

<160> NUMBER OF SEQ ID NOS: 67

<210> SEQ ID NO 1
<211> LENGTH: 651
<212> TYPE: DNA
<213> ORGANISM: Arabidopsis thaliana

<400> SEQUENCE: 1
atgccaggga tcacactagg agacacggtg ccgaacctag aagtggagac gacacatgac     60
aagttcaaac ttcatgacta cttcgccaat tcttggaccg tcctcttctc tcatcccggg    120
gatttcacac ccgtgtgcac cacggagctt ggtgcgatgg ccaaatacgc tcatgagttc    180
gataagagag gcgtgaagct ccttggtctg tcttgtgacg atgtacagtc acacaaagac    240
tggatcaaaa atattgaagc ctttaatcac ggaagcaagg tgaattaccc gataatcgct    300
gacccgaaca aagagatcat tcctcagctt aacatgattg atccaattga aacggaccg     360 tctcgtgccc ttcatattgt tggtcctgac agtaagataa aattgagctt cttgtatccg    420
tcgaccacgg gacgtaacat ggacgaagta ttgagggctt tagactcgtt gttgatggcg    480
tccaagcaca ataacaagat cgccactccg gttaactgga agccagatca accggttgtg    540
atttcgcctg ctgtgtcgga cgaggaagcc aaaaagatgt tcccacaggg tttcaagacc    600
gccgatcttc cgtcaaagaa aggctatctg cgtcacacag aggtctcttg a             651

<210> SEQ ID NO 2
<211> LENGTH: 216
<212> TYPE: PRT
<213> ORGANISM: Arabidopsis thaliana

<400> SEQUENCE: 2

Met Pro Gly Ile Thr Leu Gly Asp Thr Val Pro Asn Leu Glu Val Glu
  1               5                  10                  15

Thr Thr His Asp Lys Phe Lys Leu His Asp Tyr Phe Ala Asn Ser Trp
             20                  25                  30

Thr Val Leu Phe Ser His Pro Gly Asp Phe Thr Pro Val Cys Thr Thr
         35                  40                  45

Glu Leu Gly Ala Met Ala Lys Tyr Ala His Glu Phe Asp Lys Arg Gly
     50                  55                  60

Val Lys Leu Leu Gly Leu Ser Cys Asp Asp Val Gln Ser His Lys Asp
 65                  70                  75                  80

Trp Ile Lys Asp Ile Glu Ala Phe Asn His Gly Ser Lys Val Asn Tyr
                 85                  90                  95

Pro Ile Ile Ala Asp Pro Asn Lys Glu Ile Ile Pro Gln Leu Asn Met
            100                 105                 110

Ile Asp Pro Ile Glu Asn Gly Pro Ser Arg Ala Leu His Ile Val Gly
        115                 120                 125

Pro Asp Ser Lys Ile Lys Leu Ser Phe Leu Tyr Pro Ser Thr Thr Gly
    130                 135                 140
```

Arg Asn Met Asp Glu Val Leu Arg Ala Leu Asp Ser Leu Leu Met Ala
145                 150                 155                 160

Ser Lys His Asn Asn Lys Ile Ala Thr Pro Val Asn Trp Lys Pro Asp
            165                 170                 175

Gln Pro Val Ile Ser Pro Ala Val Ser Asp Glu Ala Lys Lys
        180                 185                 190

Met Phe Pro Gln Gly Phe Lys Thr Ala Asp Leu Pro Ser Lys Lys Gly
        195                 200                 205

Tyr Leu Arg His Thr Glu Val Ser
        210                 215

<210> SEQ ID NO 3
<211> LENGTH: 930
<212> TYPE: DNA
<213> ORGANISM: Arabidopsis thaliana

<400> SEQUENCE: 3

```
agaggacgag acaagggga cattttgtg tttgaatata tcaacaaaat tagatttgat      60
atgtgctaag atatgatgta ttagttgaca tgacgatttc ttttactact agccaaatca    120
tttaataatc agtcacaaag aggaagagaa atgtgttcat tagagaaacg tgatcgtctt    180
ttcatactaa aactcaccgg cgacggcgaa caccgtctaa acccaacctt attcgactct    240
ctccgctcca ccatcaacca aatccgatca gatccatcat tttcacaatc agtactcatc    300
acaacatcag atggtaaatt cttctccaac ggctacgatc tcgctttagc cgagtcaaat    360
ccttctctct ctgttgtaat ggacgcaaaa cttagatcct tagtcgccga tctaatctct    420
cttcctatgc caacaatcgc cgccgtcaca ggtcacgctt ccgccgcggg atgtatttta    480
gcgatgagtc atgattatgt attgatgcgt cgtgatagag gttttttgta tatgagtgaa    540
ttggatattg agttgatagt tccggcgtgg ttcatggctg ttattagggg taagattggt    600
tctccggcgg ccagaaggga tgtgatgttg acggcggcga aagtgacggc ggatgtgggt    660
gttaagatgg ggattgttga ttcggcgtat ggtagtgcgg cggagacggt tgaagccgcc    720
attaagttag gtgaggagat tgttcagaga ggtggtgatg acacgtgta tggtaagatg    780
agagagagtc tttttaagaga ggttcttatc catacgattg gtgaatatga gagtggttca    840
agtgtggtgc gtagcactgg atctaaactt tagaacatgt tgtacttct tgggctactt     900
gtcagttctt ttcagcaatt gttctttata                                     930
```

<210> SEQ ID NO 4
<211> LENGTH: 240
<212> TYPE: PRT
<213> ORGANISM: Arabidopsis thaliana

<400> SEQUENCE: 4

Met Cys Ser Leu Glu Lys Arg Asp Arg Leu Phe Ile Leu Lys Leu Thr
1               5                   10                  15

Gly Asp Gly Glu His Arg Leu Asn Pro Thr Leu Leu Asp Ser Leu Arg
            20                  25                  30

Ser Thr Ile Asn Gln Ile Arg Ser Asp Pro Ser Phe Ser Gln Ser Val
        35                  40                  45

Leu Ile Thr Thr Ser Asp Gly Lys Phe Phe Ser Asn Gly Tyr Asp Leu
    50                  55                  60

Ala Leu Ala Glu Ser Asn Pro Ser Leu Ser Val Val Met Asp Ala Lys
65                  70                  75                  80

Leu Arg Ser Leu Val Ala Asp Leu Ile Ser Leu Pro Met Pro Thr Ile

|   |   |   |   | 85 |   |   |   |   | 90 |   |   |   |   | 95 |   |
|---|---|---|---|---|---|---|---|---|---|---|---|---|---|---|---|

Ala Ala Val Thr Gly His Ala Ser Ala Gly Cys Ile Leu Ala Met
            100                 105                 110

Ser His Asp Tyr Val Leu Met Arg Arg Asp Arg Gly Phe Leu Tyr Met
            115                 120                 125

Ser Glu Leu Asp Ile Glu Leu Ile Val Pro Ala Trp Phe Met Ala Val
            130                 135                 140

Ile Arg Gly Lys Ile Gly Ser Pro Ala Ala Arg Arg Asp Val Met Leu
145                 150                 155                 160

Thr Ala Ala Lys Val Thr Ala Asp Val Gly Val Lys Met Gly Ile Val
            165                 170                 175

Asp Ser Ala Tyr Gly Ser Ala Ala Glu Thr Val Glu Ala Ala Ile Lys
            180                 185                 190

Leu Gly Glu Glu Ile Val Gln Arg Gly Gly Asp Gly His Val Tyr Gly
            195                 200                 205

Lys Met Arg Glu Ser Leu Leu Arg Glu Val Leu Ile His Thr Ile Gly
            210                 215                 220

Glu Tyr Glu Ser Gly Ser Ser Val Val Arg Ser Thr Gly Ser Lys Leu
225                 230                 235                 240

<210> SEQ ID NO 5
<211> LENGTH: 1998
<212> TYPE: DNA
<213> ORGANISM: Arabidopsis thaliana

<400> SEQUENCE: 5

| | | |
|---|---|---|
| atgtctccac ttctccggtt tagaaaacta tcgtccttct ctgaagatac cattaaccct | 60 |
| aaacccaaac aatcggcaac cgtcgagaaa ccaaaacggc gccgttccgg gagatgtagc | 120 |
| tgcgttgact catgttgctg gttgattggt tatctctgta cggcgtggtg gcttctcctc | 180 |
| tttctttacc actctgttcc ggtcccggcg atgcttcaag ctccggagtc tccgggaact | 240 |
| cggttgagtc gagacggtgt caaggcgttt catccggtga ttcttgttcc ggggattgta | 300 |
| accggcgggc tcgagctttg gaaggtcggc ccttgcgctg aaggactctt cgtaaacgt | 360 |
| cttttggggtg ctagcttctc cgagattctt agaaggccat tgtgctggtt ggagcactta | 420 |
| tctctagaca gtgagaccgg tctcgatcca tcgggaatcc gtgtccgagc agtcccagga | 480 |
| ctagtggctg cagactattt cgcaccatgc tactttgctt gggcagttct catagagaat | 540 |
| ttggcaaaaa ttggatatga aggcaagaac cttcacatgg cctcttatga ttggagactc | 600 |
| tcttttccata caccgaggt acgtgaccaa tcgttaagta gactgaagag caaaatcgag | 660 |
| ctaatgtatg ccaccaatgg gtttaagaaa gttgtggtgg ttccgcattc aatgggggct | 720 |
| atctatttcc ttcacttcct taaatgggta gaaacacctc ttcctgatgg aggcggtggg | 780 |
| ggtggtccag ttggtgtgc aaacacatc aaatccgtcg tcaacattgg acccgccttt | 840 |
| ttaggtgttc ctaaagccgt cagtaattta cttcctgctg aaggcaaaga catcgcttac | 900 |
| gccagatctt tggctccagg tctcttggac tcggaacttc tcaagctgca aacactcgaa | 960 |
| caccttatgc ggatgtcaca tagctgggat tcaatagtat ctttattacc aaagggcggt | 1020 |
| gaggcaattt ggggcgatct agactcgcac gctgaagaag gactcaattg tatttactcc | 1080 |
| aagagaaaat catcgcagct atcgctaagt aatctcccata acaaaacta cagccttaaa | 1140 |
| ccggtgtcac gggtgaaaga acccgcaaag tacggaagaa tcgtatcttt cgggaaacga | 1200 |
| gcatcagaac tgccttcctc acaactctct acgctaaacg tcaaggaact gtcaagagta | 1260 |
| gatggcaatt caaatgacag tacatcatgt ggagagtttt ggtcagagta caatgaaatg | 1320 |

```
agccgagaaa gcatagtaaa agtagcagaa aacacagctt atacagccac cactgttctt    1380
gatcttcttc gatttatagc ccctaagatg atgagacgag ccgaagctca tttctctcac    1440
ggcattgctg atgatcttga tgaccctaag tatggacatt ataagtactg gtctaatcca    1500
ctcgagacca aattaccgga ggcaccagag atggaaatgt actgtcttta cggagtaggg    1560
attccgaccg agagatctta catatacaag ctcgcaacct cttccggtaa atgcaagagc    1620
agcattccct tccggataga tggatctctg gatggagatg acgtttgtct aagggagga    1680 acacggtttg cggacggaga cgagagtgta ccggtgataa gtgcgggtt tatgtgcgca    1740 aagggatgga gaggaaaaac acggtttaac ccgtcaggga tggatacatt cttgcgggaa    1800
tacaaacata agccgccggg aagtctacta gaaagtcgag gaacggaaag cggagctcat    1860
gtagacataa tgggtaatgt tggactcatt gaagatgttt tgaggatagc tgccggagct    1920
tcaggccagg agattggtgg cgatagaatt tactcggatg tgatgaggat gtcggagaga    1980
attagcatca agttgtga                                                  1998

<210> SEQ ID NO 6
<211> LENGTH: 665
<212> TYPE: PRT
<213> ORGANISM: Arabidopsis thaliana

<400> SEQUENCE: 6

Met Ser Pro Leu Leu Arg Phe Arg Lys Leu Ser Ser Phe Ser Glu Asp
 1               5                  10                  15

Thr Ile Asn Pro Lys Pro Lys Gln Ser Ala Thr Val Glu Lys Pro Lys
             20                  25                  30

Arg Arg Arg Ser Gly Arg Cys Ser Cys Val Asp Ser Cys Cys Trp Leu
         35                  40                  45

Ile Gly Tyr Leu Cys Thr Ala Trp Trp Leu Leu Phe Leu Tyr His
     50                  55                  60

Ser Val Pro Val Pro Ala Met Leu Gln Ala Pro Glu Ser Pro Gly Thr
 65                  70                  75                  80

Arg Leu Ser Arg Asp Gly Val Lys Ala Phe His Pro Val Ile Leu Val
                 85                  90                  95

Pro Gly Ile Val Thr Gly Gly Leu Glu Leu Trp Glu Gly Arg Pro Cys
            100                 105                 110

Ala Glu Gly Leu Phe Arg Lys Arg Leu Trp Gly Ala Ser Phe Ser Glu
        115                 120                 125

Ile Leu Arg Arg Pro Leu Cys Trp Leu Glu His Leu Ser Leu Asp Ser
    130                 135                 140

Glu Thr Gly Leu Asp Pro Ser Gly Ile Arg Val Arg Ala Val Pro Gly
145                 150                 155                 160

Leu Val Ala Ala Asp Tyr Phe Ala Pro Cys Tyr Phe Ala Trp Ala Val
                165                 170                 175

Leu Ile Glu Asn Leu Ala Lys Ile Gly Tyr Glu Gly Lys Asn Leu His
            180                 185                 190

Met Ala Ser Tyr Asp Trp Arg Leu Ser Phe His Asn Thr Glu Val Arg
        195                 200                 205

Asp Gln Ser Leu Ser Arg Leu Lys Ser Lys Ile Glu Leu Met Tyr Ala
    210                 215                 220

Thr Asn Gly Phe Lys Lys Val Val Val Pro His Ser Met Gly Ala
225                 230                 235                 240

Ile Tyr Phe Leu His Phe Leu Lys Trp Val Glu Thr Pro Leu Pro Asp
                245                 250                 255
```

```
Gly Gly Gly Gly Gly Pro Gly Trp Cys Ala Lys His Ile Lys Ser
            260                 265                 270

Val Val Asn Ile Gly Pro Ala Phe Leu Gly Val Pro Lys Ala Val Ser
            275                 280                 285

Asn Leu Leu Ser Ala Glu Gly Lys Asp Ile Ala Tyr Ala Arg Ser Leu
            290                 295                 300

Ala Pro Gly Leu Leu Asp Ser Glu Leu Lys Leu Gln Thr Leu Glu
305                 310                 315                 320

His Leu Met Arg Met Ser His Ser Trp Asp Ser Ile Val Ser Leu Leu
                325                 330                 335

Pro Lys Gly Gly Glu Ala Ile Trp Gly Asp Leu Asp Ser His Ala Glu
            340                 345                 350

Glu Gly Leu Asn Cys Ile Tyr Ser Lys Arg Lys Ser Ser Gln Leu Ser
            355                 360                 365

Leu Ser Asn Leu His Lys Gln Asn Tyr Ser Leu Lys Pro Val Ser Arg
            370                 375                 380

Val Lys Glu Pro Ala Lys Tyr Gly Arg Ile Val Ser Phe Gly Lys Arg
385                 390                 395                 400

Ala Ser Glu Leu Pro Ser Ser Gln Leu Ser Thr Leu Asn Val Lys Glu
                405                 410                 415

Leu Ser Arg Val Asp Gly Asn Ser Asn Asp Ser Thr Ser Cys Gly Glu
            420                 425                 430

Phe Trp Ser Glu Tyr Asn Glu Met Ser Arg Glu Ser Ile Val Lys Val
            435                 440                 445

Ala Glu Asn Thr Ala Tyr Thr Ala Thr Thr Val Leu Asp Leu Leu Arg
450                 455                 460

Phe Ile Ala Pro Lys Met Met Arg Arg Ala Glu Ala His Phe Ser His
465                 470                 475                 480

Gly Ile Ala Asp Asp Leu Asp Asp Pro Lys Tyr Gly His Tyr Lys Tyr
            485                 490                 495

Trp Ser Asn Pro Leu Glu Thr Lys Leu Pro Glu Ala Pro Glu Met Glu
            500                 505                 510

Met Tyr Cys Leu Tyr Gly Val Gly Ile Pro Thr Glu Arg Ser Tyr Ile
            515                 520                 525

Tyr Lys Leu Ala Thr Ser Ser Gly Lys Cys Lys Ser Ser Ile Pro Phe
            530                 535                 540

Arg Ile Asp Gly Ser Leu Asp Gly Asp Val Cys Leu Lys Gly Gly
545                 550                 555                 560

Thr Arg Phe Ala Asp Gly Asp Glu Ser Val Pro Val Ile Ser Ala Gly
                565                 570                 575

Phe Met Cys Ala Lys Gly Trp Arg Gly Lys Thr Arg Phe Asn Pro Ser
            580                 585                 590

Gly Met Asp Thr Phe Leu Arg Glu Tyr Lys His Lys Pro Pro Gly Ser
            595                 600                 605

Leu Leu Glu Ser Arg Gly Thr Glu Ser Gly Ala His Val Asp Ile Met
            610                 615                 620

Gly Asn Val Gly Leu Ile Glu Asp Val Leu Arg Ile Ala Ala Gly Ala
625                 630                 635                 640

Ser Gly Gln Glu Ile Gly Asp Arg Ile Tyr Ser Asp Val Met Arg
            645                 650                 655

Met Ser Glu Arg Ile Ser Ile Lys Leu
            660                 665
```

<210> SEQ ID NO 7
<211> LENGTH: 1203
<212> TYPE: DNA
<213> ORGANISM: Arabidopsis thaliana

<400> SEQUENCE: 7

```
atgcgcttcc gatcattctt cttctcctcc tctatcttct cccttcaca ttctcgctct      60
ccttctcttt cttcctctcg tttctcctct ctctccgccg ctatgtctcc tgctctcgag     120
aaatcccgac aaggcaatgg tggatgtaat gatgattcga atctaaggt cacggtcgtt     180
ggtagtggca attggggaag tgttgctgct aagctcattg cttctaatgc cctcaagctt     240
ccttctttcc atgatgaagt gaggatgtgg gtgtttgagg aggttctacc aaatggtgag     300
aagctcaatg atgttatcaa caagaccaat gaaaatgtca agtacctccc tgggattaag     360
ctaggaagaa atgttgttgc ggatcctgac cttgaaaatg cagtgaagga cgcgaacatg     420
ttggttttg ttacaccgca tcagtttatg gatggtatat gcaagaagtt agatggaaag      480
atcacaggag atgttgaggc tatatctctt gttaaaggaa tggaagtgaa gaggaaggt      540
ccttgtatga tctcaagtct catttccaag caacttggta tcaattgttg tgttcttatg     600
ggcgcaaaca ttgcaaacga gatagctgtg agaagttta gtgaagcaac ggttggatat      660
agagggagta gagaaatagc ggacacatgg gttcagttgt tagtactcc gtattttatg      720
gtcacaccgg tccatgatgt ggaaggagta gagttatgtg ggactttgaa gatgtagtt      780
gctattgcag cgggttttcgt ggacggtttg gaaatgggta ataacacaaa ggctgcaatc    840
atgaggatt gtctaagaga gatgaaagca ctctcaaagc ttttgttcc atctgttaaa      900
gatagtactt tcttcgagag ctgcggtgta gcagatgtca ttacaacttg cttaggagga    960
agaaaccgga gagttgcgga agcatttgca aaaagcagag gaaaaaggtc ttttgatgag   1020
cttgaagcag agatgctaca agggcaaaag ctacaggggg tatcgacggc aagagaggtc   1080
tacgaggtgt tgaaacattg tggatggttg agatgtttc cgctcttttc aacggttcac   1140
caaatctgca ctggtcgtct tcaacctgaa gccatcgtcc aataccgcga gaacaaacta   1200
taa                                                                 1203
```

<210> SEQ ID NO 8
<211> LENGTH: 400
<212> TYPE: PRT
<213> ORGANISM: Arabidopsis thaliana

<400> SEQUENCE: 8

```
Met Arg Phe Arg Ser Phe Phe Ser Ser Ile Phe Ser Leu Ser
  1               5                  10                  15

His Ser Arg Ser Pro Ser Leu Ser Ser Ser Arg Phe Ser Ser Leu Ser
              20                  25                  30

Ala Ala Met Ser Pro Ala Leu Glu Lys Ser Arg Gln Gly Asn Gly Gly
          35                  40                  45

Cys Asn Asp Asp Ser Lys Ser Lys Val Thr Val Gly Ser Gly Asn
      50                  55                  60

Trp Gly Ser Val Ala Ala Lys Leu Ile Ala Ser Asn Ala Leu Lys Leu
 65                  70                  75                  80

Pro Ser Phe His Asp Glu Val Arg Met Trp Val Phe Glu Glu Val Leu
                  85                  90                  95

Pro Asn Gly Glu Lys Leu Asn Asp Val Ile Asn Lys Thr Asn Glu Asn
             100                 105                 110

Val Lys Tyr Leu Pro Gly Ile Lys Leu Gly Arg Asn Val Val Ala Asp
         115                 120                 125
```

Pro Asp Leu Glu Asn Ala Val Lys Asp Ala Asn Met Leu Val Phe Val
    130                 135                 140

Thr Pro His Gln Phe Met Asp Gly Ile Cys Lys Lys Leu Asp Gly Lys
145                 150                 155                 160

Ile Thr Gly Asp Val Glu Ala Ile Ser Leu Val Lys Gly Met Glu Val
                165                 170                 175

Lys Lys Glu Gly Pro Cys Met Ile Ser Ser Leu Ile Ser Lys Gln Leu
            180                 185                 190

Gly Ile Asn Cys Cys Val Leu Met Gly Ala Asn Ile Ala Asn Glu Ile
        195                 200                 205

Ala Val Glu Lys Phe Ser Glu Ala Thr Val Gly Tyr Arg Gly Ser Arg
    210                 215                 220

Glu Ile Ala Asp Thr Trp Val Gln Leu Phe Ser Thr Pro Tyr Phe Met
225                 230                 235                 240

Val Thr Pro Val His Asp Val Glu Gly Val Glu Leu Cys Gly Thr Leu
                245                 250                 255

Lys Asn Val Val Ala Ile Ala Ala Gly Phe Val Asp Gly Leu Glu Met
            260                 265                 270

Gly Asn Asn Thr Lys Ala Ala Ile Met Arg Ile Gly Leu Arg Glu Met
        275                 280                 285

Lys Ala Leu Ser Lys Leu Leu Phe Pro Ser Val Lys Asp Ser Thr Phe
    290                 295                 300

Phe Glu Ser Cys Gly Val Ala Asp Val Ile Thr Thr Cys Leu Gly Gly
305                 310                 315                 320

Arg Asn Arg Arg Val Ala Glu Ala Phe Ala Lys Ser Arg Gly Lys Arg
                325                 330                 335

Ser Phe Asp Glu Leu Glu Ala Glu Met Leu Gln Gly Gln Lys Leu Gln
            340                 345                 350

Gly Val Ser Thr Ala Arg Glu Val Tyr Glu Val Leu Lys His Cys Gly
        355                 360                 365

Trp Leu Glu Met Phe Pro Leu Phe Ser Thr Val His Gln Ile Cys Thr
    370                 375                 380

Gly Arg Leu Gln Pro Glu Ala Ile Val Gln Tyr Arg Glu Asn Lys Leu
385                 390                 395                 400

<210> SEQ ID NO 9
<211> LENGTH: 1176
<212> TYPE: DNA
<213> ORGANISM: Arabidopsis thaliana

<400> SEQUENCE: 9
atgttgccca gattagctcg agtcgtcact caaacctcaa agcttcgatc tttgaccact     60
aatggatcga tgaaaaatct ctccttttc tcccgatatg ggtacgcgac tgttgcgccg    120
gcggcagctg atcctccgtc gcagaaggat ttccccagta atctccgct gttaatgcgt    180 agttgttgtg aatgtttagg tctcactata gtattcgaac ctaagctcaa tttgattctc    240
tctgttccta gtttcatcga atgcgggact aaaataaact tggataagat gttttggtca    300
aagccatgtt cattggctct gcctaaagac tctcctctca gaattgatga ccagactat    360 gtagggattc gtcgtttcat actaaagatg atgatgttct atagcaaaca gagcatgtct    420
atccgtgggg ctaacgtgat ctacaagcgg atcattgcac aagttgataa acctgcaata    480
tatgatgtat tcaacttgga gaaacattc aaaataacgt attcgctgct tgtccttcat    540
atgtggcttg tttacgccg cttgaaggaa gatggacagg aaggtgttga ccttggtcaa    600

```
tacgtctatg agatctacaa tcatgatgtt gaactcaggg tatctaaagc cggggttaac    660
ttgctgctag ccaagtggat gaaggagttg gagagaatat tttatggaaa tgttgttgcc    720
tatgatgctg cgctacttcc ggaagctaaa ccaaatgacc tacaaatcaa attatggagg    780
aacgtatttt ctgatgatgg aacaacaaca cctgataaca cagatttaaa aacagcacag    840
gcaatggcaa gatatgtccg gagagaactt ggttctcttt ctttaacagg tacctatgac    900
gctatagttg gaatgcctca ttatgttact cgcatttgca tttcgaatag acatgccttt    960
tcttatatgg ttcttttttg tcatacacag ataaagagtc catattctcc ggcaatttct   1020
ccttcacccc tttggagaac aagcccctgt gatttgaatg aaattagaag aagctgtggt   1080
gctttgcgaa tcaatctttc atttgtttct ctgtttcatt tgatttactt atatcaaacc   1140
aaagaaacct acacaaggga atgtgctagc tgttag                             1176
```

```
<210> SEQ ID NO 10
<211> LENGTH: 391
<212> TYPE: PRT
<213> ORGANISM: Arabidopsis thaliana

<400> SEQUENCE: 10

Met Leu Pro Arg Leu Ala Arg Val Val Thr Gln Thr Ser Lys Leu Arg
 1               5                  10                  15

Ser Leu Thr Thr Asn Gly Ser Met Lys Asn Leu Ser Phe Phe Ser Arg
                20                  25                  30

Tyr Gly Tyr Ala Thr Val Ala Pro Ala Ala Asp Pro Pro Ser Gln
        35                  40                  45

Lys Asp Phe Pro Ser Lys Ser Pro Leu Leu Met Arg Ser Cys Cys Glu
    50                  55                  60

Cys Leu Gly Leu Thr Ile Val Phe Glu Pro Lys Leu Asn Leu Ile Leu
 65                  70                  75                  80

Ser Val Ser Ser Phe Ile Glu Cys Gly Thr Lys Ile Asn Leu Asp Lys
                85                  90                  95

Met Phe Trp Ser Lys Pro Cys Ser Leu Ala Leu Pro Lys Asp Ser Pro
            100                 105                 110

Leu Arg Ile Asp Glu Pro Asp Tyr Val Gly Ile Arg Arg Phe Ile Leu
        115                 120                 125

Lys Met Met Met Phe Tyr Ser Lys Gln Ser Met Ser Ile Arg Gly Ala
130                 135                 140

Asn Val Ile Tyr Lys Arg Ile Ile Ala Gln Val Asp Lys Pro Ala Ile
145                 150                 155                 160

Tyr Asp Val Phe Asn Leu Glu Lys Thr Phe Lys Ile Thr Tyr Ser Leu
                165                 170                 175

Leu Val Leu His Met Trp Leu Val Leu Arg Arg Leu Lys Glu Asp Gly
            180                 185                 190

Gln Glu Gly Val Asp Leu Gly Gln Tyr Val Tyr Glu Ile Tyr Asn His
        195                 200                 205

Asp Val Glu Leu Arg Val Ser Lys Ala Gly Val Asn Leu Leu Leu Ala
    210                 215                 220

Lys Trp Met Lys Glu Leu Glu Arg Ile Phe Tyr Gly Asn Val Val Ala
225                 230                 235                 240

Tyr Asp Ala Ala Leu Leu Pro Glu Ala Lys Pro Asn Asp Leu Gln Ile
                245                 250                 255

Lys Leu Trp Arg Asn Val Phe Ser Asp Asp Gly Thr Thr Thr Pro Asp
            260                 265                 270

Asn Thr Asp Leu Lys Thr Ala Gln Ala Met Ala Arg Tyr Val Arg Arg
```

```
                    275                 280                 285
Glu Leu Gly Ser Leu Ser Leu Thr Gly Thr Tyr Asp Ala Ile Val Gly
        290                 295                 300

Met Pro His Tyr Val Thr Arg Ile Cys Ile Ser Asn Arg His Ala Phe
305                 310                 315                 320

Ser Tyr Met Val Leu Phe Cys His Thr Gln Ile Lys Ser Pro Tyr Ser
                325                 330                 335

Pro Ala Ile Ser Pro Ser Pro Leu Trp Arg Thr Ser Pro Cys Asp Leu
        340                 345                 350

Asn Glu Ile Arg Arg Ser Cys Gly Ala Leu Arg Ile Asn Leu Ser Phe
                355                 360                 365

Val Ser Leu Phe His Leu Ile Tyr Leu Tyr Gln Thr Lys Glu Thr Tyr
        370                 375                 380

Thr Arg Glu Cys Ala Ser Cys
385                 390

<210> SEQ ID NO 11
<211> LENGTH: 843
<212> TYPE: DNA
<213> ORGANISM: Arabidopsis thaliana

<400> SEQUENCE: 11
atgttgccca gattagctcg agtcgtcact caaacctcaa agcttcgatc tttgaccact      60
aatggatcga tgaaaaatct ctccttttc tcccgatatg gtacgcgac tgttgcgccg      120 gcggcagctg atcctccgtc gcagaaggat ttccccagta atctccgat aaacttggat      180 aagatgtttt ggtcaaagcc atgttcattg ctctgcctaa agactctcc tctcagaatt      240 gatgaaccag actatgtagg gattcgtcgt tcatactaa agatgatgat gttctatagc      300
aaacagagca tgtctatccg tggggctaac gtgatctaca gcggatcat gcacaagtt      360 gataaacctg caatatatga tgtattcaac ttggagaaaa cattcaaaat aacgtattcg      420
ttgcttgtcc ttcatatgtg gcttgtttta cgccgcttga aggaagatgg acaggaaggt      480
gttgaccttg tcaatacgt ctatgagatc tacaatcatg atgttgaact cagggtatct      540
aaagccgggg ttaacttgct gctagccaag tggatgaagg agttggagag aatatttat      600 ggaaatgttg ttgcctatga tgctgcgcta cttccggaag ctaaaccaaa tgacctacaa      660
atcaaattat ggaggaacgt attttctgat gatggaacaa caacacctga taacacagat      720
ttaaaaacag cacaggcaat ggcaagatat gtccggagag aacttggttc tctttcttta      780
acagataaag agtccatatt ctccggcaat ttctccttca cccctttgga gaacaagccc      840
ctg                                                                   843

<210> SEQ ID NO 12
<211> LENGTH: 281
<212> TYPE: PRT
<213> ORGANISM: Arabidopsis thaliana

<400> SEQUENCE: 12

Met Leu Pro Arg Leu Ala Arg Val Val Thr Gln Thr Ser Lys Leu Arg
1               5                   10                  15

Ser Leu Thr Thr Asn Gly Ser Met Lys Asn Leu Ser Phe Phe Ser Arg
            20                  25                  30

Tyr Gly Tyr Ala Thr Val Ala Pro Ala Ala Asp Pro Pro Ser Gln
        35                  40                  45

Lys Asp Phe Pro Ser Lys Ser Pro Ile Asn Leu Asp Lys Met Phe Trp
    50                  55                  60
```

```
Ser Lys Pro Cys Ser Leu Ala Leu Pro Lys Asp Ser Pro Leu Arg Ile
 65                  70                  75                  80

Asp Glu Pro Asp Tyr Val Gly Ile Arg Arg Phe Ile Leu Lys Met Met
                 85                  90                  95

Met Phe Tyr Ser Lys Gln Ser Met Ser Ile Arg Gly Ala Asn Val Ile
            100                 105                 110

Tyr Lys Arg Ile Ile Ala Gln Val Asp Lys Pro Ala Ile Tyr Asp Val
        115                 120                 125

Phe Asn Leu Glu Lys Thr Phe Lys Ile Thr Tyr Ser Leu Leu Val Leu
    130                 135                 140

His Met Trp Leu Val Leu Arg Arg Leu Lys Glu Asp Gly Gln Glu Gly
145                 150                 155                 160

Val Asp Leu Gly Gln Tyr Val Tyr Glu Ile Tyr Asn His Asp Val Glu
                165                 170                 175

Leu Arg Val Ser Lys Ala Gly Val Asn Leu Leu Ala Lys Trp Met
                180                 185                 190

Lys Glu Leu Glu Arg Ile Phe Tyr Gly Asn Val Val Ala Tyr Asp Ala
        195                 200                 205

Ala Leu Leu Pro Glu Ala Lys Pro Asn Asp Leu Gln Ile Lys Leu Trp
    210                 215                 220

Arg Asn Val Phe Ser Asp Gly Thr Thr Thr Pro Asp Asn Thr Asp
225                 230                 235                 240

Leu Lys Thr Ala Gln Ala Met Ala Arg Tyr Val Arg Arg Glu Leu Gly
                245                 250                 255

Ser Leu Ser Leu Thr Asp Lys Glu Ser Ile Phe Ser Gly Asn Phe Ser
            260                 265                 270

Phe Thr Pro Leu Glu Asn Lys Pro Leu
        275                 280

<210> SEQ ID NO 13
<211> LENGTH: 2016
<212> TYPE: DNA
<213> ORGANISM: Arabidopsis thaliana

<400> SEQUENCE: 13
atgtcggccg gtaacggaaa tgctactaac ggtgacggag ggtttagttt ccctaaagga     60
ccggtgatgc cgaagataac gaccggagca gcaaagagag gtagcggagt ctgccacgac    120
gatagtggtc cgacggtgaa tgccacaacc atcgatgagc ttcattcgtt acagaagaaa    180
cgttctgctc ctaccacacc gatcaaccaa aacgccgccg ctgcttttgc cgccgtctcc    240
gaggaggagc gtcagaagat tcagcttcaa tctatcagtg catcgttagc atcgttaacg    300
agagagtcag gaccaaaggt ggtgagagga gatccggcgg agaagaagac cgatggttca    360
actactccgg cgtacgctca cggccaacat cattctatct tttctccggc tactggtgct    420
gtcagtgata gctccttgaa gtttactcac gtcctctaca atctttcgcc tgcagagctt    480
tatgagcaag ctattaagta tgagaaaggt tcgtttatca cttctaatgg agctttggcg    540
acgctttctg gtgctaagac tggtcgtgct cccagagata gcgtgttgt tagagatgct    600 actactgagg atgagctttg gtggggaaag ggttcgccga atatcgaaat ggatgaacat    660
actttcatgg tgaacagaga aagagctgtt gattacttga attccttgga aaaggtcttt    720
gtcaatgacc aatacttaaa ctgggatcca gagaacagaa tcaaagtcag gattgtctca    780
gctagagctt accattcatt gtttatgcac aacatgtgta tccgaccaac tcaggaggag    840
cttgagagct ttggtactcc ggattttact atatacaatg ctgggcagtt tccatgtaat    900
```

```
cgttacactc attacatgac ttcgtccact agcgtagacc ttaatctggc taggagggaa    960
atggttatac ttggtactca gtatgctggg gaaatgaaga agggtctttt cagtgtgatg   1020
cattacctta tgcctaagcg tcgtattctc tcccttcatt ctggatgcaa atgggaaaa    1080 gatggagatg ttgctctctt ctttggactt tcaggtaccg ggaagacaac gctgtctact   1140
gatcacaaca ggtatcttat ggagatgat gagcattgtt ggactgagac tggtgtttcg    1200
aacattgagg gtgggtgcta tgctaagtgt gttgatcttt cgagggagaa ggagcctgat   1260
atctggaacg ctatcaagtt tggaacagtt ttggaaaatg ttgtgtttga tgagcacacc   1320
agagaagtgg attactctga taaatctgtt acagagaaca cacgtgctgc ctacccaatt   1380
gagttcattc caaatgcgaa ataccttgt gttggtccac acccgacaaa tgtgatactt     1440
ctggcttgtg atgcctttgg tgttctccca cctgtgagca agctgaatct ggcacaaacc   1500
atgtaccact tcatcagtgg ttacactgct ctggttgctg gcacagagga tggtatcaag   1560
gagccaacag caacattctc agcttgcttt ggtgcagctt tcataatgtt gcatcccaca   1620
aagtatgcag ctatgttagc tgagaagatg aagtcacaag gtgctactgg ttggctcgtc   1680
aacactggtt ggtctggtgg cagttatggt gttgaaaaca gaatcaagct ggcatacact   1740
agaaagatca tcgatgcaat ccattcgggc agtctcttga aggcaaacta caagaaaacc   1800
gaaatctttg gatttgaaat cccaactgag atcgaaggga taccttcaga gatcttggac   1860
cccgtcaact cctggtctga taagaaggca cacaaagata ctctggtgaa actgggaggt   1920
ctgttcaaga agaacttcga ggttttgct aaccataaga ttggtgtgga tggtaagctt    1980
acggaggaga ttctcgctgc tggtcctatc ttttag                             2016

<210> SEQ ID NO 14
<211> LENGTH: 671
<212> TYPE: PRT
<213> ORGANISM: Arabidopsis thaliana

<400> SEQUENCE: 14

Met Ser Ala Gly Asn Gly Asn Ala Thr Asn Gly Asp Gly Gly Phe Ser
  1               5                  10                  15

Phe Pro Lys Gly Pro Val Met Pro Lys Ile Thr Thr Gly Ala Ala Lys
                 20                  25                  30

Arg Gly Ser Gly Val Cys His Asp Asp Ser Gly Pro Thr Val Asn Ala
             35                  40                  45

Thr Thr Ile Asp Glu Leu His Ser Leu Gln Lys Lys Arg Ser Ala Pro
         50                  55                  60

Thr Thr Pro Ile Asn Gln Asn Ala Ala Ala Phe Ala Ala Val Ser
 65                  70                  75                  80

Glu Glu Glu Arg Gln Lys Ile Gln Leu Gln Ser Ile Ser Ala Ser Leu
                 85                  90                  95

Ala Ser Leu Thr Arg Glu Ser Gly Pro Lys Val Val Arg Gly Asp Pro
            100                 105                 110

Ala Glu Lys Lys Thr Asp Gly Ser Thr Thr Pro Ala Tyr Ala His Gly
        115                 120                 125

Gln His His Ser Ile Phe Ser Pro Ala Thr Gly Ala Val Ser Asp Ser
    130                 135                 140

Ser Leu Lys Phe Thr His Val Leu Tyr Asn Leu Ser Pro Ala Glu Leu
145                 150                 155                 160

Tyr Glu Gln Ala Ile Lys Tyr Glu Lys Gly Ser Phe Ile Thr Ser Asn
                165                 170                 175
```

```
Gly Ala Leu Ala Thr Leu Ser Gly Ala Lys Thr Gly Arg Ala Pro Arg
            180                 185                 190

Asp Lys Arg Val Val Arg Asp Ala Thr Thr Glu Asp Glu Leu Trp Trp
            195                 200                 205

Gly Lys Gly Ser Pro Asn Ile Glu Met Asp Glu His Thr Phe Met Val
            210                 215                 220

Asn Arg Glu Arg Ala Val Asp Tyr Leu Asn Ser Leu Glu Lys Val Phe
225                 230                 235                 240

Val Asn Asp Gln Tyr Leu Asn Trp Asp Pro Glu Asn Arg Ile Lys Val
            245                 250                 255

Arg Ile Val Ser Ala Arg Ala Tyr His Ser Leu Phe Met His Asn Met
            260                 265                 270

Cys Ile Arg Pro Thr Gln Glu Glu Leu Glu Ser Phe Gly Thr Pro Asp
            275                 280                 285

Phe Thr Ile Tyr Asn Ala Gly Gln Phe Pro Cys Asn Arg Tyr Thr His
            290                 295                 300

Tyr Met Thr Ser Ser Thr Ser Val Asp Leu Asn Leu Ala Arg Arg Glu
305                 310                 315                 320

Met Val Ile Leu Gly Thr Gln Tyr Ala Gly Glu Met Lys Lys Gly Leu
            325                 330                 335

Phe Ser Val Met His Tyr Leu Met Pro Lys Arg Arg Ile Leu Ser Leu
            340                 345                 350

His Ser Gly Cys Asn Met Gly Lys Asp Gly Asp Val Ala Leu Phe Phe
            355                 360                 365

Gly Leu Ser Gly Thr Gly Lys Thr Thr Leu Ser Thr Asp His Asn Arg
            370                 375                 380

Tyr Leu Ile Gly Asp Asp Glu His Cys Trp Thr Glu Thr Gly Val Ser
385                 390                 395                 400

Asn Ile Glu Gly Gly Cys Tyr Ala Lys Cys Val Asp Leu Ser Arg Glu
            405                 410                 415

Lys Glu Pro Asp Ile Trp Asn Ala Ile Lys Phe Gly Thr Val Leu Glu
            420                 425                 430

Asn Val Val Phe Asp Glu His Thr Arg Glu Val Asp Tyr Ser Asp Lys
            435                 440                 445

Ser Val Thr Glu Asn Thr Arg Ala Ala Tyr Pro Ile Glu Phe Ile Pro
450                 455                 460

Asn Ala Lys Ile Pro Cys Val Gly Pro His Pro Thr Asn Val Ile Leu
465                 470                 475                 480

Leu Ala Cys Asp Ala Phe Gly Val Leu Pro Pro Val Ser Lys Leu Asn
            485                 490                 495

Leu Ala Gln Thr Met Tyr His Phe Ile Ser Gly Tyr Thr Ala Leu Val
            500                 505                 510

Ala Gly Thr Glu Asp Gly Ile Lys Glu Pro Thr Ala Thr Phe Ser Ala
            515                 520                 525

Cys Phe Gly Ala Ala Phe Ile Met Leu His Pro Thr Lys Tyr Ala Ala
            530                 535                 540

Met Leu Ala Glu Lys Met Lys Ser Gln Gly Ala Thr Gly Trp Leu Val
545                 550                 555                 560

Asn Thr Gly Trp Ser Gly Gly Ser Tyr Gly Val Gly Asn Arg Ile Lys
            565                 570                 575

Leu Ala Tyr Thr Arg Lys Ile Ile Asp Ala Ile His Ser Gly Ser Leu
            580                 585                 590

Leu Lys Ala Asn Tyr Lys Lys Thr Glu Ile Phe Gly Phe Glu Ile Pro
            595                 600                 605
```

```
Thr Glu Ile Glu Gly Ile Pro Ser Glu Ile Leu Asp Pro Val Asn Ser
    610                 615                 620
Trp Ser Asp Lys Lys Ala His Lys Asp Thr Leu Val Lys Leu Gly Gly
625                 630                 635                 640
Leu Phe Lys Lys Asn Phe Glu Val Phe Ala Asn His Lys Ile Gly Val
                645                 650                 655
Asp Gly Lys Leu Thr Glu Glu Ile Leu Ala Ala Gly Pro Ile Phe
            660                 665                 670

<210> SEQ ID NO 15
<211> LENGTH: 2340
<212> TYPE: DNA
<213> ORGANISM: Arabidopsis thaliana

<400> SEQUENCE: 15
```

| | | | | |
|---|---|---|---|---|
| atggtttcgt ttacgggttt cgctttcgta tttggaattc tacttgggat tcttgcgatc | 60 |
| gttacggcgg aagttgtagg gttttttgtat cttctgaagc gattgaatcg aaaagagat | 120 |
| cgtcaggaat cgaattcgag ttctgatcca aacttcaaga gttttgatcc tcgccaatcc | 180 |
| attgatttta gtctcaacaa acagggagtg atctggtat tggaattaga tgaaaatgta | 240 |
| aaagattgga tgaaggagaa attaccaaaa gagcaaaaga agaagagagt agatctcttg | 300 |
| gaggtacatc cagttaggag atttgctcgc atcaaagatc ataagctcat cttgtctgat | 360 |
| tcattagatg gccctcagac tcctattact ttgaaaggtt gctttgttga cgctgtttca | 420 |
| ggctctggac caacaaggaa atgggctaaa agatttccta tacaagtaga aagcaaaact | 480 |
| tctgtcttgt ataaggaaa cagagtgttt tacattttct tagagacttc ttgggagaag | 540 |
| gagtcatggt gtaaagctct tcgtcttgct gcttgcgaga atcaggaaag gtttatttgg | 600 |
| tccaccaaat tgaaagaaga tttccggaac tatctggctt cccttaatgc tgcctatcct | 660 |
| tcttttatga aaccatcagc tgggtttagt tttgagtcat ggacaagggg cttaaagca | 720 |
| gatggtcctt catcaaaggt tcgtttgatc tggaagaaat tttcgaaaaa gtgctcaact | 780 |
| aaagtgaatt ttccccgtc gattcgtgac gacaagaaga cttcatcccg ttcttaccaa | 840 |
| gattcacaat ctactggtag ctctggaaag agtacctcag caaggaggat gcaagataac | 900 |
| atcccggagg aaactgatgt ccaagttatc tcacgttctt ggagccatag cagtcatgca | 960 |
| tcagatgtag attcagaaga caagtctttt gatgaaggaa cattggcatt gaacgtagta | 1020 |
| ttatctcggc tgttttttga tgttaaacag aacacagtac tgaagaattt agtgcgcgaa | 1080 |
| cgaatccagc ggataatgtc caacatgaga attcccagct acataggcga attaatctgc | 1140 |
| tgtgacgtag acattggaaa tctcccgcct tacatacacg gtacgagaat tcttccaatg | 1200 |
| gagatgaatg gtgtgtgggc gttcgaaata gatattgaat acactggtgg tgcgggactt | 1260 |
| gaagttgaaa ctcgggttga tgctcgagag gaagatttgc agaaaggcat agctgaggga | 1320 |
| aagttgcagc caaattctgc tggggatgtt ccaccagatc tccttgaagg tcttgcagat | 1380 |
| tttgaaaagc aattaaatgt tcccggagga actgttgatg cacaagatgt gaaaagtggt | 1440 |
| ggaactgata agctgatga atcgaagggt ccaaaaggta caaaaacagg ttcgagcaat | 1500 |
| ggatccaagt ggaagtctat gctgaagaac atcgttgaac aagtttccca ggtcccaatt | 1560 |
| actttgtcta taggggtgtc ttcgcttcga gggacactgt gtgtacacat gaagccgcct | 1620 |
| ccatctgatc aactgtggtt tggcttcaca agcatgcctg atattgaatt caaccttgtc | 1680 |
| tcttctgttg gtgaacacaa aatcacaaac agccatgttg ctatgttctt ggtcaaccgg | 1740 |
| ttcaagacgg cgatacgaga cgtcatggtg ctccccaatt gtgaaagcgt taccattcct | 1800 |

```
tggatgacag ctgaaaagga tgattgggtc gaacgcaatg tcgctccatt catgtggctg    1860
aatcaagact ccaccagtga tcgcgaaaat ttggaagctg cagaagcgaa atctaaagct    1920
gacaagccac cgacttctga acaaatgcag aaaactgtca acatcccgca gaagcctaga    1980
attgaggaag aatctgtgtc ggctgacact gcaccatcag ctaattccat agctctccta    2040
gtagagagtg acaaatcctt agaagaactc aagactccac tgctggaaag cagcgaaaag    2100
catgatacaa tagcgagagg aggcagtgcg ggagatataa ttccgggtat tggtcaatca    2160
ccgtctatgt cgactgtttc gggtgaagag gatgattcaa attcaaaagg aagaaaatg    2220 ggggcagcaa aggcgaggat gttcgatttt aggaagaaag tgggagagaa gtttgaagag    2280
aagaaacgtc acgttgagga aaaaagtaga cagattgttg aaaagatgag aggaccttga    2340
```

<210> SEQ ID NO 16
<211> LENGTH: 779
<212> TYPE: PRT
<213> ORGANISM: Arabidopsis thaliana

<400> SEQUENCE: 16

```
Met Val Ser Phe Thr Gly Phe Ala Phe Val Phe Gly Ile Leu Leu Gly
 1               5                  10                  15

Ile Leu Ala Ile Val Thr Ala Glu Val Val Gly Phe Leu Tyr Leu Leu
            20                  25                  30

Lys Arg Leu Asn Arg Lys Arg Asp Arg Gln Glu Ser Asn Ser Ser Ser
        35                  40                  45

Asp Pro Asn Phe Lys Ser Phe Asp Pro Arg Gln Ser Ile Asp Phe Ser
    50                  55                  60

Leu Asn Lys Gln Gly Val Ile Trp Ile Leu Glu Leu Asp Glu Asn Val
65                  70                  75                  80

Lys Asp Trp Met Lys Glu Lys Leu Pro Lys Glu Gln Lys Lys Lys Arg
                85                  90                  95

Val Asp Leu Leu Glu Val His Pro Val Arg Arg Phe Ala Arg Ile Lys
            100                 105                 110

Asp His Lys Leu Ile Leu Ser Asp Ser Leu Asp Gly Pro Gln Thr Pro
        115                 120                 125

Ile Thr Leu Lys Gly Cys Phe Val Asp Ala Val Ser Gly Ser Gly Pro
    130                 135                 140

Thr Arg Lys Trp Ala Lys Arg Phe Pro Ile Gln Val Glu Ser Lys Thr
145                 150                 155                 160

Ser Val Leu Tyr Lys Gly Asn Arg Val Phe Tyr Ile Phe Leu Glu Thr
                165                 170                 175

Ser Trp Glu Lys Glu Ser Trp Cys Lys Ala Leu Arg Leu Ala Ala Cys
            180                 185                 190

Glu Asn Gln Glu Arg Phe Ile Trp Ser Thr Lys Leu Lys Glu Asp Phe
        195                 200                 205

Arg Asn Tyr Leu Ala Ser Leu Asn Ala Ala Tyr Pro Ser Phe Met Lys
    210                 215                 220

Pro Ser Ala Gly Phe Ser Phe Glu Ser Leu Asp Lys Gly Leu Lys Ala
225                 230                 235                 240

Asp Gly Pro Ser Ser Lys Val Arg Leu Ile Trp Lys Lys Phe Ser Lys
                245                 250                 255

Lys Cys Ser Thr Lys Val Asn Phe Pro Pro Ser Ile Arg Asp Asp Lys
            260                 265                 270

Lys Thr Ser Ser Arg Ser Tyr Gln Asp Ser Gln Ser Thr Gly Ser Ser
        275                 280                 285
```

```
Gly Lys Ser Thr Ser Ala Arg Arg Met Gln Asp Asn Ile Pro Glu Glu
    290                 295                 300

Thr Asp Val Gln Val Ile Ser Arg Ser Trp Ser His Ser Ser His Ala
305                 310                 315                 320

Ser Asp Val Asp Ser Glu Asp Lys Ser Phe Asp Glu Gly Thr Leu Ala
                325                 330                 335

Leu Asn Val Val Leu Ser Arg Leu Phe Phe Asp Val Lys Gln Asn Thr
            340                 345                 350

Val Leu Lys Asn Leu Val Arg Glu Arg Ile Gln Arg Ile Met Ser Asn
        355                 360                 365

Met Arg Ile Pro Ser Tyr Ile Gly Glu Leu Ile Cys Cys Asp Val Asp
    370                 375                 380

Ile Gly Asn Leu Pro Pro Tyr Ile His Gly Thr Arg Ile Leu Pro Met
385                 390                 395                 400

Glu Met Asn Gly Val Trp Ala Phe Glu Ile Asp Ile Glu Tyr Thr Gly
                405                 410                 415

Gly Ala Gly Leu Glu Val Glu Thr Arg Val Asp Ala Arg Glu Glu Asp
            420                 425                 430

Leu Gln Lys Gly Ile Ala Glu Gly Lys Leu Gln Pro Asn Ser Ala Gly
        435                 440                 445

Asp Val Pro Pro Asp Leu Leu Glu Gly Leu Ala Asp Phe Glu Lys Gln
    450                 455                 460

Leu Asn Val Pro Gly Gly Thr Val Asp Ala Gln Asp Val Lys Ser Gly
465                 470                 475                 480

Gly Thr Asp Lys Ala Asp Glu Ser Lys Gly Pro Lys Gly Thr Lys Thr
                485                 490                 495

Gly Ser Ser Asn Gly Ser Lys Trp Lys Ser Met Leu Lys Asn Ile Val
            500                 505                 510

Glu Gln Val Ser Gln Val Pro Ile Thr Leu Ser Ile Gly Val Ser Ser
        515                 520                 525

Leu Arg Gly Thr Leu Cys Val His Met Lys Pro Pro Ser Asp Gln
    530                 535                 540

Leu Trp Phe Gly Phe Thr Ser Met Pro Asp Ile Glu Phe Asn Leu Val
545                 550                 555                 560

Ser Ser Val Gly Glu His Lys Ile Thr Asn Ser His Val Ala Met Phe
                565                 570                 575

Leu Val Asn Arg Phe Lys Thr Ala Ile Arg Asp Val Met Val Leu Pro
            580                 585                 590

Asn Cys Glu Ser Val Thr Ile Pro Trp Met Thr Ala Glu Lys Asp Asp
        595                 600                 605

Trp Val Glu Arg Asn Val Ala Pro Phe Met Trp Leu Asn Gln Asp Ser
    610                 615                 620

Thr Ser Asp Arg Glu Asn Leu Glu Ala Ala Glu Ala Lys Ser Lys Ala
625                 630                 635                 640

Asp Lys Pro Pro Thr Ser Glu Gln Met Gln Lys Thr Val Asn Ile Pro
                645                 650                 655

Gln Lys Pro Arg Ile Glu Glu Glu Ser Val Ser Ala Asp Thr Ala Pro
            660                 665                 670

Ser Ala Asn Ser Ile Ala Leu Leu Val Glu Ser Asp Lys Ser Leu Glu
        675                 680                 685

Glu Leu Lys Thr Pro Leu Leu Glu Ser Ser Lys His Asp Thr Ile
    690                 695                 700

Ala Arg Gly Gly Ser Ala Gly Asp Ile Ile Pro Gly Ile Gly Gln Ser
```

```
                   705                 710                 715                 720
        Pro Ser Met Ser Thr Val Ser Gly Glu Glu Asp Asp Ser Asn Ser Lys
                            725                 730                 735

Gly Lys Lys Met Gly Ala Ala Lys Ala Arg Met Phe Asp Phe Arg Lys
                        740                 745                 750

Lys Val Gly Glu Lys Phe Glu Glu Lys Lys Arg His Val Glu Glu Lys
                    755                 760                 765

Ser Arg Gln Ile Val Glu Lys Met Arg Gly Pro
                770                 775

<210> SEQ ID NO 17
<211> LENGTH: 1674
<212> TYPE: DNA
<213> ORGANISM: Arabidopsis thaliana

<400> SEQUENCE: 17
atgaaaccat cagctgggtt tagttttgag tcattggaca aggggcttaa agcagatggt      60
ccttcatcaa aggttcgttt gatctggaag aaattttcga aaaagtgctc aactaaagtg     120
aattttcccc cgtcgattcg tgacgacaag aagacttcat cccgttctta ccaagattca     180
caatctactg gtagctctgg aaagagtacc tcagcaagga ggatgcaaga taacatcccg     240
gaggaaactg atgtccaagt tatctcacgt tcttggagcc atagcagtca tgcatcagat     300
gtagattcag aagacaagtc ttttgatgaa ggaacattgg cattgaacgt agtattatct     360
cggctgtttt tgatgttaa acagaacaca gtactgaaga attagtgcg cgaacgaatc      420 cagcggataa tgtccaacat gagaattccc agctacatag gcgaattaat ctgctgtgac     480
gtagacattg gaaatctccc gccttacata cacggtacga gaattcttcc aatggagatg     540
aatggtgtgt gggcgttcga aatagatatt gaatacactg tggtgcgggg acttgaagtt     600
gaaactcggg ttgatgctcg agaggaagat ttgcagaaag gcatagctga gggaaagttg     660
cagccaaatt ctgctgggga tgttccacca gatctccttg aaggtcttgc agattttgaa     720
aagcaattaa atgttcccgg aggaactgtt gatgcacaag atgtgaaaag tggtggaact     780
gataaagctg atgaatcgaa gggtccaaaa ggtacaaaaa caggttcgag caatggatcc     840
aagtggaagt ctatgctgaa gaacatcgtt gaacaagttt cccaggtccc aattactttg     900 tctataggg tgtcttcgct tcgagggaca ctgtgtgtac acatgaagcc gcctccatct     960
gatcaactgt ggtttggctt cacaagcatg cctgatattg aattcaacct tgtctcttct    1020
gttggtgaac acaaaatcac aaacagccat gttgctatgt tcttggtcaa ccggttcaag    1080
acggcgatac gagacgtcat ggtgctcccc aattgtgaaa gcgttaccat tccttggatg    1140
acagctgaaa aggatgattg ggtcgaacgc aatgtcgctc cattcatgtg gctgaatcaa    1200
gactccacca gtgatcgcga aaatttggaa gctgcagaag cgaagtctaa agctgacaag    1260
ccaccgactt ctgaacaaat gcagaaaact gtcaacatcc gcagaagcc tagaattgag    1320 gaagaatctg tgtcggctga cactgcacca tcagctaatt ccatagctct cctagtagag    1380
agtgacaaat ccttagaaga actcaagact ccactgctgg aaagcagcga aaagcatgat    1440
acaatagcga gaggaggcag tgcgggagat ataattccgg gtattggtca atcaccgtct    1500
atgtcgactt tttcgggtga agaggatgat tcaaattcaa aaggaaagaa atgggggca     1560 gcaaaggcga ggatgttcga tttaggaag aaagtgggag agaagtttga agagaagaaa    1620
cgtcacgttg aggaaaaaag tagacagatt gttgaaaaga tgagaggacc ttga          1674

<210> SEQ ID NO 18
```

<211> LENGTH: 557
<212> TYPE: PRT
<213> ORGANISM: Arabidopsis thaliana

<400> SEQUENCE: 18

```
Met Lys Pro Ser Ala Gly Phe Ser Phe Glu Ser Leu Asp Lys Gly Leu
 1               5                  10                  15

Lys Ala Asp Gly Pro Ser Ser Lys Val Arg Leu Ile Trp Lys Lys Phe
             20                  25                  30

Ser Lys Lys Cys Ser Thr Lys Val Asn Phe Pro Pro Ser Ile Arg Asp
         35                  40                  45

Asp Lys Lys Thr Ser Ser Arg Ser Tyr Gln Asp Ser Gln Ser Thr Gly
     50                  55                  60

Ser Ser Gly Lys Ser Thr Ser Ala Arg Arg Met Gln Asp Asn Ile Pro
 65                  70                  75                  80

Glu Glu Thr Asp Val Gln Val Ile Ser Arg Ser Trp Ser His Ser Ser
                 85                  90                  95

His Ala Ser Asp Val Asp Ser Glu Asp Lys Ser Phe Asp Glu Gly Thr
            100                 105                 110

Leu Ala Leu Asn Val Val Leu Ser Arg Leu Phe Phe Asp Val Lys Gln
        115                 120                 125

Asn Thr Val Leu Lys Asn Leu Val Arg Glu Arg Ile Gln Arg Ile Met
    130                 135                 140

Ser Asn Met Arg Ile Pro Ser Tyr Ile Gly Glu Leu Ile Cys Cys Asp
145                 150                 155                 160

Val Asp Ile Gly Asn Leu Pro Pro Tyr Ile His Gly Thr Arg Ile Leu
                165                 170                 175

Pro Met Glu Met Asn Gly Val Trp Ala Phe Glu Ile Asp Ile Glu Tyr
            180                 185                 190

Thr Gly Gly Ala Gly Leu Glu Val Glu Thr Arg Val Asp Ala Arg Glu
        195                 200                 205

Glu Asp Leu Gln Lys Gly Ile Ala Glu Gly Lys Leu Gln Pro Asn Ser
    210                 215                 220

Ala Gly Asp Val Pro Pro Asp Leu Leu Glu Gly Leu Ala Asp Phe Glu
225                 230                 235                 240

Lys Gln Leu Asn Val Pro Gly Gly Thr Val Asp Ala Gln Asp Val Lys
                245                 250                 255

Ser Gly Gly Thr Asp Lys Ala Asp Glu Ser Lys Gly Pro Lys Gly Thr
            260                 265                 270

Lys Thr Gly Ser Ser Asn Gly Ser Lys Trp Lys Ser Met Leu Lys Asn
        275                 280                 285

Ile Val Glu Gln Val Ser Gln Val Pro Ile Thr Leu Ser Ile Gly Val
    290                 295                 300

Ser Ser Leu Arg Gly Thr Leu Cys Val His Met Lys Pro Pro Pro Ser
305                 310                 315                 320

Asp Gln Leu Trp Phe Gly Phe Thr Ser Met Pro Asp Ile Glu Phe Asn
                325                 330                 335

Leu Val Ser Ser Val Gly Glu His Lys Ile Thr Asn Ser His Val Ala
            340                 345                 350

Met Phe Leu Val Asn Arg Phe Lys Thr Ala Ile Arg Asp Val Met Val
        355                 360                 365

Leu Pro Asn Cys Glu Ser Val Thr Ile Pro Trp Met Thr Ala Glu Lys
    370                 375                 380

Asp Asp Trp Val Glu Arg Asn Val Ala Pro Phe Met Trp Leu Asn Gln
385                 390                 395                 400
```

```
Asp Ser Thr Ser Asp Arg Glu Asn Leu Glu Ala Ala Glu Ala Lys Ser
                405                 410                 415

Lys Ala Asp Lys Pro Pro Thr Ser Glu Gln Met Gln Lys Thr Val Asn
            420                 425                 430

Ile Pro Gln Lys Pro Arg Ile Glu Glu Ser Val Ser Ala Asp Thr
        435                 440                 445

Ala Pro Ser Ala Asn Ser Ile Ala Leu Leu Val Glu Ser Asp Lys Ser
    450                 455                 460

Leu Glu Glu Leu Lys Thr Pro Leu Leu Glu Ser Ser Glu Lys His Asp
465                 470                 475                 480

Thr Ile Ala Arg Gly Gly Ser Ala Gly Asp Ile Pro Gly Ile Gly
                485                 490                 495

Gln Ser Pro Ser Met Ser Thr Val Ser Gly Glu Glu Asp Asp Ser Asn
                500                 505                 510

Ser Lys Gly Lys Lys Met Gly Ala Ala Lys Ala Arg Met Phe Asp Phe
            515                 520                 525

Arg Lys Lys Val Gly Glu Lys Phe Glu Glu Lys Lys Arg His Val Glu
530                 535                 540

Glu Lys Ser Arg Gln Ile Val Glu Lys Met Arg Gly Pro
545                 550                 555
```

<210> SEQ ID NO 19
<211> LENGTH: 1722
<212> TYPE: DNA
<213> ORGANISM: Arabidopsis thaliana

<400> SEQUENCE: 19

| | | | | | |
|---|---|---|---|---|---|
| atggtcgata | aaccaaatca | gataatggaa | gaagaaggga | gattcgaagc | ggaggttgcg | 60 |
| gaagtgcaga | cttggtggag | ctcagagagg | ttcaagctaa | caaggcgccc | ttacactgcc | 120 |
| cgtgacgtgg | tggctctacg | tggccatctc | aagcaaggct | atgcttcgaa | cgagatggct | 180 |
| aagaagctgt | ggagaacgct | caaaagccat | caagccaacg | gtacggcctc | tcgcaccttc | 240 |
| ggagcgttgg | accctgttca | ggtgaccatg | atggctaaac | attggacac | catctatgtc | 300 |
| tctggttggc | agtgctcgtc | cactcacaca | tccactaatg | agcctggtcc | tgatcttgct | 360 |
| gattatccgt | acgacaccgt | tcctaacaag | gttgaacacc | tcttcttcgc | tcagcagtac | 420 |
| catgacagaa | agcagaggga | ggcaagaatg | agcatgagca | gagaagagag | gacaaaaact | 480 |
| ccgttcgtgg | actacctaaa | gcccatcatc | gccgacggag | acaccggctt | tggcggcacc | 540 |
| accgccaccg | tcaaactctg | caagcttttc | gttgaaagag | gcgccgctgg | ggtccacatc | 600 |
| gaggaccagt | cctccgtcac | caagaagtgt | ggccacatgg | ccggaaaggt | cctcgtggca | 660 |
| gtcagcgaac | acatcaaccg | ccttgtcgcg | gctcggctcc | agttcgacgt | gatgggtaca | 720 |
| gagaccgtcc | ttgttgctag | aacagatgcg | gtcgcagcta | ctctgatcca | gtcgaacatt | 780 |
| gacgcgaggg | accaccagtt | catcctcggt | gccactaacc | cgagccttag | aggcaagagt | 840 |
| ttgtcctcgc | ttctggctga | gggaatgact | gtaggcaaga | atggtccggc | gttgcaatcc | 900 |
| attgaagatc | agtggcttgg | ctcggccggt | cttatgactt | tctcggaagc | tgtcgtgcag | 960 |
| gccatcaagc | gcatgaacct | caacgagaac | gagaagaatc | agagactgag | cgagtggtta | 1020 |
| acccatgcaa | ggtatgagaa | ctgcctgtca | aatgagcaag | gccgagtgtt | agcagcaaaa | 1080 |
| cttggtgtga | cagatctttt | ctgggactgg | gacttgccga | gaaccagaga | aggattctac | 1140 |
| cggttccaag | gctcggtcgc | agcggccgtg | gtccgtggct | gggccttgc | acagatcgca | 1200 |
| gacatcatct | ggatggaaac | ggcaagccct | gatctcaatg | aatgcaccca | attcgccgaa | 1260 |

```
ggtatcaagt ccaagacacc ggaggtcatg ctcgcctaca atctctcgcc gtccttcaac    1320
tgggacgctt ccggtatgac ggatcagcag atggttgagt cattccgcg gattgctagg     1380 ctcggatatt gttggcagtt cataacgctt gcgggtttcc atgcggatgc tcttgtggtt    1440
gatacatttg caaaggatta cgctaggcgc gggatgttgg cttatgtgga gaggatacaa    1500
agagaagaga ggacccatgg ggttgacact ttggctcacc agaaatggtc cggtgctaat    1560
tactatgatc gttatcttaa gaccgtccaa ggtggaatct cctccactgc agccatggga    1620
aaaggtgtca ctgaagaaca gttcaaggag agttggacaa ggccgggagc tgatggaatg    1680
ggtgaaggga ctagccttgt ggtcgccaag tcaagaatgt aa                       1722
```

<210> SEQ ID NO 20
<211> LENGTH: 573
<212> TYPE: PRT
<213> ORGANISM: Arabidopsis thaliana

<400> SEQUENCE: 20

```
Met Val Asp Lys Pro Asn Gln Ile Met Glu Glu Gly Arg Phe Glu
 1               5                  10                  15

Ala Glu Val Ala Glu Val Gln Thr Trp Trp Ser Ser Glu Arg Phe Lys
                20                  25                  30

Leu Thr Arg Arg Pro Tyr Thr Ala Arg Asp Val Val Ala Leu Arg Gly
            35                  40                  45

His Leu Lys Gln Gly Tyr Ala Ser Asn Glu Met Ala Lys Lys Leu Trp
        50                  55                  60

Arg Thr Leu Lys Ser His Gln Ala Asn Gly Thr Ala Ser Arg Thr Phe
 65                  70                  75                  80

Gly Ala Leu Asp Pro Val Gln Val Thr Met Met Ala Lys His Leu Asp
                85                  90                  95

Thr Ile Tyr Val Ser Gly Trp Gln Cys Ser Ser Thr His Thr Ser Thr
            100                 105                 110

Asn Glu Pro Gly Pro Asp Leu Ala Asp Tyr Pro Tyr Asp Thr Val Pro
        115                 120                 125

Asn Lys Val Glu His Leu Phe Phe Ala Gln Gln Tyr His Asp Arg Lys
    130                 135                 140

Gln Arg Glu Ala Arg Met Ser Met Ser Arg Glu Glu Arg Thr Lys Thr
145                 150                 155                 160

Pro Phe Val Asp Tyr Leu Lys Pro Ile Ile Ala Asp Gly Asp Thr Gly
                165                 170                 175

Phe Gly Gly Thr Thr Ala Thr Val Lys Leu Cys Lys Leu Phe Val Glu
            180                 185                 190

Arg Gly Ala Ala Gly Val His Ile Glu Asp Gln Ser Ser Val Thr Lys
        195                 200                 205

Lys Cys Gly His Met Ala Gly Lys Val Leu Val Ala Val Ser Glu His
    210                 215                 220

Ile Asn Arg Leu Val Ala Ala Arg Leu Gln Phe Asp Val Met Gly Thr
225                 230                 235                 240

Glu Thr Val Leu Val Ala Arg Thr Asp Ala Val Ala Ala Thr Leu Ile
                245                 250                 255

Gln Ser Asn Ile Asp Ala Arg Asp His Gln Phe Ile Leu Gly Ala Thr
            260                 265                 270

Asn Pro Ser Leu Arg Gly Lys Ser Leu Ser Ser Leu Leu Ala Glu Gly
        275                 280                 285

Met Thr Val Gly Lys Asn Gly Pro Ala Leu Gln Ser Ile Glu Asp Gln
```

```
                290             295             300
Trp Leu Gly Ser Ala Gly Leu Met Thr Phe Ser Glu Ala Val Val Gln
305                 310                 315                 320

Ala Ile Lys Arg Met Asn Leu Asn Glu Asn Glu Lys Asn Gln Arg Leu
                325                 330                 335

Ser Glu Trp Leu Thr His Ala Arg Tyr Glu Asn Cys Leu Ser Asn Glu
            340                 345                 350

Gln Gly Arg Val Leu Ala Ala Lys Leu Gly Val Thr Asp Leu Phe Trp
        355                 360                 365

Asp Trp Asp Leu Pro Arg Thr Arg Glu Gly Phe Tyr Arg Phe Gln Gly
370                 375                 380

Ser Val Ala Ala Val Val Arg Gly Trp Ala Phe Ala Gln Ile Ala
385                 390                 395                 400

Asp Ile Ile Trp Met Glu Thr Ala Ser Pro Asp Leu Asn Glu Cys Thr
                405                 410                 415

Gln Phe Ala Glu Gly Ile Lys Ser Lys Thr Pro Glu Val Met Leu Ala
                420                 425                 430

Tyr Asn Leu Ser Pro Ser Phe Asn Trp Asp Ala Ser Gly Met Thr Asp
            435                 440                 445

Gln Gln Met Val Glu Phe Ile Pro Arg Ile Ala Arg Leu Gly Tyr Cys
        450                 455                 460

Trp Gln Phe Ile Thr Leu Ala Gly Phe His Ala Asp Ala Leu Val Val
465                 470                 475                 480

Asp Thr Phe Ala Lys Asp Tyr Ala Arg Arg Gly Met Leu Ala Tyr Val
                485                 490                 495

Glu Arg Ile Gln Arg Glu Glu Arg Thr His Gly Val Asp Thr Leu Ala
                500                 505                 510

His Gln Lys Trp Ser Gly Ala Asn Tyr Tyr Asp Arg Tyr Leu Lys Thr
            515                 520                 525

Val Gln Gly Gly Ile Ser Ser Thr Ala Ala Met Gly Lys Gly Val Thr
        530                 535                 540

Glu Glu Gln Phe Lys Glu Ser Trp Thr Arg Pro Gly Ala Asp Gly Met
545                 550                 555                 560

Gly Glu Gly Thr Ser Leu Val Val Ala Lys Ser Arg Met
                565                 570

<210> SEQ ID NO 21
<211> LENGTH: 897
<212> TYPE: DNA
<213> ORGANISM: Arabidopsis thaliana

<400> SEQUENCE: 21 atgggggttag agaggaaagt gtacggtttg gttatggtat ctttggtact tatggctatt      60
gcaacgatgt gttgtgtcca agctacgatc gaggaagaag cggctaagga tgaatcatgg     120
actgattggg caaaggagaa gatcggtctc aagcacgaag acaacatcca acccactcac     180
accaccacga ccgttcaaga cgacgcttgg agagcgagtc aaaaagccga ggacgcaaag     240
gaggcggcta aacgcaaagc agaggaagcg gttggagccg cgaaggagaa agcgggttcg     300
gcatacgaga cagctaaatc gaaagttgag gagggtttgg cttctgtaaa agacaaggcc     360
tcgcagagtt acgactcagc tggtcaagtt aaggatgacg tgtctcacaa gtcaaagcaa     420
gttaaagata gcttgtcggg agacgaaaac gatgagtctt ggaccggttg ggccaaagag     480
aaaatcggaa tcaagaacga agacatcaac agccctaact gggagagac ggtatctgag      540 aaggcaaaag aagctaagga agcggctaaa cgcaaagcag agatgctaa agagaagttg       600
```

```
gcggagacag ttgagacggc gaaagagaag gcgagcgata tgacgagtgc agctaaggag    660
aaggcggaga agttgaagga ggaagcagag agagagagta agagtgcgaa ggagaaaatt    720
aaagaaagtt atgagactgc aaaatcaaaa gccgatgaga ctttagagtc cgcgaaagat    780
aaggcgtcgc agagttacga ctcagctgcg cgtaaatcgg aggaagctaa agataccgcg    840
tctcacaagt caaacgtgt taaagagagc ttgaccgacg atgatgctga gctctga       897
```

<210> SEQ ID NO 22
<211> LENGTH: 298
<212> TYPE: PRT
<213> ORGANISM: Arabidopsis thaliana

<400> SEQUENCE: 22

```
Met Gly Leu Glu Arg Lys Val Tyr Gly Leu Val Met Val Ser Leu Val
 1               5                  10                  15

Leu Met Ala Ile Ala Thr Met Cys Cys Val Gln Ala Thr Ile Glu Glu
             20                  25                  30

Glu Ala Ala Lys Asp Glu Ser Trp Thr Asp Trp Ala Lys Glu Lys Ile
         35                  40                  45

Gly Leu Lys His Glu Asp Asn Ile Gln Pro Thr His Thr Thr Thr Thr
     50                  55                  60

Val Gln Asp Asp Ala Trp Arg Ala Ser Gln Lys Ala Glu Asp Ala Lys
 65                  70                  75                  80

Glu Ala Ala Lys Arg Lys Ala Glu Glu Ala Val Gly Ala Ala Lys Glu
                 85                  90                  95

Lys Ala Gly Ser Ala Tyr Glu Thr Ala Lys Ser Lys Val Glu Glu Gly
            100                 105                 110

Leu Ala Ser Val Lys Asp Lys Ala Ser Gln Ser Tyr Asp Ser Ala Gly
        115                 120                 125

Gln Val Lys Asp Asp Val Ser His Lys Ser Lys Gln Val Lys Asp Ser
    130                 135                 140

Leu Ser Gly Asp Glu Asn Asp Glu Ser Trp Thr Gly Trp Ala Lys Glu
145                 150                 155                 160

Lys Ile Gly Ile Lys Asn Glu Asp Ile Asn Ser Pro Asn Leu Gly Glu
                165                 170                 175

Thr Val Ser Glu Lys Ala Lys Glu Ala Lys Glu Ala Lys Arg Lys
            180                 185                 190

Ala Gly Asp Ala Lys Glu Lys Leu Ala Glu Thr Val Glu Thr Ala Lys
        195                 200                 205

Glu Lys Ala Ser Asp Met Thr Ser Ala Ala Lys Glu Lys Ala Glu Lys
    210                 215                 220

Leu Lys Glu Glu Ala Glu Arg Glu Ser Lys Ser Ala Lys Glu Lys Ile
225                 230                 235                 240

Lys Glu Ser Tyr Glu Thr Ala Lys Ser Lys Ala Asp Glu Thr Leu Glu
                245                 250                 255

Ser Ala Lys Asp Lys Ala Ser Gln Ser Tyr Asp Ser Ala Ala Arg Lys
            260                 265                 270

Ser Glu Glu Ala Lys Asp Thr Ala Ser His Lys Ser Lys Arg Val Lys
        275                 280                 285

Glu Ser Leu Thr Asp Asp Ala Glu Leu
    290                 295
```

<210> SEQ ID NO 23
<211> LENGTH: 414
<212> TYPE: DNA

<213> ORGANISM: Arabidopsis thaliana

<400> SEQUENCE: 23

```
atggcgactc aattcagcgc ttctgtctca ttgcaaactt cttgtctggc aacaacaagg      60
attagtttcc aaaagccagc tttgatttcc aaccatggaa agactaatct atccttcaac     120
ctccgccgtt caatcccatc tcgccgcctc tctgtttctt gcgcggcaaa acaagagacg     180
atagagaaag tgtctgctat agttaagaag caactatcac ttacaccgga taaaaagtc      240
gttgcagaaa ccaaatttgc tgaccttgga gcagattctc tcgacacggt tgagatagta     300
atgggtttag aggaagagtt taacatccaa atggccgaag agaaagcaca gaagattgcc     360
acagttgagc aagctgctga actcattgaa gagctcatca cgagaagaa gtaa            414
```

<210> SEQ ID NO 24
<211> LENGTH: 137
<212> TYPE: PRT
<213> ORGANISM: Arabidopsis thaliana

<400> SEQUENCE: 24

```
Met Ala Thr Gln Phe Ser Ala Ser Val Ser Leu Gln Thr Ser Cys Leu
  1               5                  10                  15
Ala Thr Thr Arg Ile Ser Phe Gln Lys Pro Ala Leu Ile Ser Asn His
             20                  25                  30
Gly Lys Thr Asn Leu Ser Phe Asn Leu Arg Arg Ser Ile Pro Ser Arg
         35                  40                  45
Arg Leu Ser Val Ser Cys Ala Ala Lys Gln Glu Thr Ile Glu Lys Val
     50                  55                  60
Ser Ala Ile Val Lys Lys Gln Leu Ser Leu Thr Pro Asp Lys Lys Val
 65                  70                  75                  80
Val Ala Glu Thr Lys Phe Ala Asp Leu Gly Ala Asp Ser Leu Asp Thr
                 85                  90                  95
Val Glu Ile Val Met Gly Leu Glu Glu Glu Phe Asn Ile Gln Met Ala
                100                 105                 110
Glu Glu Lys Ala Gln Lys Ile Ala Thr Val Glu Gln Ala Ala Glu Leu
            115                 120                 125
Ile Glu Glu Leu Ile Asn Glu Lys Lys
        130                 135
```

<210> SEQ ID NO 25
<211> LENGTH: 903
<212> TYPE: DNA
<213> ORGANISM: Arabidopsis thaliana

<400> SEQUENCE: 25

```
atgccggcta ctagagtgtt aactgcagcg acggccgtga cccaaaccac ctcctgtttc      60
ctcgccaagc aagcttttca ctcttccggcg aagaaatcct gcggcggatt tggtggtctc    120
tgcttcagca gaagagctt ggtgttgaaa tctaagagac ctttctcctg cagtgccatt      180
tacaatcctc aggttaaggt tcaagaagaa ggtccggccg aatccctaga ttatcgagtt     240
ttcttcctcg atggttctgg aaagaaggtt tctccatggc atgatatacc attgaccta     300
ggcgatggag tttttcaactt tatagttgaa atacctaaag agtcaaaagc aaaaatggag    360
gttgctactg atgaagattt cactcctatt aagcaggata ctaagaaggg gaagctcaga    420
tattatccgt ataacattaa ctggaactat gggttgcttc ctcaaacatg gaagatcca     480
tctcatgcaa attctgaagt tgaaggatgt ttttggggata tgatccagt tgatgttgtt     540
gagattggtg aaacacaaag gaagataggc gatattctaa agataaagcc tttagctgct    600
```

```
ttagctatga ttgatgaagg tgagctagac tggaagattg ttgccatttc tttggatgac    660
ccaaaagctc atcttgtgaa tgatgttgaa gatgttgaga acatttccc gggtacacta    720 acagccatta gagactggtt tagagactac aagatcccag atggaaagcc tgctaacaga    780
tttggtcttg agacaaaacc agcaaacaaa gactatgctt tgaagatcat ccaagaaaca    840
aatgaatcat gggctaaact tgtgaagaga tcagttgatg ctggagtcct ttcactttac    900
tga                                                                 903
```

<210> SEQ ID NO 26
<211> LENGTH: 300
<212> TYPE: PRT
<213> ORGANISM: Arabidopsis thaliana

<400> SEQUENCE: 26

```
Met Pro Ala Thr Arg Val Leu Thr Ala Ala Thr Ala Val Thr Gln Thr
 1               5                  10                  15

Thr Ser Cys Phe Leu Ala Lys Gln Ala Phe Thr Leu Pro Ala Lys Lys
                20                  25                  30

Ser Cys Gly Gly Phe Gly Gly Leu Cys Phe Ser Arg Arg Ala Leu Val
            35                  40                  45

Leu Lys Ser Lys Arg Pro Phe Ser Cys Ser Ala Ile Tyr Asn Pro Gln
        50                  55                  60

Val Lys Val Gln Glu Glu Gly Pro Ala Glu Ser Leu Asp Tyr Arg Val
65                  70                  75                  80

Phe Phe Leu Asp Gly Ser Gly Lys Val Ser Pro Trp His Asp Ile
                85                  90                  95

Pro Leu Thr Leu Gly Asp Gly Val Phe Asn Phe Ile Val Glu Ile Pro
            100                 105                 110

Lys Glu Ser Lys Ala Lys Met Glu Val Ala Thr Asp Glu Asp Phe Thr
        115                 120                 125

Pro Ile Lys Gln Asp Thr Lys Lys Gly Lys Leu Arg Tyr Tyr Pro Tyr
    130                 135                 140

Asn Ile Asn Trp Asn Tyr Gly Leu Leu Pro Gln Thr Trp Glu Asp Pro
145                 150                 155                 160

Ser His Ala Asn Ser Glu Val Glu Gly Cys Phe Gly Asp Asn Asp Pro
                165                 170                 175

Val Asp Val Val Glu Ile Gly Glu Thr Gln Arg Lys Ile Gly Asp Ile
            180                 185                 190

Leu Lys Ile Lys Pro Leu Ala Ala Leu Ala Met Ile Asp Glu Gly Glu
        195                 200                 205

Leu Asp Trp Lys Ile Val Ala Ile Ser Leu Asp Asp Pro Lys Ala His
    210                 215                 220

Leu Val Asn Asp Val Glu Asp Val Lys His Phe Pro Gly Thr Leu
225                 230                 235                 240

Thr Ala Ile Arg Asp Trp Phe Arg Asp Tyr Lys Ile Pro Asp Gly Lys
                245                 250                 255

Pro Ala Asn Arg Phe Gly Leu Gly Asp Lys Pro Ala Asn Lys Asp Tyr
            260                 265                 270

Ala Leu Lys Ile Ile Gln Glu Thr Asn Glu Ser Trp Ala Lys Leu Val
        275                 280                 285

Lys Arg Ser Val Asp Ala Gly Val Leu Ser Leu Tyr
    290                 295                 300
```

<210> SEQ ID NO 27

<211> LENGTH: 2418
<212> TYPE: DNA
<213> ORGANISM: Arabidopsis thaliana

<400> SEQUENCE: 27

| | | | | | |
|---|---|---|---|---|---|
| atggcgtctt | tctttgatct | cgtatacata | agctggattg | gtttcttaaa | caaattcctc | 60 |
| tccttttggg | tcttctgggt | ttgccttgta | agatatgtag | cccagggaaa | ggggatattg | 120 |
| cagtcccacc | agctgattga | tgagttcctt | aagactgtga | agttgatgg | aacattagaa | 180 |
| gatcttaaca | aaagtccatt | catgaaagtt | ctgcaggaag | ccatagtttt | gcctccattt | 240 |
| gttgctttgg | ctatacgtcc | cagacctggt | gttagggaat | atgtccgtgt | gaatgtgtat | 300 |
| gagctgagcg | tagatcattt | aactgtttct | gaatatcttc | ggtttaagga | agagctcgtt | 360 |
| aatggccatg | ccaatggaga | ttatctcctt | gaacttgatt | ttgaaccttt | caatgcaaca | 420 |
| ttgcctcgcc | caactcgttc | atcatccatt | gggaatgggg | ttcagttcct | caatcgtcac | 480 |
| ctctcttcaa | ttatgttccg | taacaaagaa | agcatggagc | ctttgcttga | gtttctccgc | 540 |
| actcacaaac | atgatggccg | tcctatgatg | ctgaatgatc | gaatacagaa | tatccccata | 600 |
| cttcagggag | ctttggcaag | agcagaggag | ttcctttcta | aacttcctct | ggcaacacca | 660 |
| tactctgaat | tcgaatttga | actacaaggg | atgggatttg | aaaggggatg | gggtgacaca | 720 |
| gcacagaagg | tttcagaaat | ggtgcatctt | cttctggaca | tactccaggc | acctgatcct | 780 |
| tctgtcttgg | agacgtttct | aggaaggatt | cctatggtgt | tcaatgttgt | gattttgtct | 840 |
| ccgcatggtt | actttggcca | agccaatgtc | ttgggtctgc | ctgatactgg | tggacaggtt | 900 |
| gtctacattc | ttgatcaagt | acgtgcattg | gaaaatgaga | tgctccttag | gatacagaag | 960 |
| caaggactgg | aagttattcc | aaagattctc | attgtaacaa | gactgctacc | cgaagcaaag | 1020 |
| ggaacaacgt | gcaaccagag | gttagaaaga | gttagtggta | cagaacacgc | acacattctg | 1080 |
| cgaataccat | ttaggactga | aaagggaatt | cttcgcaagt | ggatctcaag | gtttgatgtc | 1140 |
| tggccatacc | tggagacttt | tgcagaggat | gcatcaaatg | aaatttctgc | ggagttgcag | 1200 |
| ggtgtaccaa | atctcatcat | tggcaactac | agtgatggaa | atctcgttgc | ttctttgtta | 1260 |
| gctagtaagc | taggtgtgat | acagtgtaat | attgctcatg | ctttagagaa | aaccaagtac | 1320 |
| cccgagtctg | acatttactg | gagaaaccat | gaagataagt | atcactttc | aagtcagttc | 1380 |
| actgcagatc | taattgccat | gaataatgcc | gatttcatca | tcaccagcac | ataccaagag | 1440 |
| attgcgggaa | gcaagaacaa | tgttgggcaa | tacgagagcc | acacagcttt | cactatgcct | 1500 |
| ggtctttacc | gagttgttca | tggaattgat | gtctttgatc | ctaagtttaa | tatagtctct | 1560 |
| ccaggagctg | atatgaccat | atactttcca | tattctgaca | aggaaagaag | actcactgcc | 1620 |
| cttcatgagt | caattgaaga | actcctcttt | agtgccgaac | agaatgatga | gcatgttggt | 1680 |
| ttactgagcg | accaatcgaa | gccaatcatc | ttctctatgg | caagacttga | cagggtgaaa | 1740 |
| aacttgactg | ggctagttga | atgctatgcc | aagaatagca | agcttagaga | gcttgcaaat | 1800 |
| cttgttatag | tcggtggcta | catcgatgag | aatcagtcca | gggatagaga | ggaaatggct | 1860 |
| gagatacaaa | agatgcacag | cctgattgag | cagtatgatt | tacacggtga | gtttaggtgg | 1920 |
| atagctgctc | aaatgaaccg | tgctcgaaat | ggtgagcttt | accgttatat | cgcagacaca | 1980 |
| aaaggtgttt | ttgttcagcc | tgcttttctat | gaagcatttg | gcttacggt | tgtggaatca | 2040 |
| atgacttgtg | cactcccaac | gtttgctacc | tgtcatggtg | gacccgcaga | gattatcgaa | 2100 |
| aacggagttt | ctgggttcca | cattgaccca | tatcatccag | accaggttgc | agctaccttg | 2160 |
| gtcagcttct | ttgagacctg | taacaccaat | ccaaatcatt | gggttaaaat | ctctgaagga | 2220 |

```
gggctcaagc gaatctatga aaggtacaca tggaagaagt actcagagag actgcttacc    2280
ctggctggag tctatgcatt ctggaaacat gtgtctaagc tcgaaggag agaaacacga     2340 cgttacctag agatgtttta ctcattgaaa tttcgtgatt tggccaattc aatcccgctg   2400
gcaacagatg agaactga                                                  2418
```

<210> SEQ ID NO 28
<211> LENGTH: 805
<212> TYPE: PRT
<213> ORGANISM: Arabidopsis thaliana

<400> SEQUENCE: 28

```
Met Ala Ser Phe Phe Asp Leu Val Tyr Ile Ser Trp Ile Gly Phe Leu
  1               5                  10                  15

Asn Lys Phe Leu Ser Phe Trp Val Phe Trp Val Cys Leu Val Arg Tyr
             20                  25                  30

Val Ala Gln Gly Lys Gly Ile Leu Gln Ser His Gln Leu Ile Asp Glu
         35                  40                  45

Phe Leu Lys Thr Val Lys Val Asp Gly Thr Leu Glu Asp Leu Asn Lys
     50                  55                  60

Ser Pro Phe Met Lys Val Leu Gln Glu Ala Ile Val Leu Pro Pro Phe
 65                  70                  75                  80

Val Ala Leu Ala Ile Arg Pro Arg Pro Gly Val Arg Glu Tyr Val Arg
                 85                  90                  95

Val Asn Val Tyr Glu Leu Ser Val Asp His Leu Thr Val Ser Glu Tyr
            100                 105                 110

Leu Arg Phe Lys Glu Glu Leu Val Asn Gly His Ala Asn Gly Asp Tyr
        115                 120                 125

Leu Leu Glu Leu Asp Phe Glu Pro Phe Asn Ala Thr Leu Pro Arg Pro
    130                 135                 140

Thr Arg Ser Ser Ser Ile Gly Asn Gly Val Gln Phe Leu Asn Arg His
145                 150                 155                 160

Leu Ser Ser Ile Met Phe Arg Asn Lys Glu Ser Met Glu Pro Leu Leu
                165                 170                 175

Glu Phe Leu Arg Thr His Lys His Asp Gly Arg Pro Met Met Leu Asn
            180                 185                 190

Asp Arg Ile Gln Asn Ile Pro Ile Leu Gln Gly Ala Leu Ala Arg Ala
        195                 200                 205

Glu Glu Phe Leu Ser Lys Leu Pro Leu Ala Thr Pro Tyr Ser Glu Phe
    210                 215                 220

Glu Phe Glu Leu Gln Gly Met Gly Phe Glu Arg Gly Trp Gly Asp Thr
225                 230                 235                 240

Ala Gln Lys Val Ser Glu Met Val His Leu Leu Leu Asp Ile Leu Gln
                245                 250                 255

Ala Pro Asp Pro Ser Val Leu Glu Thr Phe Leu Gly Arg Ile Pro Met
            260                 265                 270

Val Phe Asn Val Val Ile Leu Ser Pro His Gly Tyr Phe Gly Gln Ala
        275                 280                 285

Asn Val Leu Gly Leu Pro Asp Thr Gly Gly Gln Val Val Tyr Ile Leu
    290                 295                 300

Asp Gln Val Arg Ala Leu Glu Asn Glu Met Leu Leu Arg Ile Gln Lys
305                 310                 315                 320

Gln Gly Leu Glu Val Ile Pro Lys Ile Leu Ile Val Thr Arg Leu Leu
                325                 330                 335

Pro Glu Ala Lys Gly Thr Thr Cys Asn Gln Arg Leu Glu Arg Val Ser
```

```
              340             345             350
Gly Thr Glu His Ala His Ile Leu Arg Ile Pro Phe Arg Thr Glu Lys
            355                 360                 365
Gly Ile Leu Arg Lys Trp Ile Ser Arg Phe Asp Val Trp Pro Tyr Leu
        370                 375                 380
Glu Thr Phe Ala Glu Asp Ala Ser Asn Glu Ile Ser Ala Glu Leu Gln
385                 390                 395                 400
Gly Val Pro Asn Leu Ile Ile Gly Asn Tyr Ser Asp Gly Asn Leu Val
                405                 410                 415
Ala Ser Leu Leu Ala Ser Lys Leu Gly Val Ile Gln Cys Asn Ile Ala
                420                 425                 430
His Ala Leu Glu Lys Thr Lys Tyr Pro Glu Ser Asp Ile Tyr Trp Arg
                435                 440                 445
Asn His Glu Asp Lys Tyr His Phe Ser Ser Gln Phe Thr Ala Asp Leu
            450                 455                 460
Ile Ala Met Asn Asn Ala Asp Phe Ile Ile Thr Ser Thr Tyr Gln Glu
465                 470                 475                 480
Ile Ala Gly Ser Lys Asn Asn Val Gly Gln Tyr Glu Ser His Thr Ala
                485                 490                 495
Phe Thr Met Pro Gly Leu Tyr Arg Val Val His Gly Ile Asp Val Phe
            500                 505                 510
Asp Pro Lys Phe Asn Ile Val Ser Pro Gly Ala Asp Met Thr Ile Tyr
            515                 520                 525
Phe Pro Tyr Ser Asp Lys Glu Arg Arg Leu Thr Ala Leu His Glu Ser
            530                 535                 540
Ile Glu Glu Leu Leu Phe Ser Ala Glu Gln Asn Asp Glu His Val Gly
545                 550                 555                 560
Leu Leu Ser Asp Gln Ser Lys Pro Ile Ile Phe Ser Met Ala Arg Leu
                565                 570                 575
Asp Arg Val Lys Asn Leu Thr Gly Leu Val Glu Cys Tyr Ala Lys Asn
                580                 585                 590
Ser Lys Leu Arg Glu Leu Ala Asn Leu Val Ile Val Gly Gly Tyr Ile
            595                 600                 605
Asp Glu Asn Gln Ser Arg Asp Arg Glu Glu Met Ala Glu Ile Gln Lys
            610                 615                 620
Met His Ser Leu Ile Glu Gln Tyr Asp Leu His Gly Glu Phe Arg Trp
625                 630                 635                 640
Ile Ala Ala Gln Met Asn Arg Ala Arg Asn Gly Glu Leu Tyr Arg Tyr
                645                 650                 655
Ile Ala Asp Thr Lys Gly Val Phe Val Gln Pro Ala Phe Tyr Glu Ala
                660                 665                 670
Phe Gly Leu Thr Val Val Glu Ser Met Thr Cys Ala Leu Pro Thr Phe
            675                 680                 685
Ala Thr Cys His Gly Gly Pro Ala Glu Ile Ile Glu Asn Gly Val Ser
            690                 695                 700
Gly Phe His Ile Asp Pro Tyr His Pro Asp Gln Val Ala Ala Thr Leu
705                 710                 715                 720
Val Ser Phe Phe Glu Thr Cys Asn Thr Asn Pro Asn His Trp Val Lys
                725                 730                 735
Ile Ser Glu Gly Gly Leu Lys Arg Ile Tyr Glu Arg Tyr Thr Trp Lys
                740                 745                 750
Lys Tyr Ser Glu Arg Leu Leu Thr Leu Ala Gly Val Tyr Ala Phe Trp
            755                 760                 765
```

```
Lys His Val Ser Lys Leu Glu Arg Arg Glu Thr Arg Arg Tyr Leu Glu
        770                 775                 780

Met Phe Tyr Ser Leu Lys Phe Arg Asp Leu Ala Asn Ser Ile Pro Leu
785                 790                 795                 800

Ala Thr Asp Glu Asn
            805

<210> SEQ ID NO 29
<211> LENGTH: 2394
<212> TYPE: DNA
<213> ORGANISM: Arabidopsis thaliana

<400> SEQUENCE: 29
atgtgtgttg tgattggtct caagtcatgg gtaatggttt tggttgttat ctttattaga      60
tatgtagccc agggaaaggg gatattgcag tcccaccagc tgattgatga gttccttaag     120
actgtgaaag ttgatggaac attagaagat cttaacaaaa gtccattcat gaaagttctg     180
cagtctgcag aggaagccat agttttgcct ccatttgttg ctttggctat acgtcccaga     240
cctggtgtta gggaatatgt ccgtgtgaat gtgtatgagc tgagcgtaga tcatttaact     300
gtttctgaat atcttcggtt taaggaagag ctcgttaatg ccatgccaa tggagattat      360 ctccttgaac ttgattttga acctttcaat gcaacattgc ctcgcccaac tcgttcatca     420
tccattggga atggggttca gttcctcaat cgtcacctct cttcaattat gttccgtaac     480
aaagaaagca tggagccttt gcttgagttt ctccgcactc acaaacatga tggccgtcct     540
atgatgctga atgatcgaat acagaatatc cccatacttc agggagcttt ggcaagagca     600
gaggagttcc tttctaaact tcctctggca acaccatact ctgaattcga atttgaacta     660
caagggatgg gatttgaaag gggatggggt gacacagcac agaaggtttc agaaatggtg     720
catcttcttc tggacatact ccaggcacct gatccttctg tcttggagac gtttctagga     780
aggattccta tggtgttcaa tgttgtgatt ttgtctccgc atggttactt ggccaagcc      840 aatgtcttgg gtctgcctga tactggtgga caggttgtct acattcttga tcaagtacgt     900
gcattggaaa atgagatgct ccttaggata cagaagcaag gactggaagt tattccaaag     960
attctcattg taacaagact gctacccgaa gcaaagggaa caacgtgcaa ccagaggtta    1020
gaaagagtta gtggtacaga acacgcacac attctgcgaa taccatttag gactgaaaag    1080
ggaattcttc gcaagtggat ctcaaggttt gatgtctggc atacctggga gcttttgca     1140 gaggatgcat caaatgaaat ttctgcggag ttgcagggtg taccaaatct catcattggc    1200
aactacagtg atggaaatct cgttgcttct tgttagcta gtaagctagg tgtgatacag     1260
tgtaatattg ctcatgcttt agagaaaacc aagtaccccg agtctgacat ttactggaga    1320
aaccatgaag ataagtatca cttttcaagt cagttcactg cagatctaat tgccatgaat    1380
aatgccgatt tcatcatcac cagcacatac aagagattgc gggaagcaa gaacaatgtt     1440 gggcaatacg agagccacac agctttcact atgcctggtc tttaccgagt tgttcatgga    1500
attgatgtct ttgatcctaa gtttaatatg gtctctccag gagctgatat gaccatatac    1560
tttccatatt ccgacaagga aagaagactc actgcccttc atgagtcaat tgaagaactc    1620
ctctttagtg ccgaacagaa tgatgagcat gttggtttac tgagcgacca atcgaagcca    1680
atcatcttct ctatggcaag acttgacagg gtgaaaaact tgactgggct agttgaatgc    1740
tatgccaaga atagcaagct tagagagctt gcaaatcttg ttatagtcgg tggctacatc    1800
gatgagaatc agtccaggga tagagaggaa atggctgaga tacaaaagat gcacagcctg    1860
attgagcagt atgatttaca cggtgagttt aggtggatag ctgctcaaat gaaccgtgct    1920
```

```
cgaaatggtg agctttaccg ttatatcgca gacacaaaag gtgttttgt tcagcctgct    1980 ttctatgaag catttgggct tacggttgtg gaatcaatga cttgtgcact cccaacgttt    2040
gctacctgtc atggtggacc cgcagagatt atcgaaaacg gagtttctgg gttccacatt    2100
gacccatatc atccagacca ggttgcagct accttggtca gcttctttga gacctgtaac    2160
accaatccaa atcattgggt taaaatctct gaaggagggc tcaagcgaat ctatgaaagg    2220
tacacatgga agaagtactc agagagactg cttaccctgg ctggagtcta tgcattctgg    2280
aaacatgtgt ctaagctcga aaggagagaa acacgacgtt acctagagat gttttactca    2340
ttgaaatttc gtgatttggc caattcaatc ccgctggcaa cagatgagaa ctga           2394
```

<210> SEQ ID NO 30
<211> LENGTH: 797
<212> TYPE: PRT
<213> ORGANISM: Arabidopsis thaliana

<400> SEQUENCE: 30

```
Met Cys Val Val Ile Gly Leu Lys Ser Trp Val Met Val Leu Val Val
  1               5                  10                  15

Ile Phe Ile Arg Tyr Val Ala Gln Gly Lys Gly Ile Leu Gln Ser His
             20                  25                  30

Gln Leu Ile Asp Glu Phe Leu Lys Thr Val Lys Val Asp Gly Thr Leu
         35                  40                  45

Glu Asp Leu Asn Lys Ser Pro Phe Met Lys Val Leu Gln Ser Ala Glu
     50                  55                  60

Glu Ala Ile Val Leu Pro Pro Phe Val Ala Leu Ala Ile Arg Pro Arg
 65                  70                  75                  80

Pro Gly Val Arg Glu Tyr Val Arg Val Asn Val Tyr Glu Leu Ser Val
                 85                  90                  95

Asp His Leu Thr Val Ser Glu Tyr Leu Arg Phe Lys Glu Glu Leu Val
            100                 105                 110

Asn Gly His Ala Asn Gly Asp Tyr Leu Leu Glu Leu Asp Phe Glu Pro
        115                 120                 125

Phe Asn Ala Thr Leu Pro Arg Pro Thr Arg Ser Ser Ser Ile Gly Asn
    130                 135                 140

Gly Val Gln Phe Leu Asn Arg His Leu Ser Ser Ile Met Phe Arg Asn
145                 150                 155                 160

Lys Glu Ser Met Glu Pro Leu Leu Glu Phe Leu Arg Thr His Lys His
                165                 170                 175

Asp Gly Arg Pro Met Met Leu Asn Asp Arg Ile Gln Asn Ile Pro Ile
            180                 185                 190

Leu Gln Gly Ala Leu Ala Arg Ala Glu Glu Phe Leu Ser Lys Leu Pro
        195                 200                 205

Leu Ala Thr Pro Tyr Ser Glu Phe Glu Phe Glu Leu Gln Gly Met Gly
    210                 215                 220

Phe Glu Arg Gly Trp Gly Asp Thr Ala Gln Lys Val Ser Glu Met Val
225                 230                 235                 240

His Leu Leu Leu Asp Ile Leu Gln Ala Asp Pro Ser Val Leu Glu
                245                 250                 255

Thr Phe Leu Gly Arg Ile Pro Met Val Phe Asn Val Val Ile Leu Ser
            260                 265                 270

Pro His Gly Tyr Phe Gly Gln Ala Asn Val Leu Gly Leu Pro Asp Thr
        275                 280                 285

Gly Gly Gln Val Val Tyr Ile Leu Asp Gln Val Arg Ala Leu Glu Asn
```

```
            290                 295                 300
Glu Met Leu Leu Arg Ile Gln Lys Gln Gly Leu Glu Val Ile Pro Lys
305                 310                 315                 320

Ile Leu Ile Val Thr Arg Leu Leu Pro Glu Ala Lys Gly Thr Thr Cys
                325                 330                 335

Asn Gln Arg Leu Glu Arg Val Ser Gly Thr Glu His Ala His Ile Leu
                340                 345                 350

Arg Ile Pro Phe Arg Thr Glu Lys Gly Ile Leu Arg Lys Trp Ile Ser
                355                 360                 365

Arg Phe Asp Val Trp Pro Tyr Leu Glu Thr Phe Ala Glu Asp Ala Ser
370                 375                 380

Asn Glu Ile Ser Ala Glu Leu Gln Gly Val Pro Asn Leu Ile Ile Gly
385                 390                 395                 400

Asn Tyr Ser Asp Gly Asn Leu Val Ala Ser Leu Leu Ala Ser Lys Leu
                405                 410                 415

Gly Val Ile Gln Cys Asn Ile Ala His Ala Leu Glu Lys Thr Lys Tyr
                420                 425                 430

Pro Glu Ser Asp Ile Tyr Trp Arg Asn His Glu Asp Lys Tyr His Phe
                435                 440                 445

Ser Ser Gln Phe Thr Ala Asp Leu Ile Ala Met Asn Asn Ala Asp Phe
450                 455                 460

Ile Ile Thr Ser Thr Tyr Gln Glu Ile Ala Gly Ser Lys Asn Asn Val
465                 470                 475                 480

Gly Gln Tyr Glu Ser His Thr Ala Phe Thr Met Pro Gly Leu Tyr Arg
                485                 490                 495

Val Val His Gly Ile Asp Val Phe Asp Pro Lys Phe Asn Met Val Ser
                500                 505                 510

Pro Gly Ala Asp Met Thr Ile Tyr Phe Pro Tyr Ser Asp Lys Glu Arg
                515                 520                 525

Arg Leu Thr Ala Leu His Glu Ser Ile Glu Glu Leu Leu Phe Ser Ala
                530                 535                 540

Glu Gln Asn Asp Glu His Val Gly Leu Leu Ser Asp Gln Ser Lys Pro
545                 550                 555                 560

Ile Ile Phe Ser Met Ala Arg Leu Asp Arg Val Lys Asn Leu Thr Gly
                565                 570                 575

Leu Val Glu Cys Tyr Ala Lys Asn Ser Lys Leu Arg Glu Leu Ala Asn
                580                 585                 590

Leu Val Ile Val Gly Gly Tyr Ile Asp Glu Asn Gln Ser Arg Asp Arg
                595                 600                 605

Glu Glu Met Ala Glu Ile Gln Lys Met His Ser Leu Ile Glu Gln Tyr
610                 615                 620

Asp Leu His Gly Glu Phe Arg Trp Ile Ala Ala Gln Met Asn Arg Ala
625                 630                 635                 640

Arg Asn Gly Glu Leu Tyr Arg Tyr Ile Ala Asp Thr Lys Gly Val Phe
                645                 650                 655

Val Gln Pro Ala Phe Tyr Glu Ala Phe Gly Leu Thr Val Val Glu Ser
                660                 665                 670

Met Thr Cys Ala Leu Pro Thr Phe Ala Thr Cys His Gly Gly Pro Ala
                675                 680                 685

Glu Ile Ile Glu Asn Gly Val Ser Gly Phe His Ile Asp Pro Tyr His
                690                 695                 700

Pro Asp Gln Val Ala Ala Thr Leu Val Ser Phe Phe Glu Thr Cys Asn
705                 710                 715                 720
```

| | | | | | | | | | | | |
|---|---|---|---|---|---|---|---|---|---|---|---|
|Thr|Asn|Pro|Asn|His|Trp|Val|Lys|Ile|Ser|Glu|Gly|Gly|Leu|Lys|Arg|
| | | |725| | | |730| | | |735|

Ile Tyr Glu Arg Tyr Thr Trp Lys Lys Tyr Ser Glu Arg Leu Leu Thr
           740                      745                   750

Leu Ala Gly Val Tyr Ala Phe Trp Lys His Val Ser Lys Leu Glu Arg
      755                     760                     765

Arg Glu Thr Arg Arg Tyr Leu Glu Met Phe Tyr Ser Leu Lys Phe Arg
 770                  775                 780

Asp Leu Ala Asn Ser Ile Pro Leu Ala Thr Asp Glu Asn
785                790                   795

<210> SEQ ID NO 31
<211> LENGTH: 1533
<212> TYPE: DNA
<213> ORGANISM: Arabidopsis thaliana

<400> SEQUENCE: 31

```
atgtcgaaca tagacataga agggatcttg aaggagctac ctaatgatgg gaggatccca      60
aagacgaaga tagtttgcac attaggacca gcttctcgca ctgtttccat gatcgaaaag     120
cttttgaaag ccggtatgaa tgtggctcgc ttcaacttct cacatggaag ccatgaatac     180
catcaagaga cactcgacaa cctccgctct gctatgcata taccggcat tctcgctgct     240
gtcatgcttg atactaaggg gcctgagatt cgtactggtt tcttgaaaga tgggaaccct     300
atacaactga aggaaggtca agagattact ataaccactg attatgacat tcaaggagac     360
gaatcaacga tatccatgag ctataaaaag ctgcctttgg atgtgaagcc cggaaacacc     420
atactctgtg cagatggaag cataagtcta gctgtcttgt catgtgatcc tgagtctgga     480
actgttaggt gccggtgtga aaactcggcg atgcttggtg aaagaaagaa tgtgaatctt     540
cctggcgttg ttgttgatct tcccactttg acagataagg atattgaaga tattctcggt     600
tggggtgttc cgaacagcat tgatatgatt gctctttcgt ttgtccgtaa aggttcggat     660
cttgttaatg tccgcaaggt tcttggatct catgctaaaa gcataatgct catgtcaaag     720
gttgagaacc aggaaggtgt gattaacttt gatgagatct tgcgtgaaac agatgcgttc     780
atggttgccc gtggtgatct cgggatggag attccgatag agaagatctt cttggctcaa     840
aagttgatga tctacaagtg taaccttgcg ggtaaaccgg tggtcacagc cactcagatg     900
ctggagtcaa tgatcaaatc acctcggcca acccgagctg aagccacaga tgttgcaaat     960
gctgttcttg atggtactga ctgtgtgatg cttagcggtg agagtgcagc aggagcttat    1020
ccggaaatag ctgtgaaagt catggctaag atctgcattg aagccgaatc ctcgcttgat    1080
tacaacacaa tctttaaaga gatgatccga gcaactccac ttccaatgag cccactcgag    1140
agtcttgcat catccgctgt acggactgct aacaaagcga gggcaaaact catcattgtg    1200
ttgacacgtg gaggttcaac tgctaatctc gtggctaaat acagaccggc tgttccgatt    1260
ctgtcagtgg ttgtcccggt tatgaccact gattcctttg actggtcttg tagtgacgag    1320
tcacctgcaa ggcatagtct gatatacaga ggtctaatcc ctatgttggc tgaaggatct    1380
gcaaaggcaa cagatagtga agccaccgaa gttatcattg aagctgctct gaagtcggct    1440
actcagagag gactgtgcaa ccgtggtgat gcaatcgtgg cgctgcaccg tattggagct    1500
gcctcagtta ttaagatctg tgtggttaag tga                                 1533
```

<210> SEQ ID NO 32
<211> LENGTH: 510
<212> TYPE: PRT
<213> ORGANISM: Arabidopsis thaliana

<400> SEQUENCE: 32

```
Met Ser Asn Ile Asp Ile Glu Gly Ile Leu Lys Glu Leu Pro Asn Asp
  1               5                  10                  15
Gly Arg Ile Pro Lys Thr Lys Ile Val Cys Thr Leu Gly Pro Ala Ser
             20                  25                  30
Arg Thr Val Ser Met Ile Glu Lys Leu Leu Lys Ala Gly Met Asn Val
         35                  40                  45
Ala Arg Phe Asn Phe Ser His Gly Ser His Glu Tyr His Gln Glu Thr
     50                  55                  60
Leu Asp Asn Leu Arg Ser Ala Met His Asn Thr Gly Ile Leu Ala Ala
 65                  70                  75                  80
Val Met Leu Asp Thr Lys Gly Pro Glu Ile Arg Thr Gly Phe Leu Lys
                 85                  90                  95
Asp Gly Asn Pro Ile Gln Leu Lys Glu Gly Gln Glu Ile Thr Ile Thr
            100                 105                 110
Thr Asp Tyr Asp Ile Gln Gly Asp Glu Ser Thr Ile Ser Met Ser Tyr
        115                 120                 125
Lys Lys Leu Pro Leu Asp Val Lys Pro Gly Asn Thr Ile Leu Cys Ala
130                 135                 140
Asp Gly Ser Ile Ser Leu Ala Val Leu Ser Cys Asp Pro Glu Ser Gly
145                 150                 155                 160
Thr Val Arg Cys Arg Cys Glu Asn Ser Ala Met Leu Gly Glu Arg Lys
                165                 170                 175
Asn Val Asn Leu Pro Gly Val Val Asp Leu Pro Thr Leu Thr Asp
            180                 185                 190
Lys Asp Ile Glu Asp Ile Leu Gly Trp Gly Val Pro Asn Ser Ile Asp
        195                 200                 205
Met Ile Ala Leu Ser Phe Val Arg Lys Gly Ser Asp Leu Val Asn Val
    210                 215                 220
Arg Lys Val Leu Gly Ser His Ala Lys Ser Ile Met Leu Met Ser Lys
225                 230                 235                 240
Val Glu Asn Gln Glu Gly Val Ile Asn Phe Asp Glu Ile Leu Arg Glu
                245                 250                 255
Thr Asp Ala Phe Met Val Ala Arg Gly Asp Leu Gly Met Glu Ile Pro
            260                 265                 270
Ile Glu Lys Ile Phe Leu Ala Gln Lys Leu Met Ile Tyr Lys Cys Asn
        275                 280                 285
Leu Ala Gly Lys Pro Val Val Thr Ala Thr Gln Met Leu Glu Ser Met
    290                 295                 300
Ile Lys Ser Pro Arg Pro Thr Arg Ala Glu Ala Thr Asp Val Ala Asn
305                 310                 315                 320
Ala Val Leu Asp Gly Thr Asp Cys Val Met Leu Ser Gly Glu Ser Ala
                325                 330                 335
Ala Gly Ala Tyr Pro Glu Ile Ala Val Lys Val Met Ala Lys Ile Cys
            340                 345                 350
Ile Glu Ala Glu Ser Ser Leu Asp Tyr Asn Thr Ile Phe Lys Glu Met
        355                 360                 365
Ile Arg Ala Thr Pro Leu Pro Met Ser Pro Leu Glu Ser Leu Ala Ser
    370                 375                 380
Ser Ala Val Arg Thr Ala Asn Lys Ala Arg Ala Lys Leu Ile Ile Val
385                 390                 395                 400
Leu Thr Arg Gly Gly Ser Thr Ala Asn Leu Val Ala Lys Tyr Arg Pro
                405                 410                 415
```

```
Ala Val Pro Ile Leu Ser Val Val Pro Val Met Thr Thr Asp Ser
            420                 425                 430

Phe Asp Trp Ser Cys Ser Asp Glu Ser Pro Ala Arg His Ser Leu Ile
        435                 440                 445

Tyr Arg Gly Leu Ile Pro Met Leu Ala Glu Gly Ser Ala Lys Ala Thr
        450                 455                 460

Asp Ser Glu Ala Thr Glu Val Ile Ile Glu Ala Ala Leu Lys Ser Ala
465                 470                 475                 480

Thr Gln Arg Gly Leu Cys Asn Arg Gly Asp Ala Ile Val Ala Leu His
                485                 490                 495

Arg Ile Gly Ala Ala Ser Val Ile Lys Ile Cys Val Val Lys
                500                 505                 510

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 33
ataagaatgc ggccgcatgc cagggatcac actag                           35

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 34
ataagaatgc ggccgctcaa gagacctctg tgtga                           35

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 35
gcggatccag agaaatgtgt tcattagag                                  29

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 36
cgtctagagt tctaaagttt agatccagt                                  29

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 37
ataagaatgc ggccgcatgt ctccacttct ccggtttag                       39
```

```
<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 38
ataagaatgc ggccgctcac aacttgatgc taattc                              36

<210> SEQ ID NO 39
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 39
ataagaatgc ggccgcatgc gcttccgatc attcttcttc tcctcctcta tc            52

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 40
ataagaatgc ggccgcttat agtttgttct cgcgg                               35

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 41
atggcgcgcc atgttgccca gattagctcg agtcg                               35

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 42
gcttaattaa ctaacagcta gcacattccc ttgtg                               35

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 43
atggcgcgcc atgttgccca gattagctcg agtcg                               35

<210> SEQ ID NO 44
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 44
```

```
gcttaattaa ctaacagcta gcacattccc ttgtg                                 35

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 45
atggcgcgcc atgtcggccg gtaacggaaa tgctac                               36

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 46
gcttaattaa ctaaaagata ggaccagcag cgag                                 34

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 47
atggcgcgcc atggtttcgt ttacgggttt cgc                                  33

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 48
gcttaattaa tcaaggtcct ctcatctttt caaca                                35

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 49
atggcgcgcc atggtttcgt ttacgggttt cgc                                  33

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 50
gcttaattaa tcaaggtcct ctcatctttt caaca                                35

<210> SEQ ID NO 51
<211> LENGTH: 36
<212> TYPE: DNA
<213> ORGANISM: Artificial Sequence
```

```
<220> FEATURE:
<223> OTHER INFORMATION: Description of Artificial Sequence: Primer

<400> SEQUENCE: 51
atggcgcgcc aagactaaca tggaaattga tggccg                                   36

<210> SEQ ID NO 52
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 52
gcttaattaa cttctaccgg gtttttcac tacg                                      34

<210> SEQ ID NO 53
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 53
atggcgcgcc atggggttag agaggaaagt gtacgg                                   36

<210> SEQ ID NO 54
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 54
gcttaattaa tcagagctca gcatcatcgt cggt                                     34

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 55
atggcgcgcc atggcgactc aattcagcgc ttc                                      33

<210> SEQ ID NO 56
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 56
gcttaattaa ttacttcttc tcgttgatga gctcttc                                  37

<210> SEQ ID NO 57
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 57
atggcgcgcc atggcggcta ctagagtgtt aactg                                    35
```

```
<210> SEQ ID NO 58
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 58
gcttaattaa tcagtaaagt gaaaggtctc cagca                              35

<210> SEQ ID NO 59
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 59
atggcgcgcc aacaatggcg tctttctttg atctcg                             36

<210> SEQ ID NO 60
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 60
gcttaattaa tcagttctca tctgttgcca g                                  31

<210> SEQ ID NO 61
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 61
atggcgcgcc aacaatggcg tctttctttg atctcg                             36

<210> SEQ ID NO 62
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 62
gcttaattaa tcagttctca tctgttgcca g                                  31

<210> SEQ ID NO 63
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 63
atggcgcgcc atgtcgaaca tagacataga agggatc                            37

<210> SEQ ID NO 64
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 64
```

```
gcttaattaa tcacttaacc acacagatct taataactg                              39

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 65
caggaaacag ctatgacc                                                     18

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 66
ctaaagggaa caaaagctg                                                    19

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 67
tgtaaaacga cggccagt                                                     18
```